(12) United States Patent
Moy et al.

(10) Patent No.: US 11,268,070 B2
(45) Date of Patent: Mar. 8, 2022

(54) METHODS FOR CREATING INTEGRATION-FREE, VIRUS-FREE, EXOGENOUS ONCOGENE-FREE IPS CELLS AND COMPOSITIONS FOR USE IN SUCH METHODS

(71) Applicant: Cellular Engineering Technologies, Inc., Coralville, IA (US)

(72) Inventors: Alan B. Moy, Iowa City, IA (US); Anant Kamath, Iowa City, IA (US)

(73) Assignee: CELLULAR ENGINEERING TECHNOLOGIES, INC., Coralville, IA (US)

(*) Notice: Subject to any disclaimer, the term of this patent is extended or adjusted under 35 U.S.C. 154(b) by 166 days.

(21) Appl. No.: 15/954,291

(22) Filed: Apr. 16, 2018

(65) Prior Publication Data

US 2019/0316095 A1 Oct. 17, 2019

(51) Int. Cl.
| C12N 5/02 | (2006.01) |
| C12N 15/79 | (2006.01) |
| C07H 21/04 | (2006.01) |
| C12N 5/074 | (2010.01) |
| C12N 15/85 | (2006.01) |

(52) U.S. Cl.
CPC .......... *C12N 5/0696* (2013.01); *C12N 15/85* (2013.01); *C12N 2310/11* (2013.01); *C12N 2330/51* (2013.01); *C12N 2500/92* (2013.01); *C12N 2501/115* (2013.01); *C12N 2501/15* (2013.01); *C12N 2506/03* (2013.01); *C12N 2506/09* (2013.01); *C12N 2506/11* (2013.01); *C12N 2710/00041* (2013.01); *C12N 2800/108* (2013.01); *C12N 2800/24* (2013.01)

(58) Field of Classification Search
CPC ...... C12N 5/06; C12N 15/85; C12N 2506/00; C12N 2506/1307; C12N 2800/108; C07H 21/04
See application file for complete search history.

(56) References Cited

U.S. PATENT DOCUMENTS

| 8,048,999 | B2 | 11/2011 | Yamanaka et al. |
| 2013/0267030 | A1* | 10/2013 | Yamanaka et al. |
| 2015/0191701 | A1* | 7/2015 | Shi et al. |
| 2015/0376646 | A1* | 12/2015 | Flynn et al. |
| 2016/0145582 | A1 | 5/2016 | Yu |
| 2016/0257938 | A1* | 9/2016 | Zhu et al. |
| 2017/0369904 | A1* | 12/2017 | Lim et al. |

OTHER PUBLICATIONS

Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Kim et al., 2014, IOVS, vol. 55, No. 8, p. 5099-5108.*
Stern-Straeter et al., 2014, International Journal of Molecular Medicine, vol. 33, p. 160-170.*
Keisuke Okita et al., A more efficient method to generate integration-free human iPS cells, 8(5) Nature Methods, 409 (2011).
Junying Yu et al., Human induced pluripotent stem cells free of vector and transgene sequences, 324(5928) Science 797-801 (2009).
Keisuke Okita et al., An Efficient Nonviral Method to Generate Integration-Free Human-Induced Pluripotent Stem Cells from Cord Blood and Peripheral Blood Cells, 31 Stem Cells 458 (2013).
Xiaohui Yin et al., Generation and periodontal differentiation of human gingival fibroblasts-derived integration-free induced pluripotent stem cells, 473(3) Biochemical and Biophysical Research Commc'Ns, 726 (2016).
Frederick Anokye-Danso et al., Highly efficient miRNA-mediated reprogramming of mouse and human somatic cells to pluripotency, 8(4) Cell: Stem Cell 376 (2011).
Wenli Yang et al., iPSC Reprogramming from Human Peripheral Blood Using Sendai Virus Mediated Gene Transfer (Jun. 10, 2012), in StemBook, (Lisa Girard, ed) (2013).
Anant Kamath et al., Efficient method to create integration-free, virus-free Myc and Lin28-free human induced pluripotent stem cells from adherent cells, 3(3) Future Science OA FSO211 (2017), published online May 12, 2017.
Junying Yu et al., Induced pluripotent stem cell lines derived from human somatic cells, 318 Science 1917 (Dec. 21, 2007).
Kazutoshi Takahashi, et al., Induction of pluripotent stem cells from adult human fibroblasts by defined factors, 131 Cell 861 (Nov. 30, 2007).
Masato Nakagawa, et al., Generation of induced pluripotent stem cells without Myc from mouse and human fibroblasts, 26(1) Nature Biotech 101 (published online Nov. 30, 2007).
Masato Nakagawa, et al., Promotion of direct reprogramming by transformation-deficient Myc, 107(32) Proceedings of the National Academy of Science 14152 (published online Jul. 26, 2010).
Tongbiao Zhao, et al., Immunogenicity of induced pluripotent stem cells, 474 Nature 212 (published online May 13, 2011).

* cited by examiner

*Primary Examiner* — Shin Lin Chen
(74) *Attorney, Agent, or Firm* — Greenblum & Bernstein, P.L.C.

(57) ABSTRACT

Methods are disclosed for reprogramming a somatic cell, including an adherent cell and a cell in suspension, into an induced pluripotent stem comprising expressing exogenous Sox-2, exogenous Klf-4, exogenous Oct3/4 from DNA that has not integrated into the genome of the somatic cell, suppressing p53 activity within the somatic cell, and exposing the somatic cell to reprogramming-assistance factors comprising an exogenous Alk-5 inhibitor, an exogenous histone deacetylase inhibitor, and an exogenous activator of glycolysis. Compositions and kits for use in such methods are also disclosed as are cells made by such a method.

19 Claims, 31 Drawing Sheets
(12 of 31 Drawing Sheet(s) Filed in Color)
Specification includes a Sequence Listing.

Figure 2

| Vector | CONDITION | | |
|---|---|---|---|
| | +L-Myc/+Lin28 | -Myc/-Lin28 | +c-Myc |
| N1 | + | + | + |
| N2 | + | - | - |
| N3 | + | + | + |
| N4 | - | - | + |
| N5 | + | + | + |
| N6 | + | + | + |
| N7 | + | + | + |
| Reprogramming Assistance Factors | + | + | + |

Figure 3A

Red Fluorescent Protein (RFP) DNA sequence inserted into pCEP-4 for Vector N1 (SEQ ID NO.: 15):

```
agcgagctgatcaaggagaacatgcacatgaagctgtacatggagggcaccgtgaacaaccaccacttcaagtgcacatc
cgagggcgaaggcaagccctacgagggcacccagaccatgaagatcaaggtggtcgagggcggccctctcccttcgcct
tcgacatcctggctaccagcttcatgtacggcagcaaagccttcatcaaccacacccagggcatcccgactccttaag
cagtccttccctgagggcttcacatggagagaatcaccacatacgaagacggggcgtgctgaccgctacccaggacac
cagcttccagaacggctgcatcatctacaacgtcaagatcaacggggtgaacttcccatccaacggccctgtgatgcaga
agaaaacacgcggctggagggccaacaccgagatgctgtaccccgctgacggcggcctgagaggccacagccagatggcc
ctgaagctcgtgggcgggggctacctgcactgctccttcaagaccacatacagatccaagaaaccgctaagaacctcaa
gatgcccggcttccacttcgtggaccacagactggaaagaatcaaggaggccgacaaagagacctacgtcgagcagcacg
agatggctgtggccaagtactgcgacctccctagcaaactgggcacagataa
```

Red Fluorescent Protein (RFP) amino acid sequence as translated from Vector N1 (SEQ ID NO.: 16):

```
MKLYMEGTVNNHHFKCTSEGEGKPYEGTQTMKIKVVEGGPLPFAFDILATSFMYGSKAFINHTQGIPDFFK
QSFPEGFTWERITTYEDGGVLTATQDTSFQNGCIIYNVKINGVNFPSNGPVMQKKTRGWEANTEMLYPADGGLRGHSQMA
LKLVGGGYLHCSFKTTYRSKKPAKNLKMPGFHFVDHRLERIKEADKETYVEQHEMAVAKYCDLPSKLGHR*
```

Human l-Myc DNA sequence inserted into pCEP-4 for Vector N2 (SEQ ID NO.: 7):

```
atgttcatgccttcttcttttcctacagctcctgggcaacgtgctggttattgtgctgtctcatcatttggcaaagaa
ttcgcccttcaccatggactacgactcgtaccagcactatttctacgactatgactgcggggaggattctaccgctcca
cggcgccagcgaggacatctggaagaaattcgagctggtgccatcgcccccacgtcgccgccctggggcttgggtccc
ggcgcaggggaccccggcccccgggattggtccccggagccgtggcccggagggtgcaccggagacgaagcggaatcccg
ggccactcgaaaggctggggcaggaactacgcctccatcatacgccgtgactgcatgtggagcggcttctcggcccggg
aacggctggagagagctgtgagcgaccggctcgtcctggcgtcgcggggaaccgccaagcgtccgcgccccg
gactgcactcccagcctcgaagccggcaaccggccgccgccccctgtccgctgggcgaaccaagacccaggcctg
ctccgggtccgagagcccaagcgactcggagaatgaagaaattgatgttgtgacagtagagaagaggcagtctctggta
ttcggaagccggtcaccatcacggtgcgagcagacccctggatccctgcatgaagcatttccacatctccatccatcag
caacagcacaactatgctgcccgttttcctccagaaagctgctcccaagaagaggcttcagagaggggtccccaagaaga
ggttctggagagagatgctgcaggggaaggaagatgaggaggatgaagagattgtgagtcccccacctgtagaaagtg
aggctgccagtcctgccaccccaaacctgtcagttctgatactgaccaagaggaagaatcacaacttcctg
gagcgcaaggctggaatgacctgcgttcgcgattcttggcgctgagggaccaggtgcccaccctggccagctgctccaa
ggcccccaaagtagtgatcctaagcaaggccttggaatacttgcaagccctggtgggggctgagaagaggatggctacag
agaaaagacagctccgatgccggcagcagcagttgcagaaaagaattgcataccctcactggctacggagatctcaaaatt
gtcgctcct
```

Human l-Myc amino acid sequence as translated from Vector N2 (SEQ ID NO.: 8):

```
MFMPSSFSYSSWATCWLLCCLIILAKNSPFTMDYDSYQHYFYDYDCGEDFYRSTAPSEDIWKKFELVPSPPTSPPWGLGP
GAGDPAPGIGPPEPWPGGCTGDEAESRGHSKGWGRNYASIIRRDCMWSGFSARERLERAVSDRLAPGAPRGNPPKASAAP
DCTPSLEAGNPAPAAPCPLGEPKTQACSGSESPSDSENEEIDVVTVEKRQSLGIRKPVTITVRADPLDPCMKHFHISIHQ
QQHNYAARFPPESCSQEEASERGPQEEVLERDAAGEKEDEEDEEIVSPPPVESEAAQSCHPKPVSSDTEDVTKRKNHNFL
ERKRRNDLRSRFLALRDQVPTLASCSKAPKVVILSKALEYLQALVGAEKRMATEKRQLRCRQQQLQKRIAYLTGYGDLKI
VAP
```

Human Lin28 DNA sequence inserted into pCEP-4 for Vector N2 (SEQ ID NO.: 5):

```
atgaacaattcgcccttcaccatgggctccgtgtccaaccagcagtttgcaggtggctgcgccaaggcggcagaagaggc
gcccgaggaggcgccggaggacgcggcccggcggcggacgagcctcagctgctgcacggtgcgggcatctgtaagtggt
tcaacgtgcgcatggggttcggcttcctgtccatgaccgccgcgccggggtcgcgctcgaccccagtggatgtctttt
gtgcaccagagtaagctgcacatggaaggggttccggagcttgaaggagggtgaggcagtggagttcacctttaagaagtc
agccaagggtctggaatccatccgtgtcaccggacctggtggagtattctgtattgggagtgagggcggcaaaaggaa
agagcatgcagaagcgcagatcaaaaggagcaggtgctacaactgtggaggtctagatcatcatgccaaggaatgcaag
ctgccaccccagcccaagaagtgccacttctgccagagcatcagccatatggtagcctcatgtccgctgaggcccagca
gggcccctagtgcagggaaagccaacctactttgagaggaagaagaagaaatccacagccctaccctgctccggagg
cacagaattga
```

Figure 3B

Human Lin28 amino acid sequence as translated from Vector N2 (SEQ ID NO.: 6):

```
MNNSPFTMGSVSNQQFAGGCAKAAEEAPEEAPEDAARAADEPQLLHGAGICKWFNVRMGFGFLSMTARAGVALDPPVDVF
VHQSKLHMEGFRSLKEGEAVEFTFKKSAKGLESIRVTGPGGVFCIGSERRPKGKSMQKRRSKGDRCYNCGGLDHHAKECK
LPPQPKKCHFCQSISHMVASCPLKAQQGPSAQGKPTYFREEEEEIHSPTLLPEAQN*
```

Epstein-Barr virus nuclear antigen 1 (EBNA-1) DNA sequence inserted into pCEP-4 for Vector N3 (SEQ ID NO.: 21):

```
ATGTCTGACGAGGGGCCAGGTACAGGACCTGGAAATGGCCTAGGAGAGAAGGGAGACACATCTGGACCAGAAGGCTCCGGCGGC
AGTGGACCTCAAAGAAGAGGGGGTGATAACCATGGACGAGGACGGGGAAGAGGACGAGGACGAGGAGGCGGAAGACCAGGAGCC
CCGGGCGGCTCAGGATCAGGGCCCAAGACATAGAGATGGTGTCCGGAGACCCCAAAAACGTCCAAGTTGCATTGGCTGCAAAGGG
ACCCACGGTGGAACAGGAGCAGGAGCAGGAGCGGGAGGGGCAGGAGCAGGAGGGGCAGGAGCAGGAGGAGGGGCAGGAGCAGGA
GGAGGGGCAGGAGGGGCAGGAGGGGCAGGAGGGGCAGGAGCAGGAGGAGGGGCAGGAGCAGGAGGAGGGGCAGGAGGGGCAGGA
GGGGCAGGAGCAGGAGGAGGGGCAGGAGCAGGAGGAGGGGCAGGAGGGGCAGGAGCAGGAGGAGGGGCAGGAGGGGCAGGAGGG
GCAGGAGCAGGAGGAGGGGCAGGAGCAGGAGGAGGGGCAGGAGGGGCAGGAGCAGGAGGAGGGGCAGGAGGGGCAGGAGGGGCA
GGAGCAGGAGGAGGGGCAGGAGCAGGAGGGGCAGGAGCAGGAGGGGCAGGAGCAGGAGGAGGGGCAGGAGCAGGAGGAGGGGCA
GGAGGGGCAGGAGGGGCAGGAGCAGGAGGGGCAGGAGCAGGAGGGGCAGGAGCAGGAGGGGCAGGAGCAGGAGGGGCAGGAGGG
GCAGGAGCAGGAGGGGCAGGAGGGGCAGGAGCAGGAGGGGCAGGAGGGGCAGGAGCAGGAGGAGGGGCAGGAGGGGCAGGAGCA
GGAGGAGGGGCAGGAGGGGCAGGAGCAGGAGGGGCAGGAGGGGCAGGAGCAGGAGGGGCAGGAGCAGGAGGAGGGGCAGGAGGG
GGAGGGGCAGGAGCAGGAGGGGCAGGAGCAGGAGGGGCAGGAGCAGGAGGTGGAGGCCGGGGTCGAGGAGGCAGTGGAGGC
CGGGGTCGAGGAGGTAGTGGAGGCCGGGGTCGAGGAGGTAGTGGAGGCCGCCGGGGTAGAGGACGTGAAAGAGCCAGGGGGGGA
AGTCGTGAAAGAGCCAGGGGGAGAGGTCGTGGACGTGGAGAAAAGAGGCCCAGGAGTCCCAGTAGTCAGTCATCATCATCCGGG
TCTCCACCGCGCAGGCCCCCTCCAGGTAGAAGGCCATTTTTCCACCCTGTAGGGGAAGCCGATTATTTTGAATACCACCAAGAA
GGTGGCCCAGATGGTGAGCCTGACGTGCCCCCGGGAGCGATAGAGCAGGGCCCCGCAGATGACCCAGGAGAAGGCCCAAGCACT
GGACCCCGGGGTCAGGGTGATGGAGGCAGGCGCAAAAAAGGAGGGTGGTTTGGAAAGCATCGTGGTCAAGGAGGTTCCAACCCG
AAATTTGAGAACATTGCAGAAGGTTTAAGAGCTCTCCTGGCTAGGAGTCACGTAGAAAGGACTACCGACGAAGGAACTTGGGTC
GCCGGTGTGTTCGTATATGGAGGTAGTAAGACCTCCCTTTACAACCTAAGGCGAGGAACTGCCCTTGCTATTCCACAATGTCGT
CTTACACCATTGAGTCGTCTCCCCTTTGGAATGGCCCCTGGACCCGGCCCACAACCTGGCCCGCTAAGGGAGTCCATTGTCTGT
TATTTCATGGTCTTTTTACAAACTCATATATTTGCTGAGGTTTTGAAGGATGCGATTAAGGACCTTGTTATGACAAAGCCCGCT
CCTACCTGCAATATCAGGGTGACTGTGTGCAGCTTTGACGATGGAGTAGATTTGCCTCCCTGGTTTCCACCTATGGTGGAAGGG
GCTGCCGCGGAGGGTGATGACGGAGATGACGGAGATGAAGGAGGTGATGGAGATGAGGGTGAGGAAGGGCAGGAGTGA
```

EBNA-1 sequence as translated from Vector N3 (SEQ ID NO.: 22):

```
MSDEGPGTGPGNGLGEKGDTSGPEGSGGSGPQRRGGDNHGRGRGRGRGRGGGRPGAPGGSGSGPRHRDGVRRPQKRPSCIGCKG
THGGTGAGAGAGGAGAGGAGAGGGAGAGGGAGGAGGAGGAGAGGGAGAGGGAGGAGGAGAGGGAGAGGGAGGAGAGGGAGGAGG
AGAGGGAGAGGGAGGAGGAGAGGGAGGAGGAGAGGGAGGAGGAGAGGGAGAGGGAGGAGGAGAGGGAGGAGGAGAGAGGAGGAG
AGAGGAGGAGAGGGAGGAGGAGAGGGAGGAGGAGAGGAGGAGGAGAGGGAGGAGGAGAGGGAGAGGGAGAGGGAGGGGRGRGGSGG
RGRGGSGGRGRGGSGGRRGRGRERARGGSRERARGRGRGRGEKRPRSPSPSSQSSSSGSPPRRPPPGRRPFFHPVGEADYFEYHQE
GGPDGEPDVPPGAIEQGPADDPGEGPSTGPRGQGDGGRRKKGGWFGKHRGQGGSNPKFENIAEGLRALLARSHVERTTDEGTWV
AGVFVYGGSKTSLYNLRRGTALAIPQCRLTPLSRLPFGMAPGPGPQPGPLRESIVCYFMVFLQTHIFAEVLKDAIKDLVMTKPA
PTCNIRVTVCSFDDGVDLPPWFPPMVEGAAAEGDDGDDGDEGGDGDEGEEGQE*
```

Human c-Myc DNA sequence inserted into pCEP-4 for Vector N4 (SEQ ID NO.: 1):

```
atgccccctcaacgttagcttcaccaacaggaactatgacctcgactacgactcggtgcagccgtatttctactgcgacga
ggaggagaacttctaccagcagcagcagcagagcgagctgcagccccggcgcccagcgaggatatctggaagaaattcg
agctgctgcccacccgcccctgtccctagccgccgctccgggctctgctcgccctcctacgttgcggtcacacccttc
tccttcggggagacaacgacggcggtggcgggagcttctccacggccgaccagctggagatggtgaccgagctgctggg
aggagacatggtgaaccagagtttcatctgcgacccggacgacgagaccttcatcaaaaacatcatcatccaggactgta
tgtggagcggcttctcggccgccgccaagctcgtctcagacaagaaggctcctaccaggctgcgcgcaagacagcggc
agcccgaacccgccgcggcacagcgtctgctccacctccagcttgtacctggatctgagcgcgccgcctcaga
gtgcatcgaccctcggtggtcttcccctaccctctcaacgacagcagctcgcccaagtcctgcgcctcgcaagactcca
gcgccttctctccgtcctcggattctctgctctcctcgacggagtcctccccgcagggcagccccgagccctggtgctc
catgaggagacaccgcccaccaccagcagcgactctgaggaggaacaagaagatgaggaagaaatcgatgttgtttcgt
ggaaaagaggcaggctcctggcaaaaggtcagagtctggatcaccttctgctggaggccacagcaaacctcctcacagcc
cactggtcctcaagaggtgccacgtctccacacatcagcacaactacgcagcgcctccctccactcggaaggactatcct
gctgccaagagggtcaagttggacagtgtcagagtcctgagacagatcagcaacaaccgaaaatgcaccagccccagtc
ctcggacaccgaggagaatgtcaagaggcgaacacacaacgtcttggagcgccagaggaggaacgagctaaaacggagct
ttttgccctgcgtgaccagatcccggagttggaaaacaatgaaaaggcccccaaggtagttatccttaaaaaagccaca
gcatacatcctgtccgtccaagcagaggagcaaaagctcatttctgaagaggacttgttgcggaaacgacgagaacagtt
gaaacacaaacttgaacagctacggaactcttgtgcgtaa
```

Figure 3C

Human c-Myc amino acid sequence as translated from Vector N4 (SEQ ID NO.: 2):

```
MPLNVSFTNRNYDLDYDSVQPYFYCDEEENFYQQQQQSELQPPAPSEDIWKKFELLPTPPLSPSRRSGLCSPSYVAVTPF
SLRGDNDGGGGSFSTADQLEMVTELLGGDMVNQSFICDPDDETFIKNIIIQDCMWSGFSAAAKLVSEKLASYQAARKDSG
SPNPARGHSVCSTSSLYLQDLSAAASECIDPSVVFPYPLNDSSSPKSCASQDSSAFSPSSDSLLSSTESSPQGSPEPLVL
HEETPPTTSSDSEEEQEDEEEIDVVSVEKRQAPGKRSESGSPSAGGHSKPPHSPLVLKRCHVSTHQHNYAAPPSTRKDYP
AAKRVKLDSVRVLRQISNNRKCTSPRSSDTEENVKRRTHNVLERQRRNELKRSFFALRDQIPELENNEKAPKVVILKKAT
AYILSVQAEEQKLISEEDLLRKRREQLKHKLEQLRNSCA*
```

Human Sox-2 DNA sequence inserted into pCEP-4 for Vector N5 (SEQ ID NO.: 17):

```
atgttcatgccttcttctttttcctacagctcctgggcaacgtgctggttattgtgctgtctcatcatttggcaaagaa
ttcgcccttcaccatgtacaacatgatggagacggagctgaagccgccgggccccgcagcaaacttcgggggcggcggcg
gcaactccaccgcggcggcggccggcggcaaccggaagaaaacagccgccggaccgcgtcaagcggcccatgaatgccttcatg
gtgtggtcccgcgggcagcggccgcaagatggcccaggagaacccccaagatgcacaactcggagatcagcaagcgcctggg
cgccgagtggaaactttttgtcggagacggagaagcggccgttcatcgacgaggctaagcggctgcgagcgctgcacatga
aggagcacccggattataaataccggccccggcggaaaaaccaagacgctcatgaagaaggataagtacacgctgcccggc
gggctgctggcccccggcggcaatagcatggcgagcggggtcggggtgggcgcggcctgggcgcgggcgtgaaccagcg
catggacagttacgcgcacatgaacggctggaacaagcgactacagcagcatgatgcaggaccagctgggctaccgcagc
acccggggccctcaatgcgcacgcgcagcgcagatgcagccatgcaccgctacgacgtgagcgccctgcagtacaactcc
atgaccagctcgcagacctacatgaacggctcgccacctacagcatgtcctactcgcagcagggcacccctggcatggc
tcttggctccatgggttcggtggtcaagtccgaggccagctccagccccctgtggttacctcttcctccactccaggg
cgccctgccaggccggggacctccgggacatgatcagcatgtatctccccggcgccgaggtgcggaacccgccgccccc
agcagacttcacatgtcccagcactaccagagcggcccggtgcccggcacgccattaacggcacactgcccctctcaca
catggggatctcaaaattgtcgctcct
```

Human Sox-2 amino acid sequence as translated from Vector N5 (SEQ ID NO.: 18):

```
MFMPSSFSYSSWATCWLLCCLIILAKNSPFTMYNMMETELKPPGPQQTSGGGGGNSTAAAAGGNQKNSPDRVKRPMNAFM
VWSRGQRRKMAQENPKMHNSEISKRLGAEWKLLSETEKRPFIDEAKRLRALHMKEHPDYKYRPRRKTKTLMKKDKYTLPG
GLLAPGGNSMASGVGVGAGLGAGVNQRMDSYAHMNGWSNGSYSMMQDQLGYPQHPGLNAHGAAQMQPMHRYDVSALQYNS
MTSSQTYMNGSPTYSMSYSQQGTPGMALGSMGSVVKSEASSSPPVVTSSSHSRAPCQAGDLRDMISMYLPGAEVPEPAAP
SRLHMSQHYQSGPVPGTAINGTLPLSHMGDLKIVAP
```

Human Klf-4 DNA sequence inserted into pCEP-4 for Vector N5 (SEQ ID NO.: 3):

```
atgaacaattcgcccttcaccatggctgtcagtgacgcgctgctcccatcttttctccacgttcgcgtctggcccggcggg
aagggagaagacactgcgtcaagcaggtgccccgaataaccgctggcgggaggagctctcccacatgaagcgacttcccc
cagtgcttccggccgcccctatgacctggcggcggcgaccgtggccacagacctggagagcggcggagccggtgcggct
tgcggcggtagcaacctggcgcccctacctcggagagagaccgaggagttcaacgatctcctggacctggactttattct
ctccaattcgctgacccatcctccggagtcagtggccgccaccgtgtcctcgtcagcgtcagcctcctcttcgtcgtcgc
cgtcgagcagccggcctgccagccgccacctgcagcttcacctatccgatccgggcgggaacgaccccggcgtg
gcgccgggcggcacgggcggaggcctcctctatgcagggagtccgctcccctccgacggtcccttcaacctggcgga
catcaacgacgtgagccctcggcggcttcgtggccgagctcctgcggccagaattggaccggtgtacattccgccgc
agcagccgcagccgccaggtggcgggctgatgggcaagttcgtgctgaaggcgtcgctgagcgccctggcagcagtac
ggcagcccgtcggtcatcagcgtcagcaaaggcagccctgacggcagccacccggtggtggtggcgccctacaacggcgg
gccgccgcgcacgtgccccaagatcaagcaggaggcggtctcttcgtgcacccacttgggcgctggacccctctcagca
atggccaccggccggctgcacctccccctgggcgcggccggcaggtaccccgaccccgaccctgggtcttgag
gaagtgtgagcgacggactgtcacccgcctgccgcttcctcccggcttcatcccaccgggccaattaccc
atccttcctgcccgatcagatgcagccgcaagtccgccgctccattaccaagagctcatgccacccggttcctgcatgc
cagaggagcccaagccaaagaggggaagacgatcgtggcccggaaaaggaccgccaccacactttgtgattacgcgggc
tgcggcaaaacctacacaaagagttcccatctcaaggcacacctgcgaacccacacaggtgagaaaccttaccactgtga
ctgggacggctgtggatggaaattcgcccgctcagatgaactgaccaggcactaccgtaaacacacggggcaccgcccgt
tccagtgccaaaaatgcgaccgagcattttccaggtcggaccacctcgccttacacatgaagagacatttttaa
```

Human Klf-4 amino acid sequence as translated from Vector N5 (SEQ ID NO.:4):

```
MNNSPFTMAVSDALLPSFSTFASGPAGREKTLRQAGAPNNRWREELSHMKRLPPVLPGRPYDLAAATVATDLESGGAGAA
CGGSNLAPLPRRETEEFNDLLDLDFILSNSLTHPPESVAATVSSSASASSSSSPSSSGPASAPSTCSFTYPIRAGNDPGV
APGGTGGLLYGRESAPPPTAPFNLADINDVSPSGGFVAELLRPELDPVYIPPQQPQPPGGGLMGKFVLKASLSAPGSEY
GSPSVISVSKGSPDGSHPVVVAPYNGGPPRTCPKIKQEAVSSCTHLGAGPPLSNGHRPAAHDFPLGRQLPSRTTPTLGLE
EVLSSRDCHPALPLPPGFHPHPGPNYPSFLPDQMQPQVPPLHYQELMPPGSCMPEEPKPKRGRRSWPRKRTATHTCDYAG
CGKTYTKSSHLKAHLRTHTGEKPYHCDWDGCGWKFARSDELTRHYRKHTGHRPFQCQKCDRAFSRSDHLALHMKRHF*
```

Figure 3D

DNA sequence encoding antisense RNA for p53 mRNA inserted into pCEP-4 for Vector N6 (SEQ ID NO.: 12):

```
GACTCCAGTGGTAATCTAC
```

Oct-3/4 DNA sequence inserted into pCEP-4 for Vector N7 (SEQ ID NO.: 9):

```
atgttcatgccttcttctttttcctacagctcctgggcaacgtgctggttattgtgctgtctcatcatttggcaaagaa
ttcgcccttcaccatggcgggacacctggcttcggatttcgccttctcgccccctccaggtggtggaggtgatgggccag
gggggccggagccgggctgggttgatcctcggacctggctaagcttccaaggccctcctggagggtcaggaatgggccg
ggggttgggccaggctctgaggtgtggggattccccatgccccccgccgtatgagttctgtgggggatggcgtactg
tgggcccaggttggagtgggctagtgcccaaggcggcttggagacctctcagcctgagggcgaagcaggagtcgggg
tggagagcaactccgatggggcctccccggagccctgcaccgtcaccctggtgccgtgaagctggagaaggagaagctg
gagcaaaaccggaggagtcccaggacatcaaagctctgcagaaagaactcgagcaatttgccaagctcctgaagcagaa
gaggatcaccctgggatatacacaggccgatgtgggctcaccctgggggttctatttgggaaggtattcagccaaacga
ccatctgccgctttgaggctctgcagcttagcttcaagaacatgtgtaagctgcggcccttgctgcagaagtgggtggag
gaagctgacaacaatgaaaatcttcaggagatatgcaaagcagaaacctcgtgcaggcccgaaagagaaagcgaaccag
tatcgagaaccgagtgagaggcaacctggagaatttgttcctgcagtgcccgaaacccacactgcagcagatcagccaca
tcgcccagcagcttgggctcgagaaggatgtggtccgagtgtggttctgtaacggcgccagaagggcaagcgatcaagc
agcgactatgcacaacgagaggattttgaggctgctgggtctcctttctcaggggaccagtgtcctttcctctggcccc
agggccccattttggtaccccaggctatgggagccctcacttcactgcactgtactcctcggtcccttttccctgaggggg
aagcctttcccctgtctctgtcaccactctgggctctcccatgcattcaaactga
```

Oct-3/4 amino acid sequence as translated from Vector N7 (SEQ ID NO.: 10):

```
MFMPSSFSYSSWATCWLLCCLIILAKNSPFTMAGHLASDFAFSPPPGGGDGPGGPEPGWVDPRTWLSFQGPPGGPGIGP
GVGPGSEVWGIPPCPPPYEFCGGMAYCGPQVGVGLVPQGGLETSQPEGEAGVGVESNSDGASPEPCTVTPGAVKLEKEKL
EQNPEESQDIKALQKELEQFAKLLKQKRITLGYTQADVGLTLGVLFGKVFSQTTICRFEALQLSFKNMCKLRPLLQKWVE
EADNNENLQEICKAETLVQARKRKRTSIENRVRGNLENLFLQCPKPTLQQISHIAQQLGLEKDVVRVWFCNRRQKGKRSS
SDYAQREDFEAAGSPFSGGPVSFPLAPGPHFGTPGYGSPHFTALYSSVPFPEGEAFPPVSVTTLGSPMHSN*
```

Figure 3E pCEP4 DNA sequence (SEQ ID NO.: 20):

```
GTTGACATTGATTATTGACTAGTTATTAATAGTAATCAATTACGGGGTCATTAGTTCATAGCCCATATATGGAGTTCCGC
GTTACATAACTTACGGTAAATGGCCCGCCTGGCTGACCGCCCAACGACCCCCGCCCATTGACGTCAATAATGACGTATGT
TCCCATAGTAACGCCAATAGGGACTTTCCATTGACGTCAATGGGTGGAGTATTTACGGTAAACTGCCCACTTGGCAGTAC
ATCAAGTGTATCATATGCCAAGTCCGCCCCCTATTGACGTCAATGACGGTAAATGGCCCGCCTGGCATTATGCCCAGTAC
ATGACCTTACGGGACTTTCCTACTTGGCAGTACATCTACGTATTAGTCATCGCTATTACCATGGTGATGCGGTTTTGGCA
GTACACCAATGGGCGTGGATAGCGGTTTGACTCACGGGGATTTCCAAGTCTCCACCCCATTGACGTCAATGGGAGTTTGT
TTTGGCACCAAAATCAACGGGACTTTCCAAAATGTCGTAATAACCCCGCCCCGTTGACGCAAATGGGCGGTAGGCGTGTA
CGGTGGGAGGTCTATATAAGCAGAGCTCGTTTAGTGAACCGTCAGATCTCTAGAAGCTGGGTACCAGCTGCTAGCAAGCT
TGCTAGCGGCCGCTCGAGGCCGGCAAGGCCGGATCCAGACATGATAAGATACATTGATGAGTTTGGACAAACCACAACTA
GAATGCAGTGAAAAAAATGCTTTATTTGTGAAATTTGTGATGCTATTGCTTTATTTGTAACCATTATAAGCTGCAATAAA
CAAGTTAACAACAACAATTGCATTCATTTTATGTTTCAGGTTCAGGGGGAGGTGTGGGAGGTTTTTTAAAGCAAGTAAAA
CCTCTACAAATGTGGTATGGCTGATTATGATCCGGCTGCCTCGCGCGTTTCGGTGATGACGGTGAAAACCTCTGACACAT
GCAGCTCCCGGAGACGGTCACAGCTTGTCTGTAAGCGGATGCCGGGAGCAGACAAGCCCGTCAGGGCGTCAGCGGGTGTTG
GCGGGTGTCGGGGCGCAGCCATGAGGTCGACTCTAGAGGATCGATGCCCGCCCCGGACGAACTAAACCTGACTACGACA
TCTCTGCCCCTTCTTCGCGGGGCAGTGCATGTAATCCCTTCAGTTGGTTGGTACAACTTGCCAACTGGGCCCTGTTCCAC
ATGTGACACGGGGGGCACCAAACACAAAGGGGTTCTCTGACTGTAGTTGACATCCTTATAAATGGATGTGCACATTTGC
CAACACTGAGTGGCTTTCATCCTGGAGCAGACTTTGCAGTCTGTGGACTGCAACACAACATTGCCTTTATGTGTAACTCT
TGGCTGAAGCTCTTACACCAATGCTGGGGGACATGTACCTCCCAGGGGCCCAGGAAGACTACGGGAGGCTACACCAACGT
CAATCAGAGGGGCCTGTGTAGCTACAGTAAGCGGACCCTCAAGAGGGCATTAGCAATAGTGTTTATAAGGCCCCCTTGT
TAACCCTAAACGGGTAGCATATGCTTCCCGGGTAGTAGTATATACTATCCAGACTAACCCTAATTCAATAGCATATGTTA
CCCAACGGGAAGCATATGCTATCGAATTAGGGTTAGTAAAAGGGTCCTAAGGAACAGCGATATCTCCCACCCCATGAGCT
GTCACGGTTTTATTTACATGGGGTCAGGATTCCACGAGGGTAGTGAACCATTTTAGTCACAAGGGCAGTGGCTGAAGATC
AAGGAGCGGGCAGTGAACTCTCCTGAATCTTCGCCTGCTTCTTCATTCTCCTTCGTTTAGCTAATAGAATAACTGCTGAG
TTGTGAACAGTAAGGTGTATGTGAGGTGCTCGAAAACAAGGTTTCAGGTGACGCCCCCAGAATAAAATTTGGACGGGGGG
TTCAGTGGTGGCATTGTGCTATGACACCAATATAACCCTTGGGCAATAAATACTAGTGTAGGAATGAAA
CATTCTGAATATCTTTAACAATAGAAATCATGGGGTGGGACAAGCGTAAAGACTGGATGTCCATCTCACACGAATTT
ATGGCTATGGGCAACACATAATCCTAGTGCAATATGATACTGGGGTTATTAAGATGTGTCCCAGGCAGGGACCAAGACAG
GTGAACCATGTTGTTACACTCTATTTGTAACAAGGGGAAAGAGAGTGGACGCCGACAGCAGCGGACTCCACTGGTTGTCT
CTAACACCCCCGAAAATTAAACGGGGCTCCACGCCAATGGGGCCCATAAACAAAGACAAGTGGCCACTCTTTTTTTTGAA
ATTGTGGAGTGGGGGCACGCGTCAGCCCCCACACGCCGCCCTGCGGTTTTGGACTGTAAAATAAGGGTGTAATAACTTGG
CTGATTGTAACCCCGCTAACCACTGCGGTAGAACCACTTGCCCACAAAACCACTAATGGCACCCCGGGGAATACCTGCAT
ATGCTATCCTAATCTATATCTGGGTAGTATATGCTATCCTAATTTATATCTGGGTAGCATAGGCTATCCTAATCTATATC
TGGGTAGCATATGCTATCCTAATCTATATCTGGGTAGTATATGCTATCCTAATCTGTATCCGGGTAGCATATGCTATCCT
AATAGAGATTAGGGTAGTATATGCTATCCTAATTTATATCTGGGTAGCATATACTACCCAAATATCTGGATAGCATATGC
TATCCTAATCTATATCTGGGTAGCATATGCTATCCTAATCTATATCTGGGTAGCATAGGCTATCCTAATCTATATCTGGG
TAGCATATGCTATCCTAATCTATATCTGGGTAGTATATGCTATCCTAATTTATATCTGGGTAGCATAGGCTATCCTAATC
TATATCTGGGTAGCATATGCTATCCTAATCTATATCTGGGTAGTATATGCTATCCTAATCTGTATCCGGGTAGCATATGC
TATCCTCATGCATATACAGTCAGCATATGATACCCAGTAGTAGAGTGGGAGTGCTATCTCTTTGCATATGCCGCCACCTCC
CAAGGGGGCGTGAATTTTCGCTGCTTGTCCTTTTCCTGCGGTTGCTCCACCATTCTTAGGTGAATTTAAGGAGGCCAGGCT
AAAGCCGTCGCATGTCTGATTGCTCACCAGGTAAATGTCGCTAATGTTTTCCAACGCGAGAAGGTGTTGAGCGCGGAGCT
GAGTGACGTGACAACATGGGTATGCCCAATTGCCCCATGTTGGGAGGACGAAAATGGTGACAAGACAGATGGCCAGAAAT
ACACCAACAGCACGCATGATGTCTACTGGGGATTTATTCTTTAGTGCGGGGGAATACACGGCTTTTAATACGATTGAGGG
CGTCTCCTAACAAGTTACATCACTCCTGCCCTTCCTCACCCTCATCTCCATCACCTCCTTCATCTCCGTCATCTCCGTCA
TCACCCTCCGCGGACCCCTTCCACCATGAGGTGGAAACAGGGAGGGCAAATCTACTCCATCGTCAAAGCTGCACACAGT
CACCCTGATATTGCAGGTAGGAGCGGGCTTTGTCATAACAAGGTCCTTAATCGATCCTTCAAAACCTCAGCAAATATAT
GAGTTTGTAAAAAGACCATGAAATAACAGACAATGGACTCCCTTAGCGGGCCAGGTTGTGGGCCGGGTCCAGGGGCCATT
CCAAAGGGGAGACGACTCAATGGTGTAAGACGACATTGTGGAATAGCAAGGGCAGTTCCTCGCCTTAGGTTGTAAAGGGA
GGTCTTACTACCTCCATATACGAACACACCGGCGACCCAAGTTCCTTCGTCGGTAGTCCTTTCTACGTGACTCCTAGCCA
GGAGAGCTCTTAAACCTTCTGCAATGTTCTCAAATTTCGGGTTGGAACCTCCTTGACCACGATGCTTTCCAAACCACCCT
CCTTTTTTGCGCTGCCTCCATCACCCTGACCCCGGGGTCCAGTGCTTTGGGCTTTCTCCTTGGGTCATCTGCGGGGCCCTG
CTCTATCGCTCCCGGGGCACGTCAGGCTCACCATCTGGGCACCTTCTTGGTGGTATTCAAAATAATCGGCTTCCCCTA
CAGGGTGGAAAAATGGCCTTCTACCTGGAGGGGCCTGCGCGGTGGAGACCGGATGATGATGACTGACTACTGGGACTC
CTGGGCCTCTTTTCTCCACGTCCACGACCTCTCCCCCTGGCTCTTTCACGACTTCCCCCCTGGCTCTTTCACGTCCTCT
ACCCCGGCGGCCTCCACTACCTCCTCGACCCCGGCCTCCACTACCTCCTCGACCCCGGCCTCCACTGCCTCCTCGACCCC
GGCCTCCACCTCCTGCTCCTGCCCCTCCTGCTCCTGCCCCTCCTCCTGCTCCTGCCCCTCCTGCCCCTCCTGCTCCTGCC
CTCCTGCCCCTCCTGCTCCTGCCCCTCCTGCCCCTCCTGCTCCTGCCCCTCCTGCCCCTCCTGCTCCTGCCCCTCCTGCCC
CTCCTGCTCCTGCCCCTCCTGCTCCTGCCCCTCCTGCTCCTGCCCCTCCTGCTCCTGCCCCTCCTGCCCCTCCTGCCCCT
CCTCCTGCTCCTGCCCCTCCTGCTCCTGCCCCTCCTGCCCCTCCTGCCCCTCCTGCTCCTGCCCCTCCTCCTGCTCCTGC
CCCTCCTGCCCCTCCTCCTGCTCCTGCCCCTCCTGCCCCTCCTCCTGCTCCTGCCCCTCCTGCCCCTCCTCCTGCTCCTG
```

Figure 3F pCEP4 DNA sequence (continued):

```
CCCCTCCTGCCCCTCCTGCCCCTCCTCCTGCTCCTGCCCCTCCTGCCCCTCCTCCTGCTCCTGCCCCTCCTCCTGCTCCT
GCCCCTCCTGCCCCTCCTGCCCCTCCTCCTGCTCCTGCCCCTCCTCCTGCTCCTGCCCCTCCTGCCCCTCCTGCCCCTCC
TGCCCCTCCTCCTGCTCCTGCCCCTCCTCCTGCTCCTGCCCCTCCTGCTCCTGCCCCTCCCGCTCCTGCTCCTGCTCCTG
TTCCACCGTGGGTCCCTTTGCAGCCAATGCAACTTGGACGTTTTTGGGGTCTCCGGACACCATCTCTATGTCTTGGCCCT
GATCCTGAGCCGCCCCGGGGCTCCTGGTCTTCCGCCTCCTCGTCCTCGTCCTCTTCCCCGTCCTCGTCCATGGTTATCACC
CCCTCTTCTTTGAGGTCCACTGCCGCCGGAGCCTTCTGGTCCAGATGTGTCTCCCTTCTCTCCTAGGCCATTTCCAGGTC
CTGTACCTGGCCCCTCGTCAGACATGATTCACACTAAAGAGATCAATAGACATCTTTATTAGACGACGCTCAGTGAATA
CAGGGAGTGCAGACTCCTGCCCCCTCCAACAGCCCCCCACCCTCATCCCCTTCATGGTCGCTGTCAGACAGATCCAGGT
CTGAAAATTCCCCATCCTCCGAACCATCCTCGTCCTCATCACCAATTACTCGCAGCCCGGAAAACTCCCGCTGAACATCC
TCAAGATTTGCGTCCTGAGCCTCAAGCCAGGCCTCAAATTCCTCGTCCCCCTTTTTGCTGGACGGTAGGGATGGGGATTC
TCGGGACCTCCTCTTCCTCTTCAAGGTCACCAGACAGAGATGCTACTGGGGCAACGGAAGAAAAGCTGGGTGCGGCCT
GTGAGGATCAGCTTATCGATGATAAGCTGTCAAACATGAGAATTCTTGAAGACGAAAGGGCCTCGTGATACGCCTATTTT
TATAGGTTAATGTCATGATAATAATGGTTTCTTAGACGTCAGGTGGCACTTTTCGGGGAAATGTGCGCGGAACCCCTATT
TGTTTATTTTTCTAAATACATTCAAATATGTATCCGCTCATGAGACAATAACCCTGATAAATGCTTCAATAATATTGAAA
AAGGAAGAGTATGAGTATTCAACATTTCCGTGTCGCCCTTATTCCCTTTTTTGCGGCATTTTGCCTTCCTGTTTTTGCTC
ACCCAGAAACGCTGGTGAAAGTAAAAGATGCTGAAGATCAGTTGGGTGCACGAGTGGGTTACATCGAACTGGATCTCAAC
AGCGGTAAGATCCTTGAGAGTTTTCGCCCCGAAGAACGTTTTCCAATGATGAGCACTTTTAAAGTTCTGCTATGTGGCGC
GGTATTATCCCGTGTTGACGCCGGGCAAGAGCAACTCGGTCGCCGCATACACTATTCTCAGAATGACTTGGTTGAGTACT
CACCAGTCACAGAAAAGCATCTTACGGATGGCATGACAGTAAGAGAATTATGCAGTGCTGCCATAACCATGAGTGATAAC
ACTGCGGCCAACTTACTTCTGACAACGATCGGAGGACCGAAGGAGCTAACCGCTTTTTTGCACAACATGGGGGATCATGT
AACTCGCCTTGATCGTTGGGAACCGGAGCTGAATGAAGCCATACCAAACGACGAGCGTGACACCACGATGCCTGCAGCAA
TGGCAACAACGTTGCGCAAACTATTAACTGGCGAACTACTTACTCTAGCTTCCCGGCAACAATTAATAGACTGGATGGAG
GCGGATAAAGTTGCAGGACCACTTCTGCGCTCGGCCCTTCCGGCTGGCTGGTTTATTGCTGATAAATCTGGAGCCGGTGA
GCGTGGGTCTCGCGGTATCATTGCAGCACTGGGGCCAGATGGTAAGCCCTCCCGTATCGTAGTTATCTACACGACGGGGA
GTCAGGCAACTATGGATGAACGAAATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGATCTAGGTGAAGATCCTTTTTGA
TAATCTCATGACCAAAATCCCTTAACGTGAGTTTTCGTTCCACTGAGCGTCAGACCCCGTAGAAAAGATCAAAGGATCTT
CTTGAGATCCTTTTTTTCTGCGCGTAATCTGCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGCGCAGATACCAAATACTGTCCTTCTAGTGTA
GCCGTAGTTAGGCCACCACTTCAAGAACTCTGTAGCACCGCCTACATACCTCGCTCTGCTAATCCTGTTACCAGTGGCTG
CTGCCAGTGGCGATAAGTCGTGTCTTACCGGGTTGGACTCAAGACGATAGTTACCGGATAAGGCGCAGCGGTCGGGCTGA
ACGGGGGGTTCGTGCACACAGCCCAGCTTGGAGCGAACGACCTACACCGAACTGAGATACCTACAGCGTGAGCTATGAGA
AAGCGCCACGCTTCCCGAAGGGAGAAAGGCGGACAGGTATCCGGTAAGCGGCAGGGTCGGAACAGGAGAGCGCACGAGGG
AGCTTCCAGGGGGAAACGCCTGGTATCTTTATAGTCCTGTCGGGTTTCGCCACCTCTGACTTGAGCGTCGATTTTTGTGA
TGCTCGTCAGGGGGCGGAGCCTATGGAAAAACGCCAGCAACGCGGCCTTTTTACGGTTCCTGGCCTTTTGCTGGCCTTG
AAGCTGTCCCTGATGGTCGTCATCTACCTGCCTGGACAGCATGGCCTGCAACGCGGGCATCCCGATGCCGCCGGAAGCGA
GAAGAATCATAATGGGGAAGGCCATCCAGCCTCGCGTCGCGAACGCCAGCAAGACGTAGCCCAGCGCGTCGGCCCCGAGA
TGCGCCGCGTGCGGCTGCTGGAGATGGCGGACGCGATGGATATGTTCTGCCAAGGGTTGGTTTGCGCATTCACAGTTCTC
CGCAAGAATTGATTGGCTCCAATTCTTGGAGTGGTGAATCCGTTAGCGAGGTGCCGCCGGCTTCATCCCCGTGGCCCGT
TGCTCGCGTTTGCTGGCGGTGTCCCCGGAAGAAATATATTTGCATGTCTTTAGTTCTATGATGACACAAACCCCGCCCAG
CGTCTTGTCATTGGCGAATTCGAACACGCAGATGCAGTCGGGGCGGCGCGGTCCGAGGTCCACTTCGCATATTAAGGTGA
CGCGTGTGGCCTGGAACGCCGGACGCCCTGCAGCGACCCGCTTAACAGCGTCAACAGCGTGCCGCAGATCCCGGGGGC
AATGAGATATGAAAAGCCTGAACTCACCGCGACGTCTGTCGAGAAGTTTCTGATCGAAAAGTTCGACAGCGTCTCCGAC
CTGATGCAGCTCTCGGAGGGCGAAGAATCTCGTGCTTTCAGCTTCGATGTAGGAGGGCGTGGATATGTCCTGCGGGTAAA
TAGCTGCGCCGATGGTTTCTACAAAGATCGTTATGTTTATCGGCACTTTGCATCGGCCGCGCTCCCGATTCCGGAAGTGC
TTGACATTGGGGAATTCAGCGAGAGCCTGACCTATTGCATCTCCCGCCGTGCACAGGGTGTCACGTTGCAAGACCTGCCT
GAAACCGAACTGCCCGCTGTTCTGCAGCCGGTCGCGGAGGCCATGGATGCGATCGCTGCGGCCGATCTTAGCCAGACGAG
CGGGTTCGGCCCATTCGGACCGCAAGGAATCGGTCAATACACTACATGGCGTGATTTCATATGCGCGATTGCTGATCCCC
ATGTGTATCACTGGCAAACTGTGATGGACGACACCGTCAGTGCGTCCGTCGCGCAGGCTCTCGATGAGCTGATGCTTTGG
GCCGAGGACTGCCCCGAAGTCCGGCACCTCGTGCACGCGGATTTCGGCTCCAACAATGTCCTGACGGACAATGGCCGCAT
AACAGCGGTCATTGACTGGAGCGAGGCGATGTTCGGGGATTCCCAATACGAGGTCGCCAACATCTTCTTCTGGAGGCCGT
GGTTGGCTTGTATGGAGCAGCAGACGCGCTACTTCGAGCGGAGGCATCCGGAGCTTGCAGGATCGCCGCGGCTCCGGGCG
TATATGCTCCGCATTGGTCTTGACCAACTCTATCAGAGCTTGGTTGACGGCAATTTCGATGATGCAGCTTGGGCGCAGGG
TCGATGCGACGCAATCGTCCGATCCGGAGCCGGGACTGTCGGGCGTACACAAATCGCCCGCAGAAGCGCGGCCGTCTGGA
CCGATGGCTGTGTAGAAGTACTCGCCGATAGTGGAAACCGACGCCCCAGCACTCGTCCGGATCGGGAGATGGGGGAGGCT
AACTGAAACACGGAAGGAGACAATACCGGAAGGAACCCGCGCTATGACGGCAATAAAAAGACAGAATAAAACGCACGGGT
GTTGGGTCGTTTGTTCATAAACGCGGGGTTCGGTCCCAGGGCTGGCACTCTGTCGATACCCCACCGAGACCCCATTGGGG
CCAATACGCCCGCGTTTCTTCCTTTTCCCCACCCCACCCCCCAAGTTCGGGTGAAGGCCCAGGGCTCGCAGCCAACGTCG
GGGCGGCAGGCCCTGCCATAGCCACTGGCCCCGTGGGTTAGGGACGGGGTCCCCCATGGGGAATGGTTTATGGTTCGTGG
GGGTTATTATTTTGGGCGTTGCGTGGGGTCAGGTCCACGACTGGGCAGCAGACAGCCCATTGGTTTTTGGATGGCCTG
GGCATGGACCGCATGTACTGGCGCGACACGAACACGGGCGTCTGTGGCTGCCAAACACCCCCGACCCCAAAAACCACC
GCGCGGATTTCTGGCGTGCCAAGCTAGTCGACCAATTCTCATGTTTGACAGCTTATCATCGCAGATCCGGGCAACGTTGT
TGCCATTGCTGCAGGCGCAGAACTGGTAGGTATGGAAGATCTATACATTGAATCAATATTGGCAATTAGCCATATTAGTC
ATTGGTTATATAGCATAAATCAATATTGGCTATTGGCCATTGCATACGTTGTATCTATATCATAATATGTACATTTATAT
TGGCTCATGTCCAATATGACCGCCAT
```

Figure 3G

DNA sequence for Epstein Barr virus origin of replication (OriP) in pCEP-4 and Vectors N1-7 (SEQ ID NO.: 11):

```
caggaaaaggacaagcagcgaaaattcatgccccttgggaggtggcggcatatgcaaaggatagcactcccactctact
actgggtatcatatgctgactgtatatgcatgaggatagcatatgctacccggatacagattaggatagcatatactacc
cagatatagattaggatagcatatgctacccagatatagattaggatagcctatgctacccagatataaattaggatagc
atatactaccagatatagattaggatagcatatgctacccagatatagattaggatagcctatgctacccagatataga
ttaggatagcatatgctacccagatatagattaggatagcatatgctatccagatatttgggtagtatatgctacccaga
tataaattaggatagcatatactaccctaatctctattaggatagcatatgctacccggatacagattaggatagcatat
actaccagatatagattaggatagcatatgctacccagatatagattaggatagcctatgctacccagatataaattag
gatagcatatactaccagatatagattaggatagcatatgctacccagatatagattaggatagcctatgctacccaga
tatagattaggatagcatatgctatccagatatttgggtagtatatgctacccatggcaacattagccaccgtgctctc
agcgacctcgtgaatatgaggaccaacaaccctgtgcttggcgctcaggcgcaagtgtgtgtaatttgtcctccagatcg
cagcaatcgcgcccctatcttggcccgcccacctacttatgcaggtattccccggggtgccattagtggttttgtgggca
agtggtttgaccgcagtggttagcggggttacaatcagccaagttattacaccttattttacagtccaaaaccgcaggg
cggcgtgtggggctgacgcgtgccccactccacaatttcaaaaaaaagagtggccacttgtctttgtttatgggcccc
attggcgtggagcccgtttaattttcggggtgttagagacaaccagtggagtccgctgctgtcggcgtccactctctt
tccccttgttacaaatagagtgtaacaacatggttcacctgtcttggtcctgcctgggacacatcttaataacccagt
atcatattgcactaggattatgtgttgccatagccataaattcgtgtgagatggacatccagtcttacggcttgtccc
caccccatggatttctattgttaaagatattcagaatgtttcattcctacactagtatttattgcccaagggtttgtga
gggttatattggtgtcatagcacaatgccaccactgaaccccgtccaaatttattctggggcgtcacctgaaacct
tgtttcgagcacctcacatacaccttactgttcacaactcagcagttattctattagctaaacgaaggagaatgaagaa
gcaggcgaagattcaggagagttcactgcccgctccttgatcttcagccactgcccttgtgactaaaatggttcactacc
ctcgtggaatcctgaccccatgtaaataaaaccgtgacagctcatggggtgggagatatcgctgttccttaggacccttt
tactaaccctaattcgatagcatatgcttcccgttgggtaacatatgctattgaattagggttagtctggatagtatata
ctactacccgggaagcatatgctacccgtt
```

DNA sequence for SV40 poly-adenylation sequence represented in pCEP-4 and Vectors N1-7 (SEQ ID NO.: 19):

```
GGTGTGGAAAGTCCCCAGGCTCCCCAGCAGGCAGAAGTATGCAAAGCATGCATCTCAATTAGTCAGCAACCAGGTGTGGA
AAGTCCCCAGGCTCCCCAGCAGGCAGAAGTATGCAAAGCATGCATCTCAATTAGTCAGCAACCATAGTCCCGCCCCTAAC
TCCGCCCATCCCGCCCCTAACTCCGCCCAGTTCCGCCCATTCTCCGCCCCATGGCTGACTAATTTTTTTTATTTATGCAG
AGGCCGAGGCCGCCTCGGCCTCTGAGCTATTCCAGAAGTAGTGAGGAGGCTTTTTTGGAGGCCTAGGCTTTTGCAAA
```

DNA sequence for p53 from mouse (SEQ ID NO.: 13):

```
atgactgccatggaggagtcacagtcggatatcagcctcgagctccctctgagccaggagacattttcaggcttatggaa
actacttcctccagaagatatcctgccatcacctcactgcatggacgatctgttgctgccccaggatgttgaggagtttt
ttgaaggcccaagtgaagcctccgagtgtcaggagctcctgcagcacaggacccctgtcaccgagaccctgggccagtg
gcccctgccccagccactccatggcccctgtcatctttgtccttctcaaaaaacttaccagggcaactatggcttcca
cctgggcttcctgcagtctgggacagccaagtctgttatgtgcacgtactctcctcccctcaataagctattctgccagc
tggcgaagacgtgccctgtgcagttgtgggtcagcgccacacctcagctgggagccgtgtccgcgccatggccatctac
aagaagtcacagcacatgacggaggtcgtgagacgctgccccaccatgagcgctgctccgatggtgatggcctggctcc
tccctagcatcttatccggtggaaggaaatttgtatcccgagtatctggaagacaggcagactttcgccacagcgtgg
tggtaccttatgagccaccgaggccggctctgagtataccaccatccactcaagtacatgtgtaatagcctcctgcatg
ggggcatgaaccgccgacctatccttaccatcatcacactggaagactccagtgggaaccttctgggacgggacagctt
tgaggttcgtgtttgtgcctgccctgggagagaccgccgtacagaagaagaaatttcgcaaaaaggaagtcctttgcc
ctgaactgccccagggagcgcaaagagagcgctgcccaccttgcacaagcgctctccccgcaaaagaaaaaccactt
gatggagagtatttcaccctcaagatccgcgggcgtaaacgcttcgagatgttccgggagctgaatgaggccttagagtt
aaaggatgcccatgctacagaggagtctggagacagcagggctcactccagctacctgaagaccaagaagggccagtcta
cttcccgccataaaaaacaatggtcaagaaagtggggcctgactcagactga
```

Amino acid sequence for p53 from mouse (SEQ ID NO.: 14):

```
MTAMEESQSDISLELPLSQETFSGLWKLLPPEDILPSPHCMDDLLLPQDVEEFFEGPSEALRVSGAPAAQDPVTETPGPV
APAPATPWPLSSFVPSQKTYQGNYGFHLGFLQSGTAKSVMCTYSPPLNKLFCQLAKTCPVQLWVSATPPAGSRVRAMAIY
KKSQHMTEVVRRCPHHERCSDGDGLAPPQHLIRVEGNLYPEYLEDRQTFRHSVVVPYEPPEAGSEYTTIHYKYMCNSSCM
GGMNRRPILTIITLEDSSGNLLGRDSFEVRVCACPGRDRRTEEENFRKKEVLCPELPPGSAKRALPTCTSASPPQKKKPL
DGEYFTLKIRGRKRFEMFRELNEALELKDAHATEESGDSRAHSSYLKTKKGQSTSRHKKTMVKKVGPDSD
```

Figure 5A          Figure 5B          Figure 5C
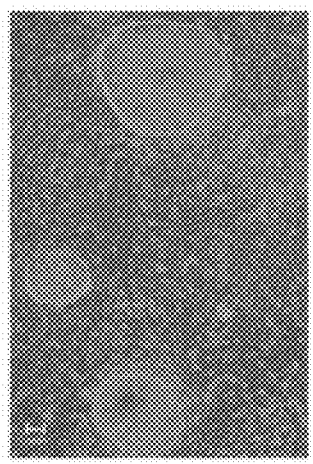 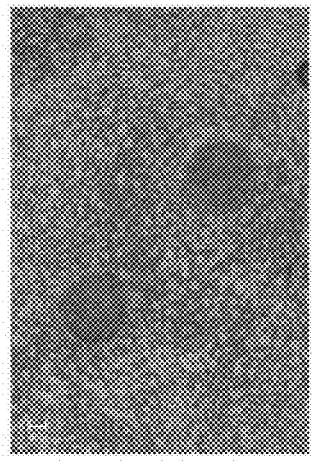 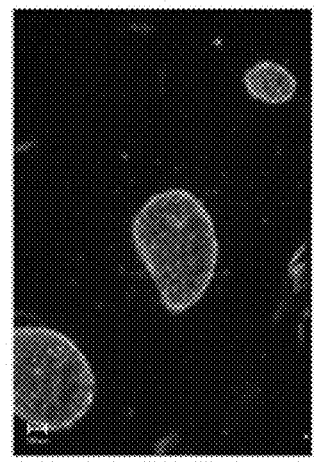
Figure 5D
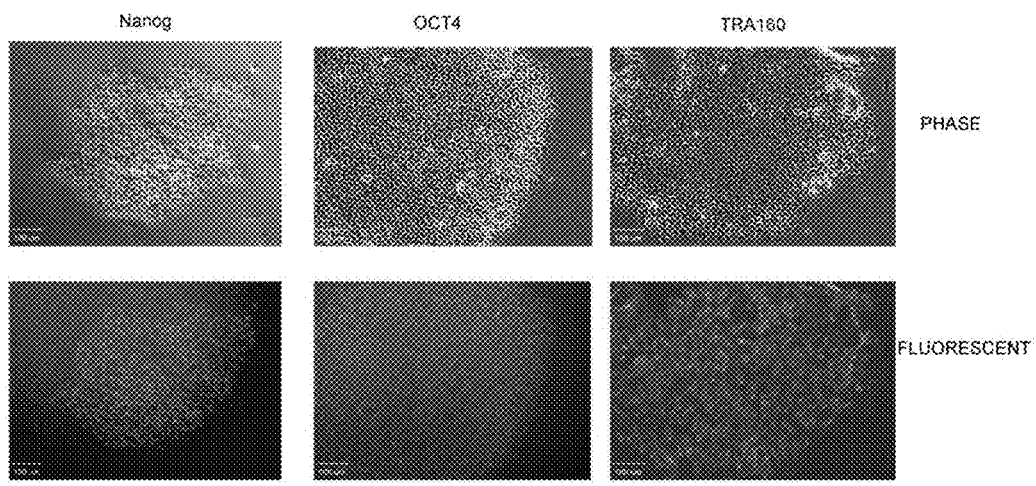

METHODS FOR CREATING INTEGRATION-FREE, VIRUS-FREE, EXOGENOUS ONCOGENE-FREE IPS CELLS AND COMPOSITIONS FOR USE IN SUCH METHODS

SEQUENCE LISTING

The instant application contains a Sequence Listing which has been submitted electronically in ASCII format and is hereby incorporated by reference in its entirety. Said ASCII copy, created on Mar. 23, 2018, is named P53616_SL.txt and is 62,299 bytes in size.

BACKGROUND OF THE INVENTION

Chronic disease from degenerative organ dysfunction accounts for eighty-six percent of the United States' healthcare cost. Stem cell therapy represents a potential solution to fill the gap of limited organ donations at a decreased cost. Stem cell therapy also has potential use in cancer vaccine formulations. Human embryo-derived stem cells (ESC) exhibit a neoplastic propensity when terminally differentiated cell cultures contain any undifferentiated cells. Further, tissue derived from ESCs, when transplanted, have a risk of graft rejection from human leukocyte antigen (HLA) mismatch between donor and recipient. There have, thus, been efforts to develop alternative pluripotent stem cells that lack immunogenicity, tumorigenicity, and ethical controversies inherent with ESCs. Induced pluripotent stem cells (IPSCs) represent a source of pluripotent stem cells that could achieve these objectives.

To derive IPSCs historically, somatic cells were transfected with reprogramming molecules using retroviral delivery systems. However, retroviral transfection introduces exogenous DNA into the genome, disrupting genes, and thus increasing the risk of neoplastic effects and teratoma formation. Additionally, known retroviral methods require transfection of oncogenes c-Myc, L-Myc, and/or Lin-28. Lin28, c-Myc, and L-Myc are associated with several clinical malignancies and may increase the risk of neoplastic effects and teratoma formation long-term.

Episomal reprogramming is an ideal method for creating clinical-grade, safer, non-viral and integration-free IPSCs. Exogenous genes introduced through episomal vectors can be easily monitored through fluorescent tags such as Red Fluorescent Protein and their shut down can be easily detected. Unlike other methodologies, episomal vectors are only active on average for 17 to 21 days before reaching an undetectable level due to dilution and instability caused by cell division. However, episomal reprogramming has often been avoided since the reprogramming efficiency has been very low compared to other non-viral methods. To compensate for the lower reprogramming efficiency, episomal constructs comprising oncogenes such as c-Myc or a combination of L-Myc and Lin28 have been used. Even then, no IPSC colony formation was observed using an episomal reprogramming strategy that delivered the combination of Oct4, Sox2, Nanog, Lin28, c-Myc and Klf4. Only after the addition of a SV40 large T antigen gene to the combination of Oct4, Sox2, Nanog, Lin28, c-Myc and Klf4 genes could colony formation be observed with episomal delivery and, even then, the reprogramming efficiency was only approximately 0.0006 percent. However, SV40 large T antigen when introduced to cells can also immortalize them. SV40 large T antigen, when expressed, can also induce a malignant transformation, teratoma formation, and/or neoplasticity in a variety of cell lines. Others had avoided the use of SV40 large T antigen by adding NANOG, Lin28, and c-Myc with Oct-3/4 Klf4, and Sox-2, or by adding NANOG, Lin28, and L-Myc with Oct-3/4 Klf4, and Sox-2 and suppressing tumor checkpoint protein p53. Like SV40 large T antigen, Nanog is overexpressed in cancer cells. Mice which overexpress Nanog have hyperplastic outgrowths in the intestinal and colonic epithelium and the stratified epithelium of the caudal stomach and esophagus, and when co-expressed with Wnt-1, breast cancer tumors including metastasis. The additional requirements of oncogenes such as c-Myc, L-Myc, Lin-28, and Nanog represent a barrier to clinical use of the reprogrammed cells because the presence of the oncogenes in the reprogramming method, for however long, could increase the likelihood of a neoplastic event, teratoma formation, and cancer when the IPSCs or cells differentiated from IPSCs are transplanted into an organism.

There remains a need for alternative reprogramming methods and safer, more efficient methods for producing induced pluripotent stem cells from somatic cells.

SUMMARY OF THE INVENTION

Herein provided is a method for reprogramming a somatic cell comprising: (i) expressing exogenous Sox-2, Klf-4, and Oct3/4 in the somatic cell from DNA that has not integrated into genomic DNA of the somatic cell; inhibiting p53 activity in the somatic cell; and culturing the somatic cell in a reprogramming medium comprising an exogenous Alk-5 inhibitor, an exogenous histone deacetylase inhibitor, and an exogenous activator of glycolysis.

In an embodiment, the method for reprogramming a somatic cell, further comprises expressing exogenous EBNA-1 in the somatic cell from DNA that has not integrated into the genomic DNA of the somatic cell, and the DNA that has not integrated into the genomic DNA of the somatic cell comprises at least one plasmid with an Epstein-Barr virus origin of replication (oriP).

In an embodiment, also provided is such a method for reprograming a somatic cell, wherein one or more of L-Myc, c-Myc, Lin28, SV 40 large T antigen, and Nanog are not exogenously expressed.

In an embodiment, the method for reprogramming a somatic cell further comprises maintaining the cell in a dedifferentiation maintenance medium comprising basic fibroblast growth factor and transforming growth factor beta after being cultured in the reprogramming medium.

In an embodiment, the method for reprogramming a somatic cell involves a method as described above wherein the culturing which does not require feeder cells.

In an embodiment, the method for reprogramming a somatic cell has a reprogramming efficiency that exceeds 0.0006%.

In an embodiment, provided herein is a method for reprogramming a somatic cell, wherein inhibiting p53 activity in the somatic cell inhibits p53-induced cell cycle arrest or p53-induced apoptosis.

In an embodiment of the method for reprograming a somatic cell, inhibiting p53 activity in the somatic cell comprises suppressing p53 expression in the somatic cell.

In an embodiment of the method for reprograming a somatic cell, suppressing p53 expression comprises expressing antisense p53 RNA in the somatic cell from DNA that has not integrated into the genomic DNA of the somatic cell.

In an embodiment of the method for reprogramming a somatic cell, the Alk-5 inhibitor comprises 3-(6-Methyl-2-pyridinyl)-N-phenyl-4-(4-quinolinyl)-1H-pyrazole-1-carbothioamide (A83-01), the histone deacetylase inhibitor comprises sodium butyrate or valproic acid, and the activator of glycolysis comprises a phosphoinositide-dependent protein kinase-1 inhibitor selected from 5-(4-Chloro-phenyl)-3-phenyl-pent-2-enoic acid (PS48); α,α,-Dimethyl-4-[2-methyl-8-[2-(3-pyridinyl)ethynyl]-1H-imidazo[4,5-c]quinolin-1-yl]-benzeneacetonitrile (BAG956); N-[3-[[5-Iodo-4-[[3-(2-thienylcarbonyl)amino]propyl]amino]-2-pyrimidinyl]amino]phenyl]-1-pyrrolidinecarboxamide (BX795); (3S,6R)-1-[6-(3-Amino-1H-indazol-6-yl)-2-(methylamino)-4-pyrimidinyl]-N-cyclohexyl-6-methyl-3-piperidinecarboxamide (GSK 2334470); 2-Amino-N-[4-[5-(2-phenanthrenyl)-3-(trifluoromethyl)-1H-pyrazol-1-yl]phenyl]acetamide (OSU03012); and 4-Dodecyl-N-1,3,4-thiadiazol-2-yl-benzenesulfonamide (PHT427).

In an embodiment of the method for reprogramming a somatic cell, the somatic cell is an isolated cord blood or peripheral blood mononuclear cell, and the method further comprises pre-culturing the isolated cord blood or peripheral blood mononuclear cell in hematopoietic stem cell expansion media.

In an embodiment, the method for reprogramming a somatic cell yields an integration-free, virus-free, exogenous oncogene-free IPS cell.

Also provided herein is a method as described above in which the iPS cell is a human iPS cell.

Also provided herein is a method as described above wherein the iPS cell is differentiated into an endodermal, mesodermal, or ectodermal cell.

In an embodiment, also provided is a method for reprogramming a somatic cell comprising: expressing exogenous Sox-2, Klf-4, and Oct-3/4 in the somatic cell; suppressing p53 expression in the somatic cell; and culturing the somatic cell in a reprogramming medium comprising at least three different exogenous reprogramming-assistance factors to obtain an iPS cell free of exogenous oncogenes and exogenous viral elements.

In an embodiment, the method for reprogramming a somatic cell comprises expressing Sox-2, Klf-4, and Oct-3/4 in the somatic cell from episomal DNA.

In an embodiment, the method for reprogramming a somatic cell further comprises expressing EBNA-1 in the somatic cell and Sox-2, Klf-4, Oct-3/4, and EBNA-1 are expressed from at least one plasmid with an Epstein-Barr virus origin of replication (oriP).

Also described herein is a method for reprogramming a somatic cell as described above, wherein suppressing p53 expression in the somatic cell comprises expressing antisense p53 RNA in the somatic cell.

Herein also provided is a composition comprising a somatic cell and a cell culture medium, the somatic cell comprising episomal polynucleotides encoding EBNA-1, Sox-2, Klf-4, and Oct3/4, and the medium comprising an exogenous Alk-5 inhibitor, an exogenous histone deacetylase inhibitor, and an exogenous activator of glycolysis.

Herein also provided is a kit comprising (a) one or more non-integrating vectors encoding Sox-2, Klf-4, and Oct3/4; (b) an agent for inhibiting p53 activity; and (c) a reprogramming medium which comprises an Alk-5 inhibitor, a histone deacetylase inhibitor, and an activator of glycolysis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2. Exemplary combinations of vectors/reprogramming factors. FIG. 2 shows exemplary combinations of episomal vectors and reprogramming-assistance factors (PS48, A83-01, and sodium butyrate), used for somatic cell reprogramming Combinations were categorized into those containing exogenous L-Myc and Lin28, those free of exogenous Myc (i.e., free of exogenous c-Myc and L-Myc) and Lin28, and those comprising exogenous c-Myc.

FIGS. 3A-3G. Exemplary Polynucleotide and Amino Acid Sequences For Use in Methods as Disclosed Herein. FIG. 3A shows: Red Fluorescent Protein (RFP) DNA sequence inserted into pCEP-4 for Vector N1 (SEQ ID NO.: 15), Red Fluorescent Protein (RFP) amino acid sequence as translated from Vector N1 (SEQ ID NO.: 16), Human 1-Myc DNA sequence inserted into pCEP-4 for Vector N2 (SEQ ID NO.: 7), Human 1-Myc amino acid sequence as translated from Vector N2 (SEQ ID NO.: 8), and Human Lin28 DNA sequence inserted into pCEP-4 for Vector N2 (SEQ ID NO.: 5). FIG. 3B shows: Human Lin28 amino acid sequence as translated from Vector N2 (SEQ ID NO.: 6), Epstein-Barr virus nuclear antigen 1 (EBNA-1) DNA sequence inserted into pCEP-4 for Vector N3 (SEQ ID NO.: 21), EBNA-1 sequence as translated from Vector N3 (SEQ ID NO.: 22), and Human c-Myc DNA sequence inserted into pCEP-4 for Vector N4 (SEQ ID NO.: 1). FIG. 3C shows: Human c-Myc amino acid sequence as translated from Vector N4 (SEQ ID NO.: 2), Human Sox-2 DNA sequence inserted into pCEP-4 for Vector N5 (SEQ ID NO.: 17), Human Sox-2 amino acid sequence as translated from Vector N5 (SEQ ID NO.: 18), Human Klf-4 DNA sequence inserted into pCEP-4 for Vector N5 (SEQ ID NO.: 3), and Human Klf-4 amino acid sequence as translated from Vector N5 (SEQ ID NO.:4). FIG. 3D shows: DNA sequence encoding antisense RNA for p53 mRNA inserted into pCEP-4 for Vector N6 (SEQ ID NO.: 12), Oct-3/4 DNA sequence inserted into pCEP-4 for Vector N7 (SEQ ID NO.: 9), and Oct-3/4 amino acid sequence as translated from Vector N7 (SEQ ID NO.: 10). FIG. 3E shows the nucleotides 1-5040 of the pCEP4 DNA sequence (SEQ ID NO.: 20). FIG. 3F shows nucleotides 5041-10186 of the pCEP4 DNA sequence (SEQ ID NO.: 20). FIG. 3G shows: DNA sequence for Epstein Barr virus origin of replication (OriP) in pCEP-4 and Vectors N1-7 (SEQ ID NO.: 11), DNA sequence for SV40 poly-adenylation sequence represented in pCEP-4 and Vectors N1-7 (SEQ ID NO.: 19), DNA sequence for p53 from mouse (SEQ ID NO.: 13), and Amino acid sequence for p53 from mouse (SEQ ID NO.: 14).

FIG. 4 depicts the time line sequence of IPSC reprogramming and cell expansion.

FIGS. 5A-5D. Montage of Phase Contrast, Alkaline Phosphatase, Nanog, Oct4, Tra160. Montage of cultured human foreskin fibroblasts (HFFs) reprogrammed into IPSCs with episomal vectors free of Myc and Lin28 and IPSC reprogramming factors Images were captured at day 14 of the IPSC reprogramming process. FIG. 5A shows typical IPSC colonies depicted by phase contrast microscopy. FIG. 5B shows representative IPSC colonies stained for alkaline phosphatase. FIG. 5C shows representative IPSC colonies exhibit pluripotency by immunofluorescent live stain for SSEA4. Each figure is representative of 4 separate experiments. Scale bar represents 100 microns. FIG. 5D shows representative IPSC colonies depicted by phase microscopy with corresponding pluripotent fluorescent biomarker of Nanog, Oct4 and TRA160 of the same colony. Scale bar represents 100 microns.

FIG. 6A: Black arrows point to iPSC colonies captured under phase microscopy. FIG. 6B: White arrows point to the corresponding RFP signal in the same colonies. As shown there is a complete loss of expression of RFP in the IPSC colonies demonstrating that episomal vectors are shut down within 2 weeks. The figure is representative of 4 separate experiments. Scale bar represents 100 microns.

FIG. 7A illustrates the numbers of colonies generated between the different vector constructs among cultured cells reprogrammed in the presence of reprogramming-assistance factors. Data are reported as the mean (±SE) number of colonies observed for cultured HFF reprogrammed with 1-Myc/Lin28, c-Myc and in the absence of these oncogenes. Each test condition used 100,000 input cells. Each group represents a sample size of 4. FIG. 7B illustrates the number of colonies generated between the different vector constructs among cultured cells reprogrammed in the absence of reprogramming-assistance factors. Data are reported as the mean (±SE) number of colonies observed for cultured REF reprogrammed with 1-Myc/Lin28, c-Myc and in the absence of both oncogenes. Each group represented a sample size of 4. Data labeled with * show a statistical significant difference (p<0.05) between cultured cells treated with Myc and Lin28 and those cells treated without Myc and Lin28. NS denotes no significant difference.

FIG. 20A shows a dot blot of CD34+ and CD34− cell populations. FIG. 20B shows frequency of CD34+ cells across log fluorescence when CBDMCs were exposed to HSC differentiation media—13% of CBDMNC differentiated into CD34+ cells after 7 days of exposure to HSC differentiation media. FIG. 20C shows frequency of CD34+ cells across log fluorescence when CBDMCs were not exposed to HSC differentiation media—a mere 1% of CBDMCs differentiated into CD34+ cells in the absence of HSC differentiation media.

DETAILED DESCRIPTION OF THE INVENTION

Figure 1:
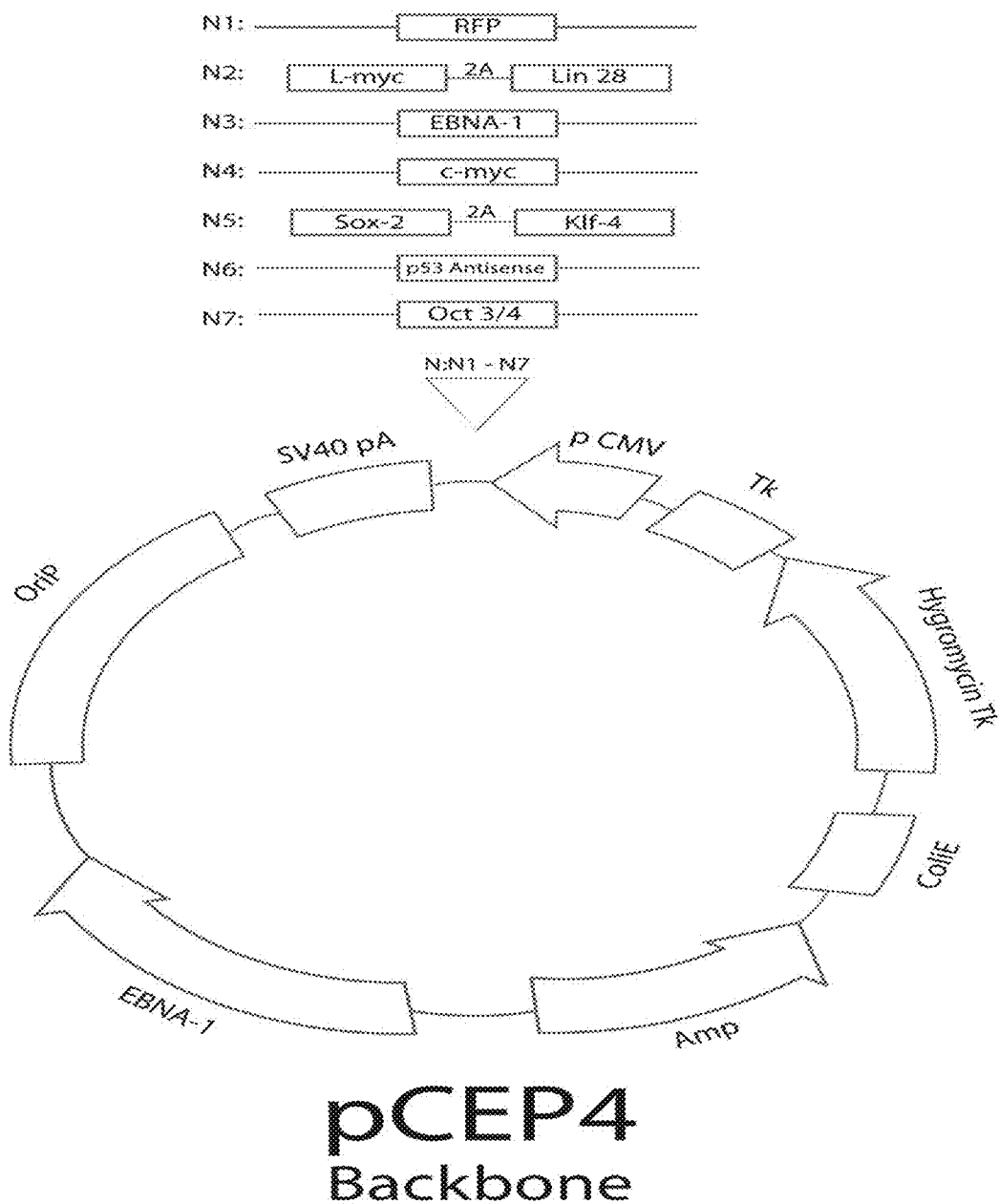
FIG. 1. Episomal vector design. A generalized vector map of an exemplary episomal vector based on the pCEP-4 episomal backbone containing an Epstein Barr virus origin of replication (OriP), SV40 poly-adenylation sequence, 2A cleavage sequence for tandem genes, a bacterial origin of replication, and ampicillin/hygromycin resistance genes is shown. As shown, each vector either contains a single gene or tandem genes separated by a 2A cleavage sequence.

The particulars shown herein are by way of example and for purposes of illustrative discussion of the various embodiments only and are presented in the cause of providing what is believed to be the most useful and readily understood description of the principles and conceptual aspects of the methods and compositions described herein. In this regard, no attempt is made to show more detail than is necessary for a fundamental understanding, the description making apparent to those skilled in the art how the several forms may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope to those skilled in the art.

Unless otherwise defined, all technical and scientific terms used herein have the same meaning as commonly understood by one of ordinary skill in the art to which this invention belongs. The terminology used in the description herein is for describing particular embodiments only and is not intended to be limiting. As used in the description and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Unless indicated to the contrary, the numerical parameters set forth in the following specification and attached claims are approximations that may vary depending upon the desired properties sought to be obtained and thus may be modified by the term "about". At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Advantages and Features

As described above, provided herein are methods for reprogramming a somatic cell comprising expressing exogenous Sox-2, Klf-4, and Oct3/4 in the somatic cell from DNA that has not integrated into genomic DNA of the somatic cell; inhibiting p53 activity in the somatic cell; and culturing the somatic cell in a reprogramming medium comprising, for example, an exogenous Alk-5 inhibitor, an exogenous histone deactylase inhibitor, and an exogenous activator of glycolysis. Methods for reprogramming a somatic cell as described herein do not require introduction of DNA that has integrated into the genomic DNA of the somatic cell insofar as the introduced DNA comprises at least one plasmid with an Epstein-Barr virus origin of replication (oriP). Another advantage is that methods for reprograming a somatic cell as described herein need not involve exogenously expressing one or more of Nanog, L-Myc, c-Myc, Lin28, and SV40 large T-antigen. Reprogramming may be further accomplished by maintaining the cell in a dedifferentiation maintenance medium, also known as an IPSC growth medium, comprising basic fibroblast growth factor and transforming growth factor beta after being cultured in the reprogramming medium.

Other features and advantages will be evident to those of skill in the art. For example, a method for reprogramming a somatic cell as described herein may include inhibiting p53 activity in the somatic cell to further inhibit p53-induced cell cycle arrest or p53-induced apoptosis. Methods as described herein also do not require feeder cells during culturing and may achieve reprogramming efficiencies that equal or exceed 0.0006%.

Methods for reprogramming a somatic cell as described herein further have the advantage that they may be applied to both adherent and non-adherent cells. When performed with a non-adherent cell, such as isolated cord blood or peripheral blood mononuclear cell, the method may comprise a pre-culturing step that comprises isolating the cord blood or peripheral blood mononuclear cell in hematopoietic stem cell expansion media.

The skilled artisan will further appreciate that methods for reprogramming a somatic cell as described herein may yield an integration-free, virus-free, exogenous oncogene-free iPS cell.

Initial Isolation of Cells, Initial Culturing are not Particularly Limited.

Somatic cells may be initially isolated and cultured to provide a starting material. The somatic cell is not particularly limited but it should preferably be isolated from a cell known to carry the full-genetic repertoire of the organism, such as a diploid cell, and should not be isolated from cells predisposed to having some or all of the genetic repertoire eliminated, such as cells from the gonads, red blood cells, and platelets. Cells with multiple nucleuses are not particularly preferred either, such as skeletal muscle cells, and some forms of white blood cells. Somatic cells can include adhesive and non-adhesive cells, cells of endodermal, ectodermal, or mesodermal origin. Somatic cells can include fibroblasts, endothelial cells, epidermal cells, lymphocytes, neurons, ependymal cells, oligodendrocytes, Schwann cells, astrocytes, glia, enterocytes, goblet cells, Paneth cells, parietal cells, pitt cells, gastric cells, chymogenic cells, enteroendocrine cells, alpha cells, beta cells, keratinocytes, submucosa cells, stromal cells, tenocytes, adipocytes, mast cells, macrophages, epithelial cells, basal cells, squamous epithelial cells, ondotoblasts, endodontium cells, osteoclasts, osteoblasts, myeloblasts, basophils, neutrophils, eosinophils, monocytes, plasma cells, B lymphocytes, T lymphocytes, natural killer cells, small lymphocytes, myelocytes, normoblasts, and myeloplaxe. In the event a progenitor cell is used, such as a common myeloid progenitor cell, a common lymphoid progenitor cell, or a neural progenitor cell, it may be necessary to differentiate the cell by exposing the cell in culture to differentiation factors before the reprogramming the somatic cell.

Generation of DNA that does not Integrate into the Genome Transfection

To reprogram the somatic cells, the cells may express Sox-2, Klf-4, and Oct3/4 proteins, and, preferably, Epstein-Barr nuclear antigen-1 (EBNA-1) protein from exogenous genetic material that has not integrated into the genome of the somatic cell. The proteins may be expressed at levels higher than those observed in a cell which has not been manipulated to express exogenous Sox-2, Klf-4, and Oct3/4 proteins but otherwise has undergone all the other treatments, such as suppression of p53 activity and growth in media containing reprogramming-assistance factors. The exogenous genetic material that has not integrated into the genome of the somatic cell includes, but is not limited to, DNA that has not integrated into the genome of the somatic cell, and such DNA can include, but is not limited to cell, and such DNA can include, but is not limited to plasmids. Preferably, the plasmids include an Epstein-Barr virus origin of replication (oriP) and/or a gene for EBNA-1 expression to further ensure that the plasmids do not integrate into the genome of the somatic cell. It is contemplated that Sox-2, Klf-4, Oct3/4, and optionally EBNA-1 and optionally other gene sequences coding for protein can be expressed on separate plasmids or DNA molecule or on the same plasmid or DNA molecule. Whether Sox-2, Klf-4, Oct3/4, and optionally EBNA-1, and optionally other gene sequences coding for protein are all expressed on one plasmid or DNA molecule, each individually on a separate plasmid or DNA molecule, or in some combination of two or more plasmids or DNA molecule (e.g. Klf-4 and Oct3/4 on the same plasmid, and Sox-2 and EBNA-1 on distinct plasmids or DNA molecule) depends upon the length of each protein coding sequence, the length of the overall plasmid or DNA molecule, and the method of transfection. For example, certain virion vectors for transfection can range from 4.7 to 8.7 kilo base pairs for AAV vectors, whereas herpes virus sequence can be 150 kilo base pairs. Likewise the optimal plasmid or DNA molecule lengths can vary from across non-viral vector methods of transfection such as nucleofection or lipofection protocols.

One particular embodiment of expressing exogenous Sox-2, Klf-4, Oct3/4 and optionally EBNA-1, can be through the transfection of one or more of plasmids, which contain the gene sequences for Sox-2 represented by SEQ ID NO: 17, Klf-4 represented by SEQ ID NO: 3, Oct3/4 represented by SEQ ID NO: 9, and optionally EBNA-1 represented by SEQ ID NO:21. In such an embodiment, the transfected somatic cell will express a Klf-4 protein of SEQ ID NO: 4, an Oct3/4 protein of SEQ ID NO: 10, a Sox-2 protein of SEQ ID NO: 18, and optionally an EBNA-1 protein of SEQ ID NO: 22_from the transfected incorporated plasmid. In one particular embodiment, the genes encoding for Sox-2, Klf-4, Oct-3/4, and EBNA-1 are incorporated into the pCEP-4 plasmid of SEQ ID NO: 20. In another particular embodiment, c-Myc, SEQ ID NO: 1 may be incorporated in the pCEP-4 plasmid of SEQ ID NO: 20 and the incorporated plasmid then may be transfected into the somatic cell. In such an embodiment, the transfected somatic cell will express c-Myc protein of SEQ ID NO: 2 from the transfected incorporated plasmid. In another particular embodiment, a Lin28 of SEQ ID NO: 5, and 1-Myc of SEQ ID NO: 7_may be incorporated in the pCEP-4 plasmid of SEQ ID NO: 20 and the incorporated plasmid may be then transfected into the somatic cell. In such an embodiment, the transfected somatic cell will express proteins of SEQ ID NO: 6, and SEQ ID NO: 8, respectively, from the transfected incorporated plasmid.

In an embodiment, an exemplary Sox-2 amino acid sequence may be an amino acid sequence which has at least 75%, 80%, 85%, 90%, 91%, 92%, 93%, 94%, 95%, 96%, 97%, 98%, or 99% identity to the Sox-2 amino acid sequence transcribed and translated from the somatic cell genome, and which is capable of functioning as a transcription factor within the cell. In an embodiment, an exemplary Sox-2 nucleotide sequence may be a nucleotide sequence which has at least 75%, 80%, 85%, 90%, 91%, 92%, 93%, 94%, 95%, 96%, 97%, 98%, or 99% identity to the Sox-2 nucleotide sequence of the somatic cell and which is capable of being transcribed and translated into a Sox-2 protein which is capable of functioning as a transcription factor within the cell.

In an embodiment, an exemplary Klf-4 amino acid sequence may be an amino acid sequence which has at least 75%, 80%, 85%, 90%, 91%, 92%, 93%, 94%, 95%, 96%, 97%, 98%, or 99% identity to the Klf-4 amino acid sequence transcribed and translated from the somatic cell genome, and which is capable of functioning as a transcription factor within the cell. In an embodiment, an exemplary Klf-4 nucleotide sequence may be a nucleotide sequence which has at least 75%, 80%, 85%, 90%, 91%, 92%, 93%, 94%, 95%, 96%, 97%, 98%, or 99% identity to the Klf-4 nucleotide sequence of the somatic cell and which is capable of being transcribed and translated into a Klf-4 protein which is capable of functioning as a transcription factor within the cell.

In an embodiment, an exemplary Oct3/4 amino acid sequence may be an amino acid sequence which has at least 75%, 80%, 85%, 90%, 91%, 92%, 93%, 94%, 95%, 96%, 97%, 98%, or 99% identity to the Oct-3/4 amino acid sequence transcribed and translated from the somatic cell genome, and which is capable of functioning as a transcription factor within the cell. In an embodiment, an exemplary Oct-3/4 nucleotide sequence may be a nucleotide sequence which has at least 75%, 80%, 85%, 90%, 91%, 92%, 93%, 94%, 95%, 96%, 97%, 98%, or 99% identity to the Oct-3/4 nucleotide sequence of the somatic cell and which is capable of being transcribed and translated into a Oct-3/4 protein which is capable of functioning as a transcription factor within the cell.

In an embodiment, an exemplary EBNA-1 amino acid sequence may be an amino acid sequence which has at least 75%, 80%, 85%, 90%, 91%, 92%, 93%, 94%, 95%, 96%, 97%, 98%, or 99% identity to the EBNA-1 as disclosed herein, and which is capable of maintaining episomal vector replication. In an embodiment, an exemplary EBNA-1 nucleotide sequence may be a nucleotide sequence which has at least 75%, 80%, 85%, 90%, 91%, 92%, 93%, 94%, 95%, 96%, 97%, 98%, or 99% identity to the EBNA-1 nucleotide sequence as disclosed herein and which is capable of being transcribed and translated into a EBNA-1 protein which is capable of functioning in episomal DNA maintenance during reprogramming.

It is further contemplated that the Oct3/4, Klf-4, and Sox-2 sequences of protein or nucleotides encoding protein can vary from species to species, and within species, and that the nucleotide and amino acid sequences are not limited to a particular sequence identified at the time of filing this application. It is further contemplated that the EBNA-1 sequences of protein or nucleotides encoding protein can vary from varieties of cytomegaloviruses, and that the nucleotide and amino acid sequences are not limited to a particular sequence explicitly disclosed herein. For example, Oct3/4, Klf-4, and Sox-2 polymorphisms identified in the human population, rat population, mouse population, or the population of other species are included herein. It is further preferred that when transfecting a somatic cell with DNA encoding for exogenous DNA, that the sequences of Oct3/4, Klf-4, and Sox-2 be selected from sequences identified from the same species as the somatic cell. It is further preferred that when transfecting a somatic cell with DNA encoding for exogenous Oct3/4, Klf-4, and Sox-2, that the sequences of Oct3/4, Klf-4, and Sox-2 be the same as that of the genome of somatic cell.

It is further contemplated that c-Myc, L-Myc, and/or Lin28 are also expressed from exogenous genetic material that has not integrated into the genome of the somatic cell. In some embodiments, L-Myc and Lin28 are co-expressed. It is preferred that the c-Myc, L-Myc, and/or Lin28 are expressed at levels higher than those observed in a cell which has not been manipulated to express exogenous c-Myc, L-Myc, and/or Lin28 proteins but otherwise has undergone all the other treatments, such as suppression of p53 activity and growth in media containing reprogramming-assistance factors.

It is further preferred that the somatic cell not be transfected to express exogenous SV 40 large T antigen.

Exogenous transfection may omit transfection of DNA encoding SV40 large T antigen and Nanog that does not integrate into the host cells' genome. It is further preferred that the exogenous transfection omit transfection of exogenous DNA that does not integrate into the host cell's genome and encodes c-Myc along with SV40 large T antigen and Nanog. It is further preferred that the exogenous transfection omit transfection of exogenous DNA that does not integrate into the host cell's genome and encodes L-Myc along with SV40 large T antigen and Nanog. It is further preferred that the exogenous transfection omit transfection of exogenous DNA that does not integrate into the host cell's genome and encodes Lin-28 along with SV40 large T antigen and Nanog. It is further preferred that the exogenous transfection omit transfection of exogenous DNA that does not integrate into the host cells' genome and encodes L-Myc and Lin-28 along with SV40 large T antigen and Nanog. It is further preferred that the exogenous transfection omit transfection of exogenous DNA that does not integrate into the host cells genome and encodes c-Myc, L-Myc and Lin-28 along with SV40 large T antigen and Nanog.

It is further contemplated that the expression is transient for the exogenous genes that have not integrated into the genome particularly when the genes are located within a plasmid with an OriP origin of replication, for example, as represented by SEQ ID NO: 11. Transient transfection may also be achieved by use of an inducible promoter, such as chemically-regulated promoters such as those regulated by the presence or absence of alcohol, tetracycline, steroids, or a metal; and physically-regulated promoters such as those regulated by the presence or absence of light or low or high temperatures. It is further contemplated that the expression of Oct-3/4, Klf-4, Sox-2, EBNA-1 c-Myc, 1-Myc, and/or Lin28 is/are transient. It is further contemplated that the transient expression of the exogenous genes that have not integrated into the genome, such as but not limited to Oct-3/4, Klf-4, Sox-2, EBNA-1 c-Myc, 1-Myc, and/or Lin28, lasts for 3-weeks, 17-days, or 2-weeks after the last transfection, if multiple transfections are attempted. It is further contemplated that the expression of the exogenous genes that have not integrated into the genome, such as but not limited to Oct-3/4, Klf-4, Sox-2, EBNA-1 c-Myc, 1-Myc, and/or Lin28, ceases after 3-weeks, 17-days, or 2-weeks after the last transfection, if multiple transfections are attempted. It is preferred that the expression ceases after 3-weeks. It is further preferred that the expression ceases after 17-days. It is further preferred that the expression ceases after 2-weeks. It is further preferred that the length of transient expression inversely correlate with the number of genes encoding for EBNA-1 that are transfected into the somatic cell.

Confirmation of Transfection of DNA that does not Integrate into the Genome is not Particularly Limited It is further contemplated that the plasmids contain genetic elements which can serve as markers for confirming that the plasmid has been transfected into the somatic cell. Such genetic elements which can serve as markers confirming transfection of the plasmid include, but are not limited to, incorporation of genes encoding for GFP, YFP, RFP, mCherry, dTomato, DsRed, Crimson, and other fluorescent proteins which may be expressed by the somatic cell after transfection. Non-fluorescent markers that confirm transfection of a plasmid are also contemplated. In one embodiment, the DNA sequence encoding for RFP, such as SEQ ID NO: 15, may be incorporated into the pCEP-4 plasmid of SEQ ID NO: 20, and the incorporated plasmid may be transfected into the somatic cell. In such an embodiment, the somatic cell may express the RFP protein of SEQ ID NO: 16 from the transfected incorporated plasmid.

Additionally, transfection can be confirmed by measuring expression of mRNA or protein for Sox-2, Klf-4, Oct-3/4 and/or EBNA-1. Additionally qPCR measurement of sequences in the plasmid can evaluate efficiency of transfection. The means of confirming transfection are thus not particularly limited.

The amount of plasmid transfected, in sum or for each individual plasmid, is not particularly limited. Several different amounts of plasmid may be tested and the amount of plasmid that results in the most or a substantial number of cells expressing the selected marker, such as RFP, may be used. In this instance, a substantial number of cells refers to the number of cells within one standard deviation of the maximal number of cells transfected and wherein the number of replicates within each condition is 6. The amount of plasmid may be either the total amount of all the plasmids, if Sox-2, Klf-4, Oct-3/4 and/or EBNA-1 are contained on two or more plasmids. The amount of plasmid transfected can be 0.5 µg, 1 µg, 2 µg, 3 µg, 4 µg, 5 µg, 6 µg, 7 µg, 8 µg, or 9 µg per 100,000 cells being transfected, as well as fractions in between, such as 2.3 µg, 3.5 µg, 4.7 µg. Thus, the amount of plasmid transfected may be any amount from 0.1 to 10 µg per 100,000 cells. The timing of testing for and visualizing the marker for transfection in part depends upon the promoter controlling the expression. Some promoters will express the downstream protein coding sequence after 7 days, such as chicken ovalbumin upstream promoter transcription factor. Others such as cytomegalovirus promoter (pCMV), can be express the downstream protein coding sequence within 48 hours. The timing of expression may also depend upon the transfection method including the viral vectors used.

Suppression of p53 Activity is not Particularly Limited

The suppression of p53 activity is not particularly limited in the means by which it is achieved. Activity of p53 may be suppressed by the following manipulations to the cell: administration of pharmacological inhibitors, reduction of p53 protein expression, or by introduction of an interfering protein that competes with or interacts with p53 to suppress its activity. One such inhibitor of p53 activity is mdm2, which interacts with and suppresses p53 activity until cellular injury such as DNA damage, cell cycle abnormalities or hypoxia, trigger the dissociation of mdm2 and p53. Therefore, it is contemplated, and is not limited to, the introduction of modified mdm2 or mdm2-mimetics that do not dissociate from endogenous p53 protein in response to cellular injury.

Reduction of p53 protein expression can further be achieved by reducing the expression of p53 mRNA or by suppression of p53 gene transcription. Genetic modifications such as gene deletion, insertion of stop codons, or introductions of single nucleotide polymorphisms into the p53 gene in the genome can result in a p53 protein with reduced activity, when the modified gene is transcribed and translated. However, these methods are not preferred as they may permanently modify the activity of a tumor suppressor protein in the reprogrammed cells and any cells that differentiate from the reprogrammed cells into somatic cells again. Pharmacological inhibition and knock-down approaches are preferred.

Pharmacological Inhibition of p53

Pharmacological inhibitors of p53 include, but are not limited to, pifithrin-α, cyclic pifithrin-α, pifithrin-µ, RITA, SJ 172550, and/or nutlin-3, and pharmaceutically acceptable salts thereof, such as pifithrin-α hydrobromide. Knockdown approaches include, but are not limited to, administration of antisense oligonucleotides, siRNA, RNAi, transfection of genes encoding for antisense oligonucleotides, siRNA, RNAi, all of which can be administered with or without the assistance of virion vectors, nucleofection, electroporation, or lipofectamine transfection reagents to promote cellular uptake of the nucleic acids.

Knockdown Approaches for Suppressing p53 Activity

Antisense oligonucleotides include antisense oligonucleotides modified to resist cellular and extracellular degradation such as locked nucleic acids (LNAs). With LNAs the 2'-hydroxyl group is linked to the 3' or 4' carbon atom of the sugar ring thereby forming a bicyclic sugar moiety, and is preferably a methelyne ($—CH_2—$)$_n$ group bridging the 2' oxygen atom and the 3' or 4' carbon atom wherein n is 1 or 2. Other modifications of antisense oligonucleotides to resist cellular and extracellular degradation include 2'-allyl (2'-$CH_2$—CH=$CH_2$), 2'-aminopropoxy (2'-$OCH_2CH_2CH_2NH_2$), 2'-O-allyl (2'-O—$CH_2$—CH=$CH_2$), 2'-methoxy (2'-O—$CH_3$), and 2'-fluoro (2'-F). Other modifications to the antisense oligonucleotides include modifications at the 3' position of the sugar on the 3' terminal nucleotide or to the 5' position of 5' terminal nucleotide, or incorporation of 2'-5' linked oligonucleotides. Antisense oligonucleotides that resist cellular and extracellular degradations may also be achieved by replacing pentofuranosyl sugar with sugar mimetics such as cyclobutyl moieties.

Antisense oligonucleotides can also be generated in the cell, such as in Example 1 below and FIG. 1. In Example 1 and FIG. 1, SEQ ID NO: 12 is a DNA sequence encoding antisense RNA for p53 mRNA. The SEQ ID NO: 12 DNA sequence encoding antisense RNA for p53 mRNA may be incorporated into the pCEP-4 vector construct, SEQ ID NO: 20. Thereafter, the incorporated construct of pCEP-4 and DNA sequence encoding antisense RNA for p53 mRNA may be transfected into the cell, for example, the cell of Example 1 below. The introduction of a gene encoding for antisense for p53 is not particularly limited such that it can include a number of different promoters, transcription initiators, and gene sequences to effect p53 protein knockdown. It is particularly preferred that the antisense sequence be directed to and complementary with the sequence of p53 mRNA that is near the initiation sequence for p53 translation.

Means of Confirming that p53 Activity is Suppressed is not Particularly Limited.

Suppression of p53 activity may include partial reduction of p53 activity within a cell as well as complete reduction of p53 activity within the cell. To determine whether a cell has suppressed p53 activity may be determined by comparing p53 activity in the cell to be reprogrammed against the same cell in which p53 activity is unmanipulated but which has otherwise has undergone all the other treatments contemplated, such as induction of exogenous Sox-2, Klf-4, Oct-3/4 and growth in media containing reprogramming-assistance factors (hereafter p53-unmanipulated cells). The p53-unmanipulated cell may be exposed to a scrambled oligonucleotide that is not complementary to any mRNA sequence of the cell, and the exposure to the scrambled oligonucleotide may be through the same means as with the manipulated cell, whether this be exposure to the scrambled oligonucleotide directly or transfection of a vector that expresses the scrambled oligonucleotide. The percentage of decrease in p53 protein which suppresses p53 activity can vary according to the knockdown approach, such as antisense oligonucleotides, siRNA, and RNAi. For example, a 5%, 10%, or 15% reduction in p53 protein in cells treated with an antisense oligonucleotide to p53 mRNA or transfected with a vector encoding for antisense oligonucleotides to p53 mRNA compared to p53-unmanipulated cells, can suffice to induce a physiologically effective reduction in p53 protein activity sufficient to reprogram somatic cells. In such cases, the antibody used by western blot to detect p53 protein may be generated using an antigen sequence from the p53 protein from the same species or a different species against which the anti-sense sequence was generated. For example, if sufficient homology exists for p53 across mouse and human, a p53 protein sequence from mouse, represented by SEQ ID NO: 14, and encoded for by the mouse p53 gene represented by SEQ ID NO: 13 can be used to select an antigen sequence against which an antibody is generated in a third species. The anti-p53 antibody derived from the mouse p53 protein sequence represented by SEQ ID NO: 14 can be tested on human p53 protein to determine whether the antibody cross reacts with human p53 antibody in a specific manner without cross reacting with other human proteins. As another example, siRNA or RNAi approaches may achieve a 30%, 40%, or 50% reduction in p53 protein in the cells treated with siRNA or RNAi compared to p53-unmanipulated cells in order to observe physiologically effective reduction in p53 protein activity sufficient to reprogram somatic cells.

Whether p53 activity is sufficiently suppressed by the manipulation to suppress p53 activity in the somatic cell, such as through a knock-down approach or pharmacological inhibition, may be determined by measuring the reprogramming efficiency. For example, a higher reprogramming efficiency may suggest that p53 activity was suppressed. In this regard, a reprogramming efficiency of 0.0006% may be used as a marker for determining whether the method of suppressing p53 activity was effective. Alternatively, other proxies may be used for determining whether the manipulation suppressed p53 activity; these include but are not limited to measuring cellular transduction pathways downstream of p53. For example, p53, when activated, can in turn trigger cell cycle arrest, leading to DNA repair and then a restart of the cell cycle. Alternatively, p53 can trigger apoptosis, DNA cleavage, and death and elimination of damaged cells, when activated. To determine whether the manipulation, such as a knock-down approach or pharmacological inhibition, suppresses p53 activity, somatic cells may be: 1) stained for cell cycle markers to determine whether the cell cycle has been arrested, 2) observed for markers for DNA repair, 3) observed for markers for apoptosis, and/or 4) observed for activation of miR-34a and miR-145, and then the manipulated cells can be compared against the same markers in p53-unmanipulated cells. Several markers including markers for apoptosis and markers for cell cycle arrest may be measured with the same manipulation and compared against p53-unmanipulated cells. When p53 is suppressed by the manipulation, both apoptosis and cell cycle arrest may be suppressed relative to p53-unmanipulated cells; however, it is also contemplated that only cell cycle arrest or only apoptosis is suppressed in response to p53 suppression when compared to p53-unmanipulated cells. The staining for apoptosis and cell cycle arrest are not particularly limited and commercially available methods are readily available. For example, markers for apoptosis can include TUNEL staining, caspase-3 staining, bcl-2 staining, surviving staining, ubiquitin staining, markers for DNA damage, or markers for cell membrane "blebbing," each of which can be measured by counting the number of cells reaching a threshold amount of staining for the marker or quantifying the overall number of stains. Cell cycle arrest may be measured by staining for markers of G1, S, G2, and M phases, and the number of cells in each phase can be counted. An increase in the number of cells in the G1 or G2 in the p53-manipulated condition compared to the p53-unmanipulated condition can indicate that p53 activity has been suppressed.

Culturing with Reprogramming-Assistance Factors.

Cells may be exposed to reprogramming-assistance factors present in the culturing media. Reprogramming-assistance factors are discrete from Sox-2, Klf-4, Oct-3/4, EBNA-1, and exogenously expressed oncogenes such as c-Myc, 1-Myc, Lin28, Nanog, and SV40 large T antigen.

The term "reprogramming-assistance factor" as used herein refers to an extracellular molecule that modulates the epigenetic programming, the state of differentiation, and/or the metabolism of a cell and assists in the reprogramming of a somatic cell expressing episomal Sox-2, Klf-4, and Oct-3/4.

For example, a molecule that may modulate epigenetic programming may be a molecule that inhibits or activates an intracellular enzyme that modifies DNA or modifies proteins that bind to DNA. One such intracellular enzyme that modifies DNA is DNA methyltransferase, which methylates DNA; another is ten eleven translocation enzyme (TET) which, in part, reverses DNA methylation. An intracellular enzyme that could modify a protein associated with DNA is histone deacetylase (HDAC), which removes acetyl groups from histones, or histone acetyltransferase, which adds acetyl groups to histones, or histone methyltransferase which adds methyl groups to histones, or histone demethylases, which removes methyl groups from histones. Thus, inhibitors and activators of HDAC, DNMT, TET, histone acetyltransferases, histone demethylases, and histone methyltransferases are contemplated as reprogramming-assistance factors.

A molecule that may modify the state of differentiation of a cell is a molecule that can modulate developmental growth factors important for the maintenance of stem cells or the differentiation of stem cells into somatic cells. For example, beta-catenin, transforming growth factor-beta, glycogen-synthase kinase-3 β (GSK-3β), and alk5 are considered part of the Wnt signaling pathway. Wnt signaling, through beta-catenin, transforming growth factor-beta, glycogen-synthase kinase-3, and/or alk5, has been shown to be important for gastrulation, the differentiation of neural crest cells into the bones of the jaw and inner ear, for stem cell renewal, for epithelial to mesenchymal transitions, and for differentiation of cells into mesodermal lineages. In some cases, the Wnt pathway can involve a signaling cascade where one protein activates another protein. In some cases, the Wnt pathway can involve a signaling cascade where one protein inhibits another protein. In some cases, the Wnt pathway can involve a signaling cascade where one protein inhibits a second protein, and the second protein inhibits a third protein (wherein the Wnt pathway when activated involves the disinhibition of the third protein). A molecule that can modulate the state of differentiation of a cell or developmental growth factors important for the maintenance of stem cells or the differentiation of stem cells into somatic cells, can thus activate or inhibit the developmental growth factor signaling cascade. For example, it may be beneficial to inhibit alk5, but if alk5 signaling inhibits another protein in the pathway such as GSK-3β, which in turn phosphorylates beta-catenin, then it may be beneficial to use an GSK-3β activator instead of an Alk-5 inhibitor to achieve the same result of reducing beta-catenin phosphorylation and increase beta-catenin mediated transcription of Wnt-responsive genes. Thus a small or large molecule which modulates a state of differentiation may be either an activator or an inhibitor of growth factor signaling cascade molecules, including Wnt1 signaling cascade members. Other molecules and signaling pathways are also important for the differentiation of other cells into lineages of ectodermal, mesodermal, and endodermal origins.

A molecule that may modulate the metabolism of the cell, may be a molecule with modulates the glycolysis of the cell. Phosphoinositide-dependent protein kinase-1 is known to modulate the glycolysis of the cell and therefore an inhibitor phosphoinositide-dependent protein kinase-1 is also known to modulate glycolysis of the cell.

The exposure to reprogramming-assistance factors may occur before, concurrent with or after suppression of p53 activity or may occur before, concurrently with, or after transfection of and expression of exogenous Sox-2, Klf-4, and/or Oct-3/4. The culturing conditions for providing reprogramming-assistance factors are not particularly limited. In some embodiments, the reprogramming-assistance factors may be placed into the reprogramming media and the reprogramming media may be placed on the somatic cells which have been transfected with Sox-2, Klf-4 and Oct-3/4, or in which Sox-2, Klf-4 and Oct-3/4 have been, or are in the process of being, or are going to be exogenously expressed from DNA that has not integrated into the genome. In some embodiments, the reprogramming media may be comprised of a base media which is further comprised of 50% Dulbecco's Modified Eagle's Medium (DMEM) and 50% Ham's F-12 Media (50% DMEM/50% Ham's F-12 being also known as DMEM/F-12). In some embodiments, the reprogramming media is an admixture of the DMEM/F12 media and 1×N-2 Supplement. In some embodiments, the reprogramming media is an admixture of the DMEM/F12 media and 1×B-27 Supplement. In some embodiments, the reprogramming media is an admixture of the DMEM/F12 media and 1×MEM non-essential amino acids. In some embodiments, the reprogramming media is an admixture of the DMEM/F12 media and 1× Glutamax Supplement. In some embodiments, the reprogramming media is an admixture of the DMEM/F12 media and 1 mM glutamine supplement. In some embodiments, the reprogramming media is an admixture of the 1×DMEM/F12 with HEPES (ThermoFisher Scientific, Waltham, Mass.), 1×N-2 Supplement (ThermoFisher Scientific, Waltham, Mass.), 1×B-27 Supplement (ThermoFisher Scientific, Waltham, Mass.), 1×MEM Non-Essential Amino Acids (ThermoFisher Scientific, Waltham, Mass.) 1× Glutamax (ThermoFisher Scientific, Waltham, Mass.) and 1× Beta-Mercaptoethanol (ThermoFisher Scientific, Waltham, Mass.).

In some embodiments, the reprogramming-assistance factors may include at least one HDAC inhibitor. In some embodiments the HDAC inhibitor may be sodium butyrate or valproic acid.

In some embodiments, the reprogramming-assistance factors may include at least one Alk-5 inhibitor. In some embodiments, the Alk-5 inhibitor may be 3-(6-Methyl-2-pyridinyl)-N-phenyl-4-(4-quinolinyl)-1H-pyrazole-1-carbothioamide (A83-01), 4-[4-(1,3-benzodioxol-5-yl)-5-(2-pyridinyl)-1H-imidazol-2-yl]benzamide, 4-[4-[3-(2-Pyridinyl)-1H-pyrazol-4-yl]-2-pyridinyl]-N-(tetrahydro-2H-pyran-4-yl)-benzamide, or 6-[2-(1,1-Dimethylethyl)-5-(6-methyl-2-pyridinyl)-1H-imidazol-4-yl]quinoxaline.

In some embodiments, the reprogramming-assistance factors may include at least one activator of glycolysis. In some embodiments, the activator of glycolysis includes at least one phosphoinositide-dependent protein kinase-1 inhibitor. In some embodiments, the phosphoinositide-dependent protein kinase-1 inhibitor(s) may include at least one of 5-(4-Chloro-phenyl)-3-phenyl-pent-2-enoic acid (PS48); α,α,-Dimethyl-4-[2-methyl-8-[2-(3-pyridinyl)ethynyl]-1H-imidazo[4,5-c]quinolin-1-yl]-benzeneacetonitrile (BAG956); N-[3-[[5-Iodo-4-[[3-[(2-thienylcarbonyl)amino]propyl]amino]-2-pyrimidinyl]amino]phenyl]-1-pyrrolidinecarboxamide (BX795); (3S,6R)-1-[6-(3-Amino-1H-indazol-6-yl)-2-(methylamino)-4-pyrimidinyl]-N-cyclohexyl-6-methyl-3-piperidinecarboxamide (GSK 2334470); 2-Amino-N-[4-[5-(2-phenanthrenyl)-3-(trifluoromethyl)-1H-pyrazol-1-yl]phenyl]acetamide (OSU03012); and 4-Dodecyl-N-1,3,4-thiadiazol-2-yl-benzenesulfonamide (PHT427).

In some embodiments, the reprogramming-assistance factors may include sodium butyrate, A83-01, and PS48. In some embodiments, the reprogramming-assistance factors may include sodium butyrate, A83-01, PS48, Fibroblast Growth Factor-2 (also known as basic-Fibroblast Growth Factor, FGF-2), and Transforming Growth Factor-β (TGF-β). FGF-2 is considered important for maintaining the IPSCs, once reprogrammed, in a de-differentiated state and is not considered necessary for the reprogramming process or survival of the reprogrammed cells. Likewise, TGF-β is not considered necessary for the reprogramming or the survival of the reprogrammed cells but is instead important for low level intracellular signaling through Alk-5, and/or the Transforming Growth Factor-β receptor 2, via their inhibition or activation of SMAD2/3, SMAD4, Tak1, MKK3/6, MKK4, glycogen synthase kinase-3, and/or beta-catenin pathways to maintain IPSCs, once reprogrammed, in a de-differentiated state.

In some embodiments, FGF-2 and TGF-β are added with the first administration of the other reprogramming-assistance factors, such as the Alk5 inhibitor, HDAC inhibitor, and phosphoinositide-dependent protein kinase-1 inhibitor. In some embodiments, FGF-2 and TGF-β are added with the subsequent administration of the other reprogramming-assistance factor, such as the Alk5 inhibitor, HDAC inhibitor, and phosphoinositide-dependent protein kinase-1 inhibitor, but not the first administration of the other reprogramming-assistance factors. In some embodiments, FGF-2 and TGF-β are added after the administration of and removal of the other reprogramming-assistance factors, such as the Alk5 inhibitor, HDAC inhibitor, and phosphoinositide-dependent protein kinase-1 inhibitor.

In some embodiments, cells that are not reprogrammed will not be viable in the reprogramming media within one week after initial exposure to the media. In other embodiments, the cells that are not reprogrammed will not be viable in the reprogramming growth media. Reprogramming growth media is media in which the reprogramming-assistance factors have not been added but FGF-2 and TGF-β have been added. In some cases, all the cells that are not reprogrammed will have died within 22 days of initial exposure of the cells to reprogramming media. When all the cells that have not been reprogrammed have died, the number of colonies can be counted to calculate the reprogramming efficiency. Each colony of cells may be presumed to have originated from a single reprogrammed cell that has divided to generate a colony if the number of cells are plated with a sufficient dilution such that the colonies originating from separate reprogrammed cells do not grow into one another. It is therefore contemplated that the practitioner titrate the plating of the cells after transfection and before placing the cells in the reprogramming media so that the reprogrammed and viable cells do not touch one another, and are sufficiently separated so that the individual colonies do not grow together. By titrating and plating several dilutions of cells after transfection, the practitioner can validate the colony counts across a range of titrations to ensure that the colony counts are consistent, and reflect the number of cells with plating. If the number of colonies counted are lower for more concentrated titrations, then each colony may not have originated from a single reprogrammed cell, and the practitioner should exclude the concentrated titrations and rely instead on titrations with a lower concentration of cells initially plated. IPSC reprogramming efficiency (expressed as a percentage) is defined by the following formula: number of colonies counted per 100,000 input cells×100.

In some embodiments, the reprogramming efficiency is greater than 0.0006%. In some embodiments, the reprogramming efficiency is greater than 0.001%. In some embodiments, the reprogramming efficiency is greater than 0.003%.

EXAMPLES

Example 1: Generation of Adherent Cells and Vector Constructs

Cultured neonatal foreskin fibroblasts were isolated from discarded foreskin obtained by routine circumcisions through an approved Institutional Review Board (IRB) approved informed consent. Isolated cultured cells were de-identified in accordance with IRB procedures.

Each vector is based on the pCEP-4 episomal vector, SEQ ID NO: 20, previously developed by ThermoFisher Scientific (FIG. 1). Each vector contains an Epstein Barr virus origin of replication (OriP) as set forth in SEQ ID NO: 11, SV40 poly-adenylation sequence represented by SEQ ID NO: 19, 2A cleavage sequence for tandem genes, a bacterial origin of replication, as well as ampicillin and hygromycin resistance genes. There were seven separate vectors, which encode for a unique single reprogramming gene or tandem reprogramming genes separated by a 2A cleavage sequence, as illustrated in FIG. 1. Each vector either contains a single gene or tandem genes separated by a 2A cleavage sequence. In addition to the traditional Yamanaka factors (Oct-3/4, Sox-2 and Klf-4), there are separate vectors containing 1-Myc along with Lin28, along with separate episomal vectors that encodes for p53 anti-sense and c-Myc. The system also contains a vector that encodes for Red Fluorescent Protein to monitor gene delivery and to detect silencing of exogenous reprogramming-assistance factors. Lastly, for each of the vectors to efficiently remain in the cell cytoplasm for only a short time frame, the plasmid vector encodes for Epstein Barr Nuclear Antigen-1 (EBNA-1).

Example 2: Transfection of Different Mixtures of Vector Constructs

One group of cultured human foreskin fibroblast (HFF) cells was reprogrammed with an additional vector that contained L-Myc and Lin28 separated by a 2A cleavage sequence. A separate group of cultured HFF cells was reprogrammed with an additional vector that encoded for the gene that expressed c-Myc. Lastly, one group of cultured HFF cells was reprogrammed without Myc and Lin28. Each condition contained a mixture of vectors that contain genes that encode for Oct3/4, Sox2, Klf-4, EBNA-1, p53 anti-sense and red fluorescent protein (RFP). FIG. 2 summarizes the different combination of specific vectors and reprogramming factors for the following conditions: 1) Oct3/4, Sox2, Klf-4, EBNA-1, p53 anti-sense, and RFP; 2) Oct3/4, Sox2, Klf-4, EBNA-1, p53 anti-sense, RFP, 1-Myc and Lin28; and 3) Oct3/4, Sox2, Klf-4, EBNA-1, p53 anti-sense, RFP, and c-Myc. In other conditions, plasmids encoding EBNA-1, Sox-2, Klf-4 or Oct-3/4 were omitted from the combination of the specific vectors. In each condition, equal weights (μg) of each plasmid were combined to a total of 3.5 μg of DNA of the episomal reprogramming mix. FIG. 3 includes different polynucleotide and amino acid sequences for use in methods as disclosed herein, including for example, DNA that can be included in the pCEP-4 plasmid as vector constructs N1-7 in FIG. 1, the amino acid sequences translated therefrom, the OriP DNA sequence to which EBNA-1 binds, and the SV40 poly-adenylation sequence in the pCEP-4 plasmid. Additionally, FIG. 3 also shows DNA sequences and amino acid sequences for p53 from mouse.

Figure 4:
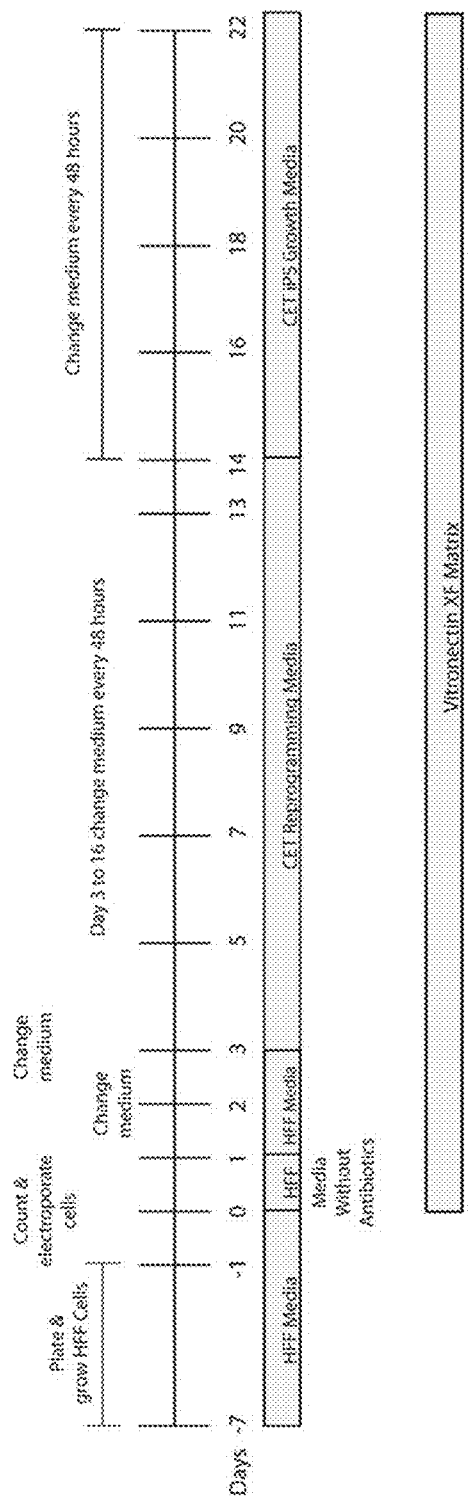
FIG. 4. Time sequence of IPSC reprogramming and cell expansion.

Example 3: Timeline for Culturing and Preparation of Adherent Cells for Transfection A temporal sequence of the IPSC reprogramming and cell expansion process is depicted in FIG. 4. Prior to transfection, a 6-well dish was coated with Vitronectin-XF according to manufacturer's directions (Primorigen, Madison, Wis.). HFF cells were examined under a microscope to ensure logarithmic growth phase and 80% confluency. HFF cells were washed with 1× Dulbecco's Phosphate Buffered Saline (ThermoFisher Scientific, Waltham, Mass.). HFF cells were then exposed to 0.25% Trypsin-EDTA. (ThermoFisher Scientific, Waltham, Mass.) and incubated at 37° Celsius for 4 minutes. When the cells were no longer adherent, an equal amount of 10 percent fetal bovine serum containing HFF growth media without antibiotics/anti-fungals was added. HFF cells were counted and the density was adjusted to $1\times10^5$ cells/mL. FIEF cells were spun to pellet at 200×G for 5 minutes. Each cell pellet, containing $1\times10^5$ cells/mL, was resuspended in 100 of Neon Electroporation Buffer R (ThermoFisher Scientific, Waltham, Mass.).

Example 4: Transfection

All the cultured conditions were electroporated and sequentially exposed to an IPSC reprogramming media followed by IPSC growth media in accordance with the timeline illustrated in FIG. 4. In brief, 3.5 µg of DNA of the episomal reprogramming mix was added to each tube and mixed gently. A Neon Electroporation Tip-100 was used to introduce the cells to the DNA. Using Buffer E2 for the chamber buffer, the cells were electroporated at 1650 V for 10 milliseconds for 3 cycles. Immediately after electroporation, the cells were placed in HFF growth media containing no antibiotics/antifungals on the previously coated 6-well dish for the first 24. Alternatively, another group of cells were transfected with a chemical mediated transfection, Lipofectamine LTX (ThermoFisher Scientific, Waltham, Mass., Catalog No. 15338100), using the manufacturer's protocol. Efficiency of gene transfer was measured by red fluorescence protein expression 48 hours post-transfection. RFP protein was expressed in cis with genes required for IPS reprogramming.

Example 5: Culturing in Reprogramming Media with Reprogramming-Assistance Factors After 24 hours, the growth media was withdrawn and replaced with Cellular Engineering Technologies commercial IPSC reprogramming media (Catalog No. CET.IPS.RPM-250 containing antibiotics/antifungals). IPSC Reprogramming media comprised 1×DMEM/F12 with HEPES (ThermoFisher Scientific, Waltham, Mass.), 1×N-2 Supplement (ThermoFisher Scientific, Waltham, Mass.), 1×B-27 Supplement (ThermoFisher Scientific, Waltham, Mass.), 1×MEM Non-Essential Amino Acids (ThermoFisher Scientific, Waltham, Mass.) 1× Glutamax ((ThermoFisher Scientific, Waltham, Mass.)) and 1× Beta-Mercaptoethanol (ThermoFisher Scientific, Waltham, Mass.). The IPSC Reprogramming media was admixed with the following reprogramming-assistance factors: Sodium Butyrate (Reagents Direct, Encinitas, Calif.), A83-0-1 (Reagents Direct, Encinitas, Calif.), and PS48 (Reagents Direct, Encinitas, Calif.), and further admixed with ascorbic acid (Sigma-Aldrich, St. Louis, Mo.) and Human Recombinant FGF-2 (Peprotech, Rocky Hill, N.J.). To evaluate successful transfection, cells were examined under a microscope to detect RFP fluorescence within the first 48 hours after transfection. Both cells transfected via nucleofection and those transfected via Lipofectamine LTX transfected fluoresced more under the RFP excitation and emission wavelengths than untransfected controls, demonstrating successful introduction of and expression of the plasmids into the REF cells. Cells were fed with fresh IPSC reprogramming media containing the above reprogramming-assistance Factors, FGF-2, and ascorbic acid every 48 hours through day 14 of the reprogramming process. By day 14, IPSC colonies were typically formed as shown under phase microscopy (FIG. 5A). Cultured cells were then switched to a xeno-free, feeder-free, growth media for an additional 7 days (Cellular Engineering Technology Catalog No. CET.IPS.RPM-250) without reprogramming-assistance Factors but with FGF-2 and a full media replacement was performed every 24 hours. Mature IPS colonies were observed starting around day 17 post electroporation, which displayed sharp and distinct borders. The identity of the IPS colonies was confirmed with positive probes for various IPSC markers including SSEA-4 Live Stain (ThermoFisher Scientific, Waltham, Mass., discontinued; Stemgent, Cambridge, Mass. Catalog No. 09-0097) and Alkaline Phosphatase (Catalog No. 00-0055, Stemgent, Cambridge, Mass.). By day 22 the number of colonies were counted and stained with alkaline phosphatase or SSEA4 livestain.

Example 6: Histological Staining/Fluorescence and Immunocytochemistry Staining/Fluorescence for IPSC Markers Alkaline phosphatase stain (Stemgent, Cambridge Mass.) and SSEA-4 livestain were conducted in accordance with the manufacturer's protocol. For fluorescence Immuno-cytochemistry for Nanog, Oct-3/4, and TRA160, cells were first fixed under 4% paraformaldehyde at a pH of 7.4, and washed subsequently with phosphate buffered saline (PBS), 3 times for 10 minutes each. Cells were permeabilized under PBS with 0.1% by volume Triton (PBS-0.4% T) overnight, and then blocked with PBS-0.1% T containing 1% by weight bovine serum albumin and 10% by volume normal goat serum. Then anti-Nanog conjugated with ALEXAFLOUR®488 (Abcam, Cat. No. ab196155), anti-Oct-3/4 conjugated with ALEXAFLOUR®488 (Abcam, Cat. No. ab208272), or anti-TRA160 (Abcam Cat. No. ab16288) were each applied at a 1:500 dilution (v:v) in PBS-0.1% T containing 0.5% by weight bovine serum albumin and 5% by volume normal goat serum and washed five times in PBS-0.1% T for 15 minutes each. For the anti-TRA160 ICC, anti-mouse antibody conjugated with ALEXAFLOUR®488 was applied at a 1:500 dilution (v:v) in PBS-0.1% T containing 0.5% by weight bovine serum albumin and 5% by volume normal goat serum and washed five times in PBS-0.1% T for 15 minutes each. All the slides were then coverslipped and imaged on a Olympus Fluorescent BX43 microscope using CellSens Software.

Example 7: Statistical Testing

IPSC reprogramming efficiency (expressed as a percentage) was defined by the following formula: number of colonies counted per 100,000 input cells×100. Data are reported as means±SE. Comparisons between more than two groups were made with analysis of variance. Individual group comparisons were done with Tukey's honestly significant difference test for post hoc comparison of means. Differences were considered significant at the $P \leq 0.05$ level.

Example 8: Morphology of and Markers for a Reprogrammed IPSC from Somatic Cells

By day 14, IPSC colonies were typically formed as shown under phase microscopy (FIG. 5A). Colonies exhibit the typical flat shape and refractile border. IPSC colonies also stain positive for alkaline phosphatase (FIG. 5B) and also express SSEA4 (FIG. 5C), confirming the process resulted in fully reprogrammed cells. Additionally, representative colonies depicted by phase microscopy and other pluripotent biomarkers (Nanog, Oct4 and TRA160) were observed within the same corresponding colony (FIG. 5D).

Figure 6A:
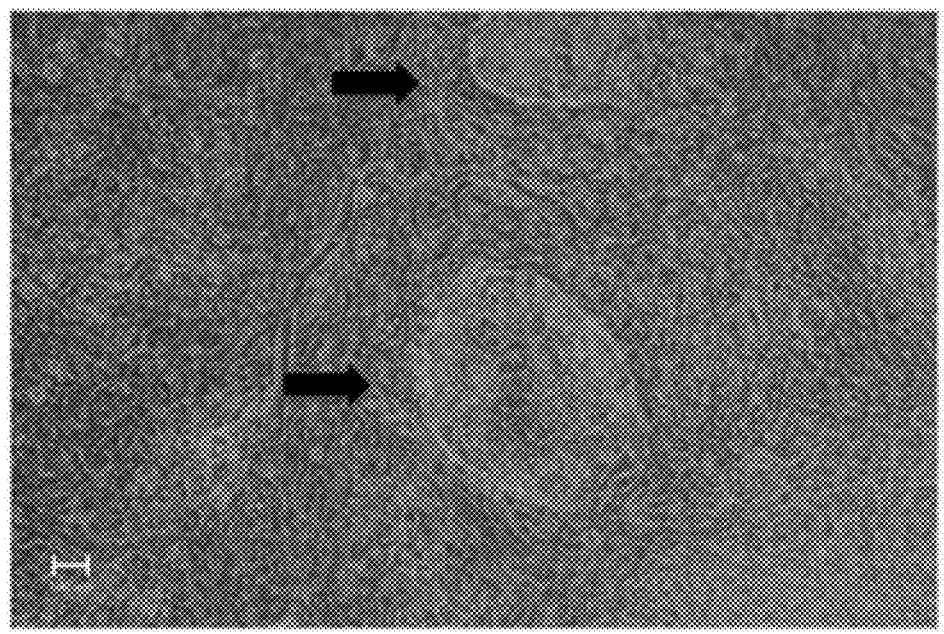
FIGS. 6A-6B. Ectopic episomal vectors are shut down in cultured IPSC colonies within 2 weeks in cells exposed to reprogramming-assistance factors and a mixture of episomal vectors free of Myc and Lin28. The figure shows the decrease in RFP episomal reporter protein expression in culture IPSC colonies at day 17.
Figure 6B:
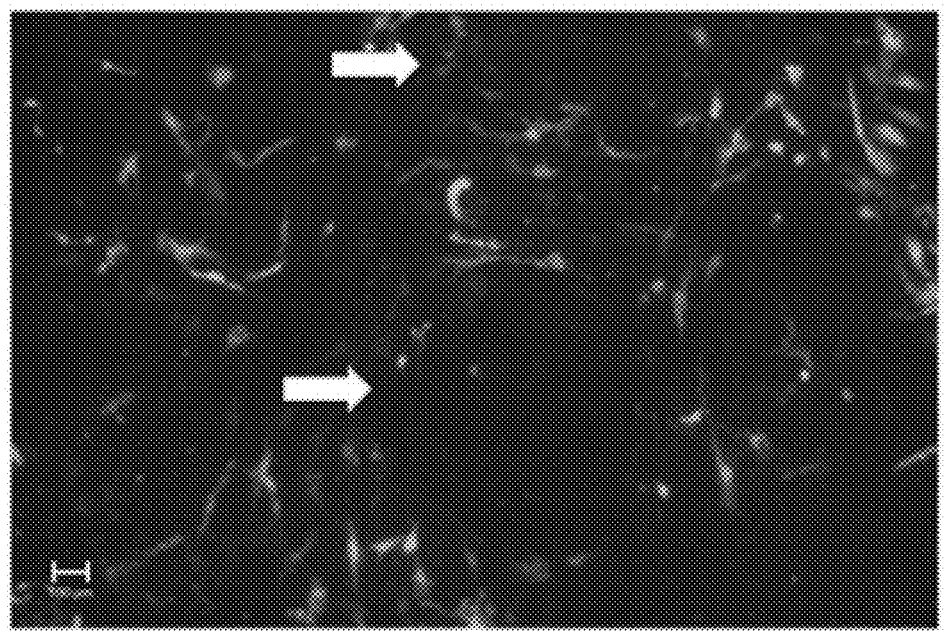

Example 9: Loss of Episomal Vectors and/or Expression of Genes from Episomal Plasmids after Two Weeks Lack of red fluorescent protein (RFP) expression in the IPSC colonies (FIGS. 6A-6B.) confirms that the episomal vectors cease expression at day 17. As shown in the FIG. 6A, there are two IPSC colonies that are highlighted under phase microscopy at day 17. The corresponding fluorescent images (FIG. 6B) show that the IPSC colonies no longer express RFP, which indicate that the genes encoded by the episomal vectors had shutdown.

Figure 7A:
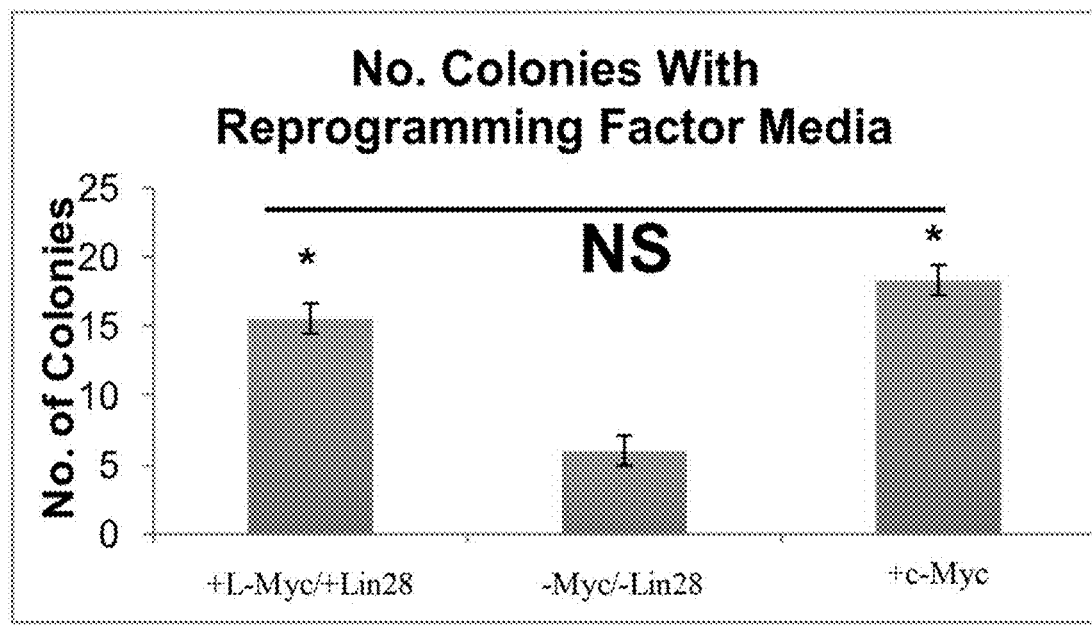
FIGS. 7A-7B. Effect of reprogramming media, L-myc/Lin28, c-Myc, and oncogene free conditions on number of colonies. The number of IPSC colonies created in the presence and absence of IPSC reprogramming-assistance factors.
Figure 7B:
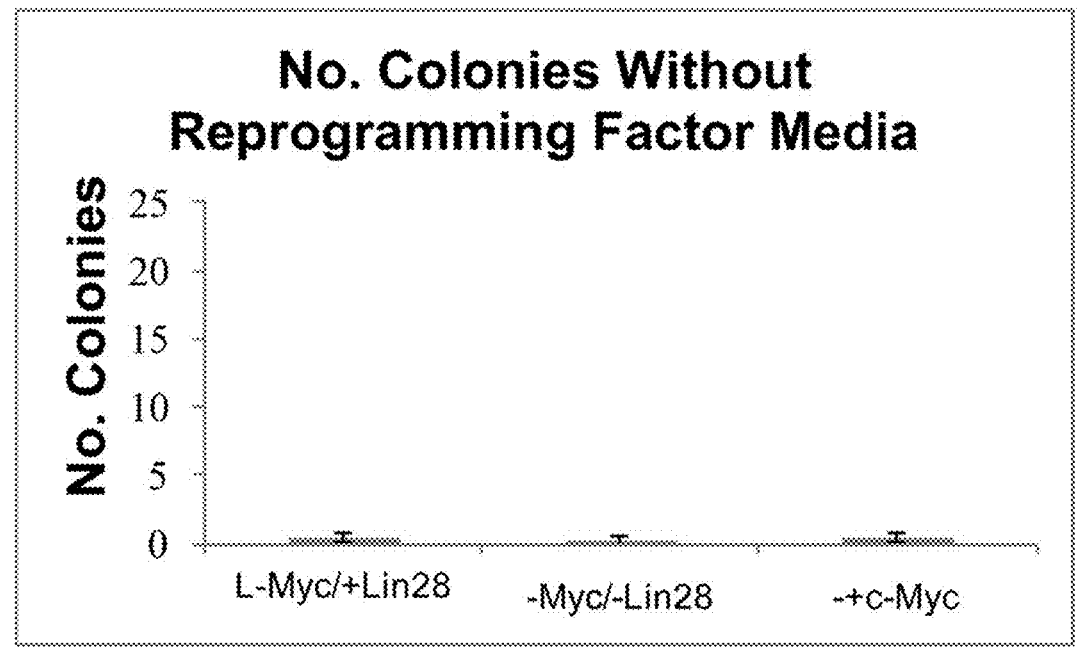

Example 10: Effect of Reprogramming-Assistance Factors on Reprogramming Efficiency of Somatic Cells Next, the numbers of colonies generated between the different vector constructs were compared among cultured cells reprogrammed in the presence and absence of reprogramming-assistance factors (FIGS. 7A-7B). When the vector mixtures are transfected in cultured cells in the absence of reprogramming-assistance factors, there are 0 to 1 colony detected (FIG. 7B) irrespective whether in the presence or absence of Myc-dependent and Lin28 transcriptional factors. When the vector-transfected cells were then cultured with reprogramming-assistance factors (FIG. 7A), the number of colonies significantly increased. Within cells cultured with reprogramming media, transfection with either 1-Myc combined with Lin28 or c-Myc increases the number of colonies surviving compared to transection with EBNA-1, Sox-2, KLF-4, and Oct-3/4 genes and p53-antisense alone. There was no statistically significant difference in the number of colonies formed between cells transfected with 1-Myc combined with Lin28 and those transfected with c-Myc. Omission of any one of EBNA-1, Sox-2, KLF-4, or Oct-3/4 from the transfection prevents all colony formation, regardless of whether c-Myc or Lin28 were also transfected. These observations were consistent regardless if c-Myc or Lin28 were included or not. Thus, all four reprogramming-assistance factors were necessary to mediate efficiently form IPSC using this episomal reprogramming system.

Figure 8:
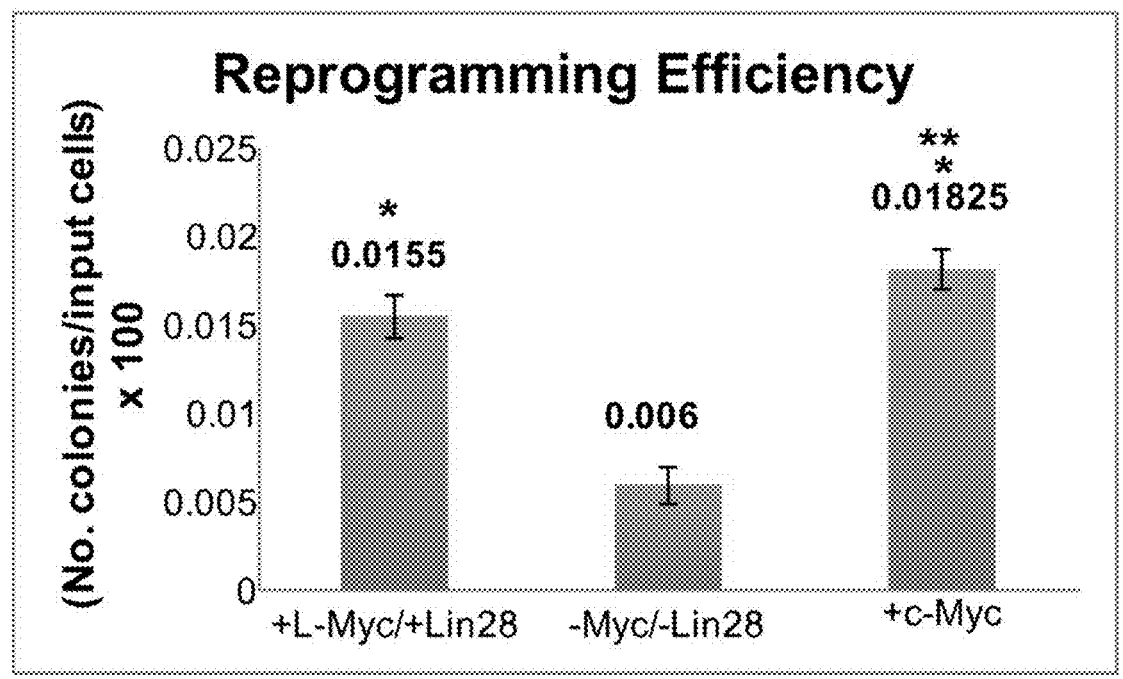
FIG. 8. Effect of L-myc/Lin28, c-Myc, and oncogene free conditions on reprogramming efficiency. Impact of IPSC reprogramming-assistance factors in the presence and absence of Myc and Lin28. Reprogramming efficiency is expressed as the percentage of colonies counted per 100,000 of input cells×100. Data are reported as the mean (±SE). Each group represents a sample size of 4 replicates. Data labeled with * highlight a statistical significant difference (p<0.05) between cultured cells treated with Myc and Lin28 and those cells treated without Myc and Lin28. ** denotes a significant statistical difference (p<0.05) between cells transfected with c-Myc and 1-Myc/Lin28.

Example 11: Effect of L-Myc/Lin28, c-Myc, and Oncogene-Free Conditions on Reprogramming Efficiency When expressed as the percentage of colonies counted per 100,000 of input cells, there was a parallel significant difference in the reprogramming efficiency between cells transfected in the presence and absence of Myc-dependent and Lin28 transcriptional factors (FIG. 8). Interestingly, cultured cells transfected with c-Myc resulted in a statistically higher reprogramming efficiency than cultured cells transfected with 1-Myc combined with Lin28.

Example 12: Effect of L-Myc/Lin28, c-Myc, and Oncogene-Free Conditions on Reprogrammed Cells Expressing SSEA4

Figure 9:
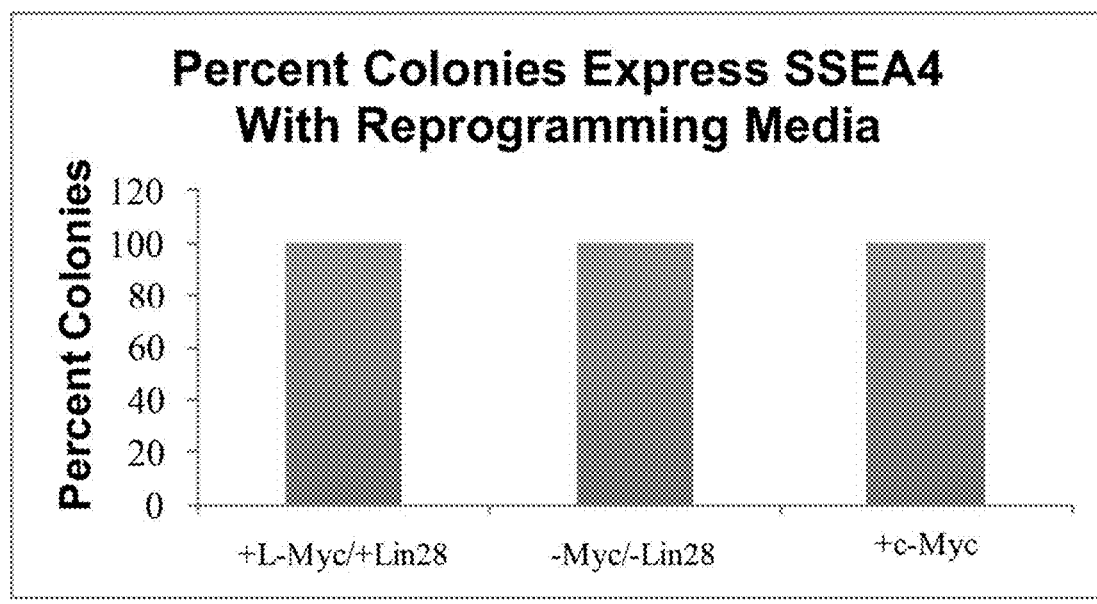
FIG. 9. Effect of L-myc/Lin28, c-Myc, and oncogene free conditions on percent of colonies expressing SSEA4. IPSC reprogramming with reprogramming-assistance factors, PS48, A83-01, and sodium butyrate, exhibit the same percentage of pluripotent colonies in the presence and absence of Myc/Lin28. Figure depicts the percentage of colonies that express SSEA4 among cultured HFF exposed to 1-Myc/Lin28, c-Myc and the absence of both oncogene groups. Data are reported as the mean (the standard error=0). All colonies stained positive for SSEA4. Each group represents a sample size of 4 replicates.

Next, reprogramming efficiency was further quantified by measuring the fraction of colonies that expressed SSEA4 when exposed to reprogramming factors. As shown in FIG. 9, all the colonies were fully reprogrammed irrespective of whether the cells were transfected in the presence or absence of Myc-dependent and Lin28 transcriptional factors (standard error=0). Taken together, the data demonstrate that the approach of combining reprogramming factors with mixtures of episomal vectors that lacked Myc and Lin28 and SV40 large T antigen created IPSC colonies which were all fully reprogrammed.

While the transfection of 1-Myc and c-Myc mediated an anticipated greater number of colonies than in the absence of these genes, all transfections groups, including those treated in the absence of c-Myc and 1-Myc expression vectors, yielded colonies in which 100 percent were fully reprogrammed based on the expression of SSEA4.

The present results demonstrate efficient episomal reprogramming in the absence of either SV40 large T antigen, or Nanog. Reprogramming could also be achieved with efficient results, albeit at a lower efficiency, in the absence of oncogenes, c-Myc, 1-Myc, and Lin28.

To confirm that the SSEA4 expressing colonies contained fully reprogrammed IPSCs, the induced pluripotent cells derived from fibroblasts were then exposed to various factors to trigger their differentiation into: 1) ectodermal cells, such as neural precursor cells; 2) mesodermal cells, such as heart muscle cells; and 3) endodermal cells.

Example 13: IPSCs Derived from HFF Cells can Differentiate into Cardiomyocytes, a Mesodermal Cell For differentiation of IPSCs into neural progenitor cells, IPSCs were first washed in pre-warmed 1× Dulbecco's Phosphate Buffered Saline (DPBS); DPBS was then removed, and 1× Versene at room temperature was added to the IPSCs, and cells were allowed to rest for 10 min Thereafter, the 1× Versene is removed and Cellular Engineering Technology's IPSC growth media is added. Cells are triturated to create cell clumps of approximately 100-200 cells and are plated onto a 3.5 cm round bottom dish which was previously coated for 1 hour with 1 mL of 10 µg/mL Vitronectin XF and then washed with CellAdhere™ buffer.

After two days, room-temperature Cellular Engineering Cardiomyocyte Differentiation Media was mixed by adding 2 mL of the Step 2 supplement into Cardiomyocyte Differentiation Step 2 and 4 Base Media. The IPSC growth media was removed and replaced with 2 mL of the Cardiomyocyte Differentiation Step 2 and 4 Media premixed with the Step 2 supplement. After 24 hours of incubation at 37° C., Cardiomyocyte Differentiation Step 3 media was prepared by mixing 2 mL of the Cardiomyocyte Differentiation Step 3 supplement with the Cardiomyocyte Differentiation Step 3 Base Media. Thereafter, the Cardiomyocyte Differentiation Media Step 2 and 4 was removed from the cells and replaced with 2 mL of the premixed Cardiomyocyte Differentiation Step 3 Media premixed with Step 3 supplement. Cells were then incubated at 37° C. for 2 days. Next, the Cardiomyocyte Differentiation Step 3 Media was removed and replaced with 2 mL of the premixed Cardiomyocyte Step 2 and 4 Media premixed with the Step 2 supplement. Cells were then incubated at 37° C. for 2 days. Thereafter, Cardiomyocyte Differentiation Step 5 Media was made by combining 2 mL of the Step 5 supplement with the Cardiomyocyte Differentiation Step 5 Base Media, and the Cardiomyocyte Step 2 and 4 Media was removed from the cells and replaced with 2 mL of the premixed Cardiomyocyte Differentiation Step 5 Media. Cells were then incubated at 37° C. for 2 days. Thereafter, cells were fed every 48 hours by replacing the media with unused premixed Cardiomyocyte Differentiation Step 5 Media for four days.

Figure 10:
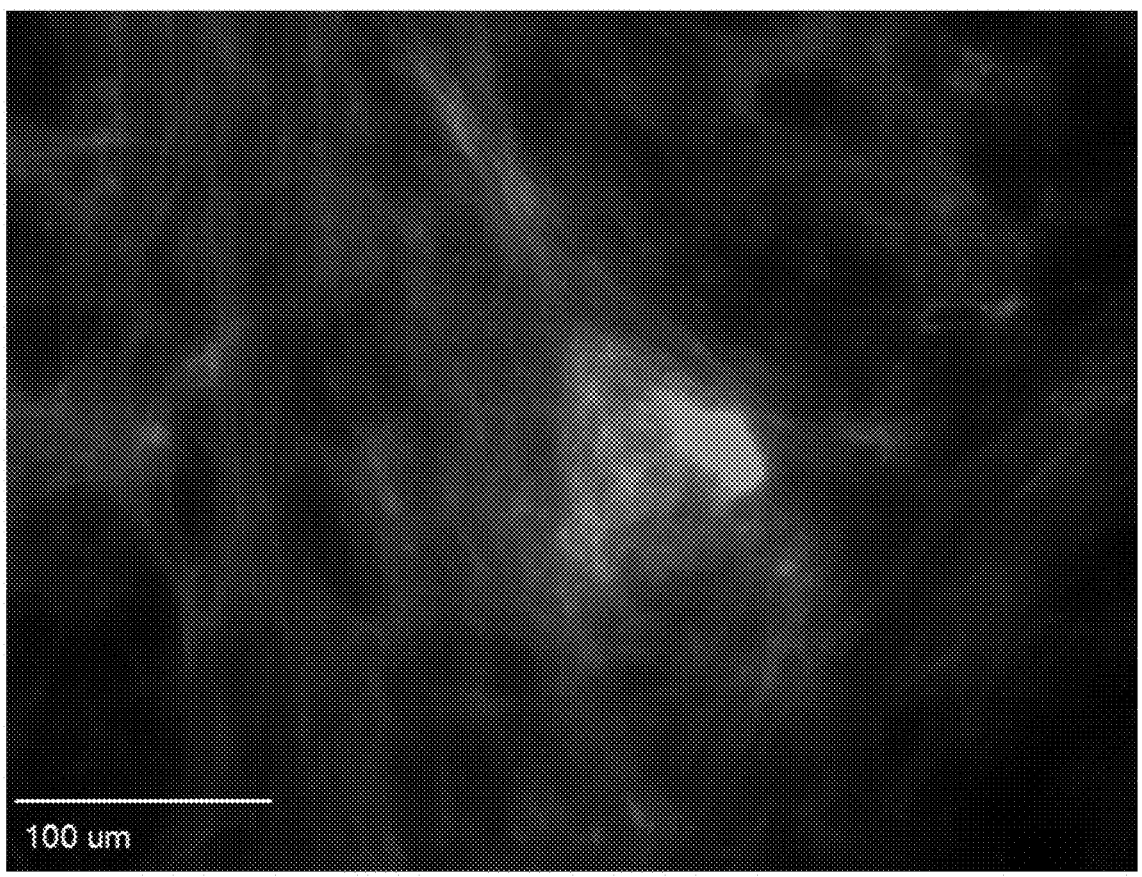
FIG. 10. HFF-Derived IPS Cells Converted to Cardiomyocytes Stained for Fluorescent Phalloidin (Green). Phalloidin binds to filamentous-actin, a protein component of heart muscle that together with tropomyosin and cardiac troponin executes a muscle contraction.
Figure 11:
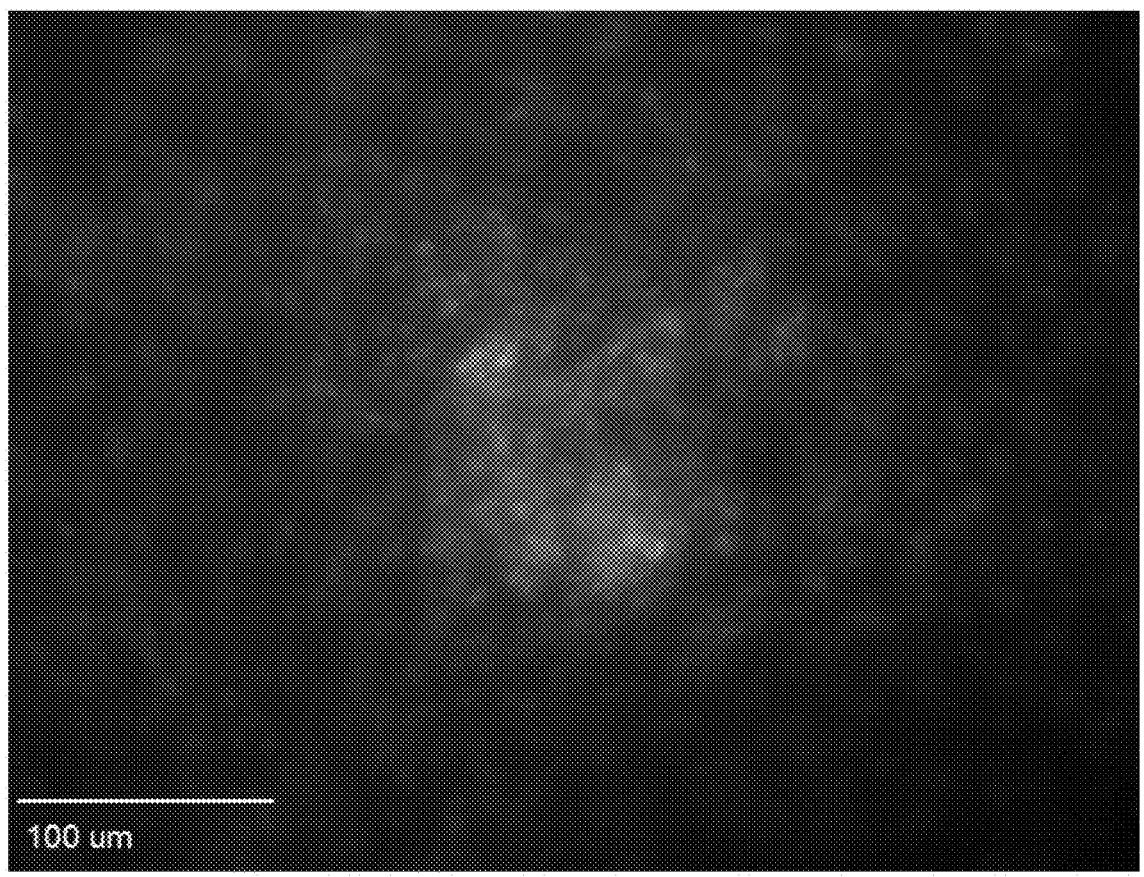
FIG. 11. HFF-Derived IPS Cells Converted to Cardiomyocytes Immunofluorescent for Cardiac Troponin (Green). Cardiac troponin is a protein that is found only in heart muscle.

Thirteen days after first passage of the cells, or 4 days after initial exposure to the Cardiomyocyte Differentiation Step 5 Media, the cells beat or contract in a pulsatile pattern. Cells were then fixed under 4% paraformaldehyde and immunocytochemistry for troponin and/or stained with fluorescent phalloidin which binds to and detects filamentous-actin (F-actin). FIG. 10 depicts fluorescent-phalloidin-stained cardiomyocytes (phalloidin stain is green) derived from IPSCs which were in turn derived from HFF. FIG. 11 depicts fluorescent-anti-troponin-stained cardiomyocytes wherein a green fluorophore conjugated secondary antibody was bound to the troponin antibody and the cells were derived from IPSCs which were in turn derived from HFF. The presence of phalloidin-fluorescent and troponin-fluorescent cells demonstrate that HFF cells can be reprogrammed into IPSCs because the IPSCs have the capacity to differentiate into cardiomyocytes, which is a mesoderm-derived cell. Additionally, these cells beat or contracted in a regular pulsatile manner demonstrating that the cells express hyperpolarization-activated cyclic nucleotide-gated channels which trigger an actin-myosin-mediated contraction, a mechanism only found in cardiomyocytes.

Example 14: IPSCs Derived from HFF Cells can Differentiate into Brachyury Positive Mesodermal Cell For differentiation of IPSCs into mesoderm cells, IPSCs were first washed in pre-warmed 1× Dulbecco's Phosphate Buffered Saline (DPBS); DPBS was then removed, and 1× Versene at room temperature was added to the IPSCs, and cells were allowed to rest for 10 min Thereafter, the 1× Versene was removed and Cellular Engineering Technology's IPSC growth media was added. Cells were triturated to create cell clumps of approximately 100-200 cells and were plated onto a 3.5 cm round bottom dish previously coated with 1.44 mL-1.92 mL of Matrigel (Corning Cat. No. 356234).

Cells were placed in an incubator at 37° C., 95% humidity, and 5% $CO_2$ for 24 hours, and then fed by replacing the IPSC Growth Media with fresh IPSC Growth Media every 24 hours until 85% to 90% confluency on the plate surface is met. Then, Cellular Engineering Technology's Mesoderm Differentiation Media (Catalog No. CET.DIFF.MDM-250) is made by mixing 10 mL of Cellular Engineering Technology's Mesoderm Supplement with Cellular Engineering Technology's Mesoderm Base Media. The IPSC Growth Media was immediately with 2 mL premixed Cellular Engineering Technology's Mesoderm Differentiation Media at room temperature, and placed back into the 37° C. incubator. Cells were then fed every 48 hours by replacing the pre-mixed Cellular Engineering Technology's Mesoderm Differentiation Media on the cells with fresh premixed Cellular Engineering Technology's Mesoderm Differentiation Media at room temperature, and placing the cells back in the 37° C. incubator.

Figure 12:
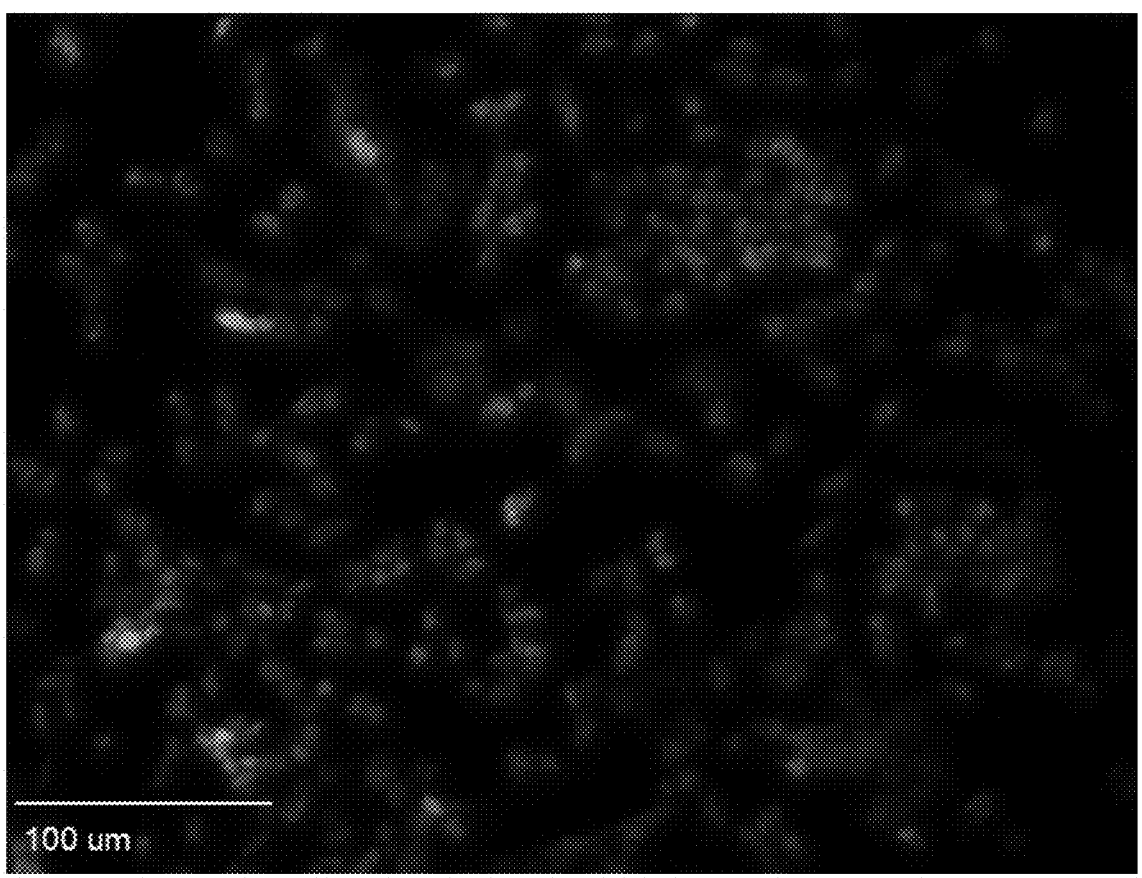
FIG. 12. IPS Cells Converted to Mesoderm Immunofluorescent for Brachyury. Mesoderm is the middle layer of the gastrula and differentiates into tissues such as muscle, bone (except the jaw bone and ear bones), tubule cells of the kidney, and connective tissue including red blood cells. Brachury is a protein specifically expressed in the mesoderm.

After 4 days in premixed Cellular Engineering Technology's Mesoderm Differentiation Media, the cells were fixed with 4% paraformaldehyde and fluorescent immunocytochemistry for brachyury protein using the antibody manufacturer's protocol. See for example Santa Cruz Biotechnology, Inc. brachyury N-19 antibody (Catalog No. SC-17743) available at, for example, www.scbt.com/scbt/product/brachyury-antibody-n-19. FIG. 12 depicts anti-brachyury-fluorescent cardiomyocytes wherein a green fluorophore conjugated secondary antibody is bound to the anti-brachyury antibody, and the cells were derived from IPSCs which were in turn derived from HFF. The presence of brachyury-fluorescent cells demonstrate that HFF cells can be reprogrammed into IPSCs because the IPSCs have the capacity to differentiate into mesoderm cells.

Example 15: IPSCs Derived from HFF Cells can Differentiate into Neural Progenitor Cells, an Ectodermal Cell For differentiation of IPSCs into neural progenitor cells, IPSCs were first washed in pre-warmed 1× Dulbecco's Phosphate Buffered Saline (DPBS); DPBS was then removed, and 1× Versene at room temperature was added to the IPSCs, and cells were allowed to rest for 10 min Thereafter, the 1× Versene was removed and Cellular Engineering Technology's IPSC growth media was added. Cells were triturated to create cell clumps of approximately 100-200 cells and were plated onto a 3.5 cm round bottom dish previously coated with 1.44 mL-1.92 mL of Matrigel (Corning Cat. No. 356234).

After two days, room-temperature Cellular Engineering Technology's Neural Progenitor Cell Induction Media (Catalog No. CET.DIFF.NPCM-250), was prepared by adding 16 mL of the Cellular Engineering Technology's Neural Progenitor Supplement to the Cellular Engineering Technology's Neural Progenitor Base Media. The IPSC growth media was removed from the IPSCs and 2 mL of the pre-mixed, room-temperature Cellular Engineering Technology's Neural Progenitor Cell Induction Media was added. The media was then replaced daily for four days with another 2 mL of pre-mixed, room-temperature Cellular Engineering Technology's Neural Progenitor Cell Induction Media.

Figure 13:
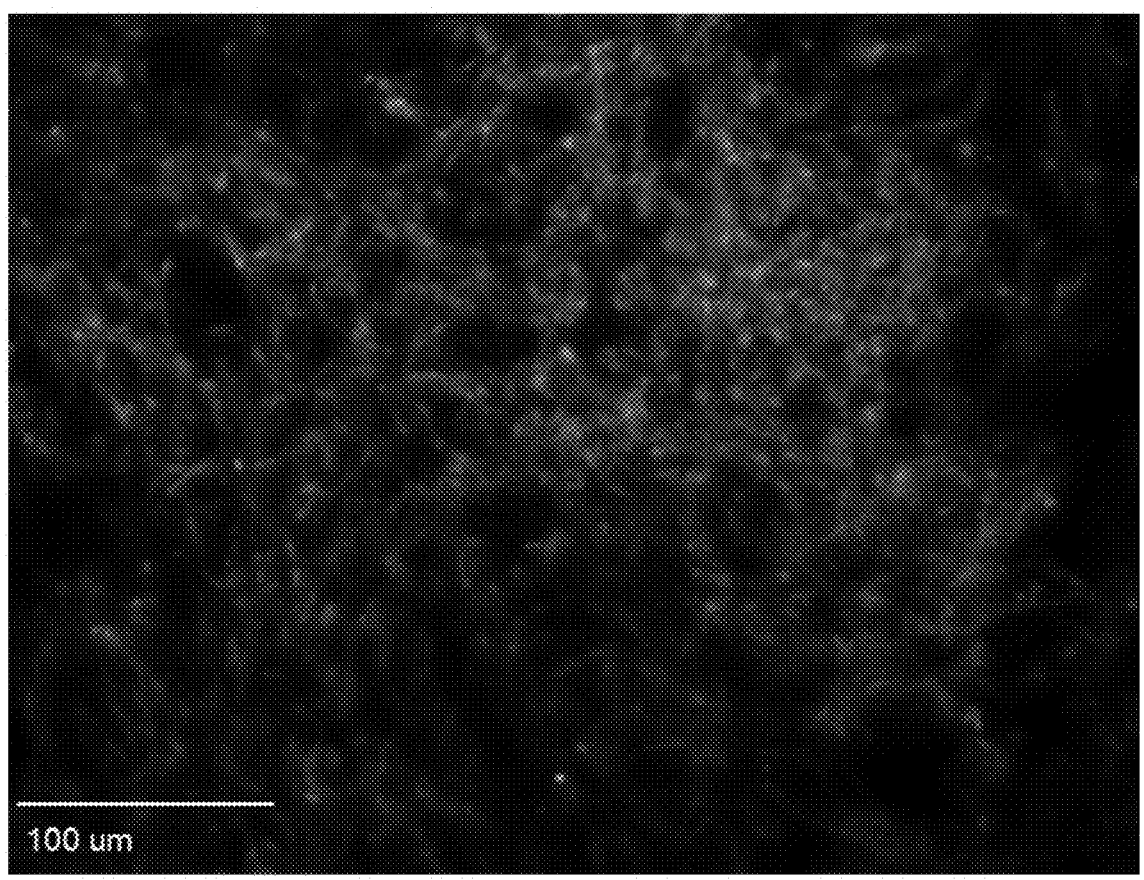
FIG. 13. IPS Cells Converted to Neural Progenitor Cells Immunofluorescent for Nestin. Neural progenitor cells are derived from the ectoderm during neurulation, which is the first developmental event to give rise to a specific line of tissue, neural tissue. Neural Progenitor cells give rise to neurons and glia, through processes of neurogenesis and gliogenesis. Nestin is a neural progenitor cell marker, whose expression is largely lost after neurogenesis or gliogenesis.
Figure 14:
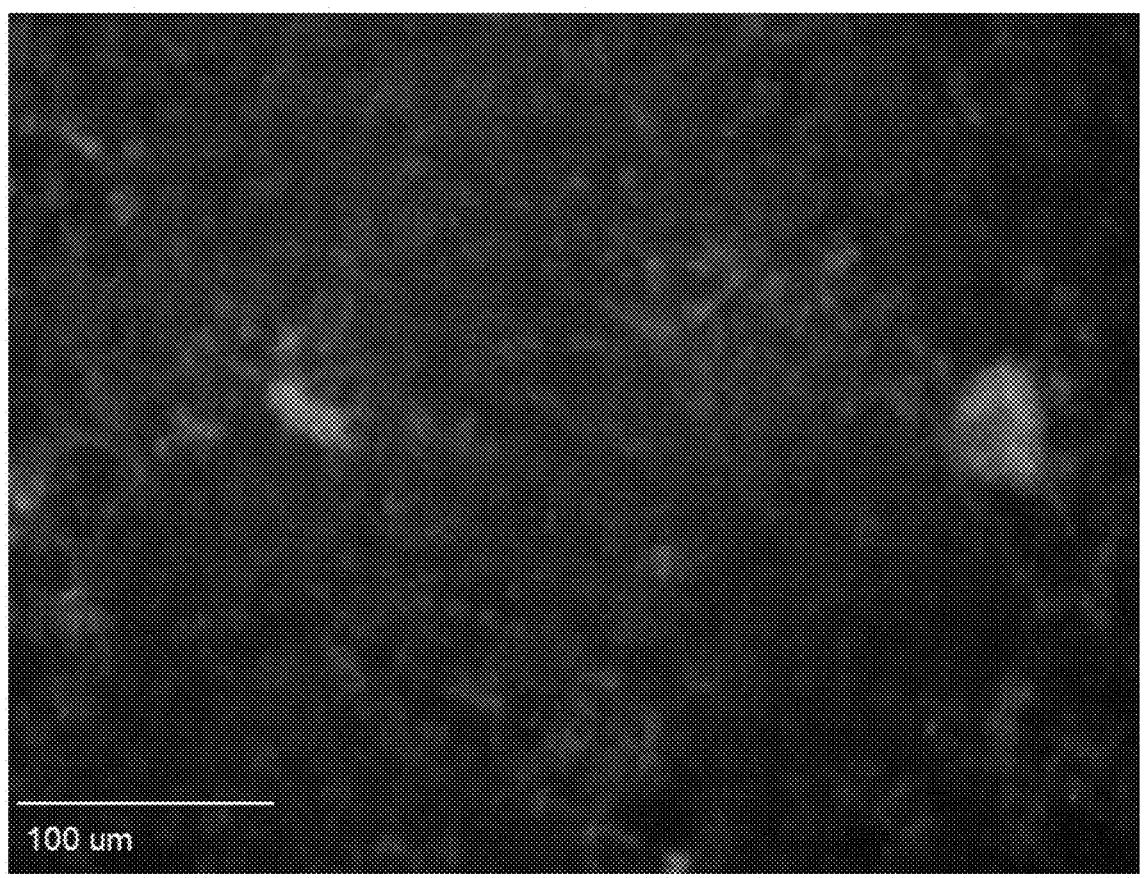
FIG. 14. IPS Cells Converted to Neural Progenitor Cells Immunofluorescent for Paired box protein Pax-6. Neural progenitor cells are derived from the ectoderm during neurulation, which is the first developmental event to give rise to a specific line of tissue, neural tissue. Neural Progenitor cells give rise to neurons and glia, through processes of neurogenesis and gliogenesis. Pax-6 is a regulatory transcription factor important for brain development and is a neural progenitor cell marker, whose expression is largely lost after neurogenesis or gliogenesis.

Cells were then fixed with 4% paraformaldehyde and immunocytochemistry was performed for neural progenitor cell markers PAX-6 and/or Nestin. FIG. 13 depicts fluorescent-nestin positive neural progenitor cells derived from IPSCs which were in turn derived from HFF. FIG. 14 depicts fluorescent-PAX-6 positive neural progenitor cells derived from IPSCs which were in turn derived from HFF. The presence of fluorescent-nestin and fluorescent-PAX-6-stained cells demonstrates that HFF cells can be reprogrammed into IPSCs because the IPSCs have the capacity to differentiate into ectodermal cells such as neural progenitor cells.

Example 16: IPSCs Derived from HFF Cells can Differentiate into Definitive Endodermal Cell For differentiation of IPSCs into endoderm cells, IPSCs were first washed in pre-warmed 1× Dulbecco's Phosphate Buffered Saline (DPBS); DPBS was then removed, and 1× Versene at room temperature was added to the IPSCs, and cells were allowed to rest for 10 min Thereafter, the 1× Versene was removed and Cellular Engineering Technology's IPSC growth media was added. Cells were triturated to create cell clumps of approximately 100-200 cells and were plated onto a 3.5 cm round bottom dish previously coated with 1.44 mL-1.92 mL of Matrigel (Corning Cat. No. 356234). Cells were placed in an incubator at 37° C., 95% humidity, and 5% $CO_2$ for 24 hours, and then fed by replacing the IPSC Growth Media with fresh IPSC Growth Media every 24 hours until 85% to 90% confluency on the plate surface is met.

After two days, room-temperature Cellular Engineering Technology's Definitive Endoderm Differentiation Media (Catalog No. CET.DIFF.DEM-250) was prepared by adding 10 mL of Cellular Engineering Technology's Definitive Endoderm Supplement to the Cellular Engineering Technology's Definitive Endoderm Base Media. The IPSC growth media was removed from the IPSCs and 2 mL of the pre-mixed, room-temperature Cellular Engineering Technology's Definitive Endoderm Differentiation Media was added. Cells were then fed every 48 hours by replacing the premixed Cellular Engineering Technology's Definitive Endoderm Differentiation Media on the cells with fresh premixed Cellular Engineering Technology's Definitive Endoderm Differentiation Media at room temperature, and placing the cells back in the 37° C. incubator.

Figure 15:
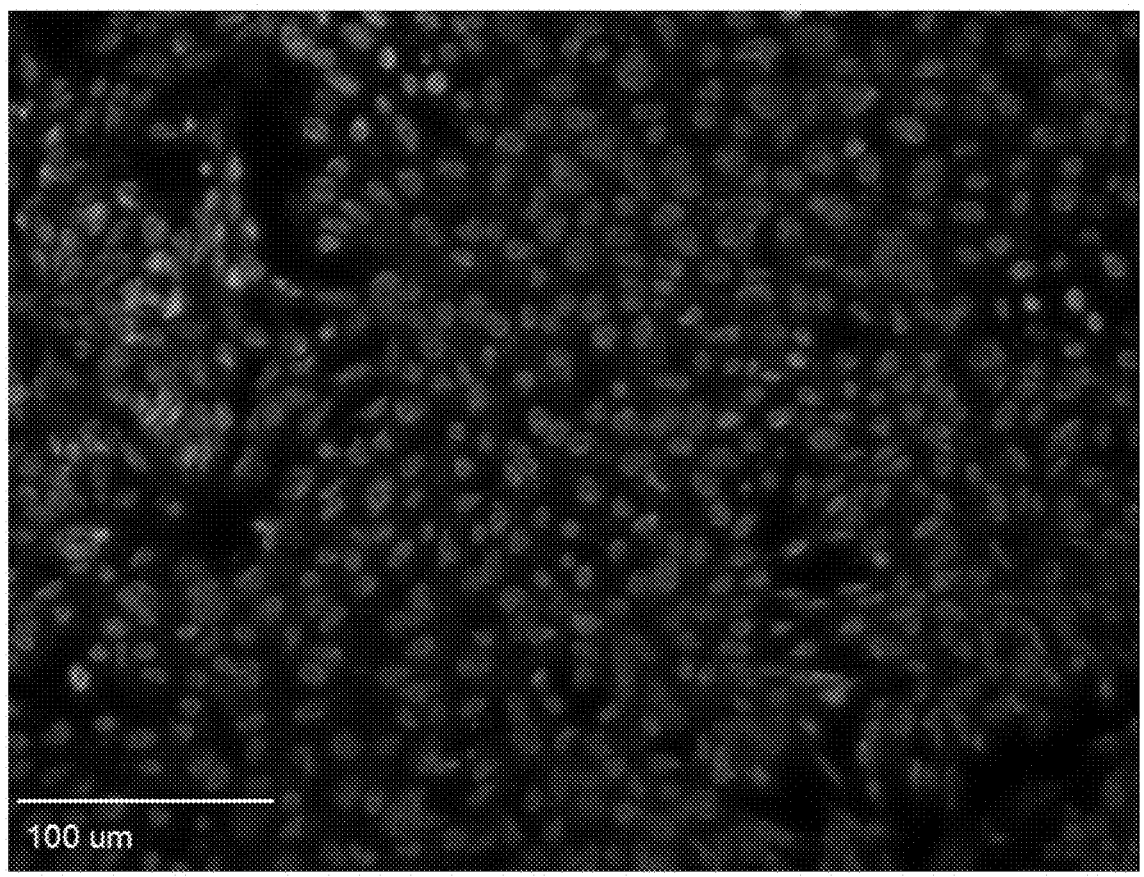
FIG. 15. IPS Cells Converted to Endoderm Immunofluorescent for SRY-box 17 (Sox-17). Endoderm is the innermost layer of the gastrula and responsible for the origination of the alimentary canal, lung cells, endocrine glands, liver cells, and pancreatic cells. SRY-box 17 protein is a transcription factor regulating embryonic development of endodermal cells.
Figure 16:
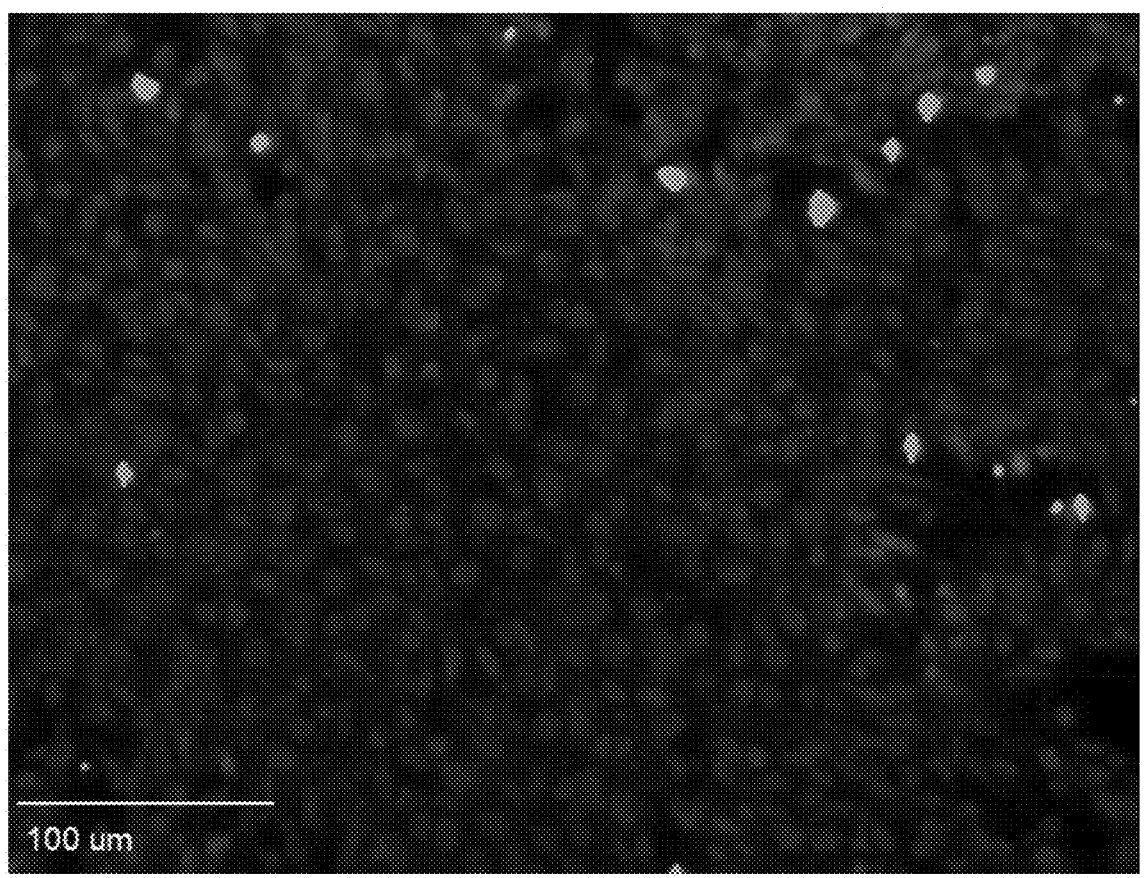
FIG. 16. IPS Cells Converted to Endoderm Immunofluorescent for Forkhead Box Protein A2 (FOXA2). Endoderm is the innermost layer of the gastrula and responsible for the origination of the alimentary canal, lung cells, endocrine glands, liver cells, and pancreatic cells. FOXA2 protein is a transcription factor regulating embryonic development of endodermal cells, particularly in the liver and pancreas.

After 4 days in premixed Cellular Engineering Technology's Definitive Endoderm Differentiation Media, the cells were fixed with 4% paraformaldehyde and fluorescent immunocytochemistry for SOX-17 and/or FOXA2 protein using the antibody manufacturer's protocol. See for example Santa Cruz Biotechnology, Inc. SOX-17 3.5CH antibody (Catalog No. SC-130295) available at, for example, www.scbt.com/scbt/product/sox-17-antibody-3-5ch. See also for example Abcam, Inc. FOXA2 antibody EPR4466 (Catalog No. ab108422) available at, for example, www.abcam.com/foxa2-antibody-epr4466-ab108422.html. FIG. 15 depicts anti-SOX-17-fluorescent endoderm cells wherein a green fluorophore conjugated secondary antibody is bound to the SOX-17 antibody, and the cells were derived from IPSCs which were in turn derived from HFF. FIG. 16 depicts anti-FOXA2-fluorescent endoderm cells wherein a green fluorophore conjugated secondary antibody is bound to the FOXA2 antibody, and the cells were derived from IPSCs which were in turn derived from HFFs. The presence of SOX-17-fluorescent cells and FOXA2-fluorescent cells demonstrate that HFF cells can be reprogrammed into IPSCs because the IPSCs have the capacity to differentiate into definitive endoderm cells. Because the same SSEA4-positive reprogrammed cells derived from HFFs could differentiate into mesodermal, ectodermal, and endodermal cells, the SSEA4-positive reprogrammed cells derived from HFFs are pluripotent.

Example 17: Isolation of Mononuclear Cells from Cord Blood and Peripheral Blood

Cultured neonatal mononuclear cells were isolated from discarded cord blood. Cord blood was obtained under an informed consent from parents that underwent routine normal deliveries from a local hospital. Additionally, five milliliters of whole blood were obtained by venipuncture from a 7-year-old male Cystic Fibrosis patient that carried a homozygous delta 508 mutation. A similar amount of blood was obtained from a 57-year-old female with A1ATD carrying a ZZ-phenotype. Clinical procedures were approved by the John Paul II Medical Research Institute Institutional Review Board (IRB). Isolated cultured cells were de-identified in accordance with IRB procedures such that researchers that processed tissue samples were not aware of the donor's identity. Whole blood was collected during venipuncture using standard vacutainer tubes containing EDTA. Whole blood was diluted 1:1 using Dulbecco's Phosphate Buffered Saline (DPBS). PBMC's were isolated using the Ficoll-Paque technique density based centrifugation. Briefly, 16 mL of Ficoll-Paque solution was pipetted into a Leucosep Tube. The tube was spun at 1000×g for 30 seconds at 20° C. The Ficoll-Paque was located below the porous barrier. The diluted whole blood was layered above the Styrofoam frit in the Leucosep tube and the sample was spun at 1000×g for 10 minutes at 20° C. The middle (white) layer, consisting of PBMC's, was collected using a serological pipette. The collected layer was mixed with an equal volume of DPBS, mixed and centrifuged at 300×g for 10 minutes at 20° C. The supernatant was aspirated and cells were resuspended in 300 microliters of DPBS and counted using a Millipore Scepter counter.

Figure 17:
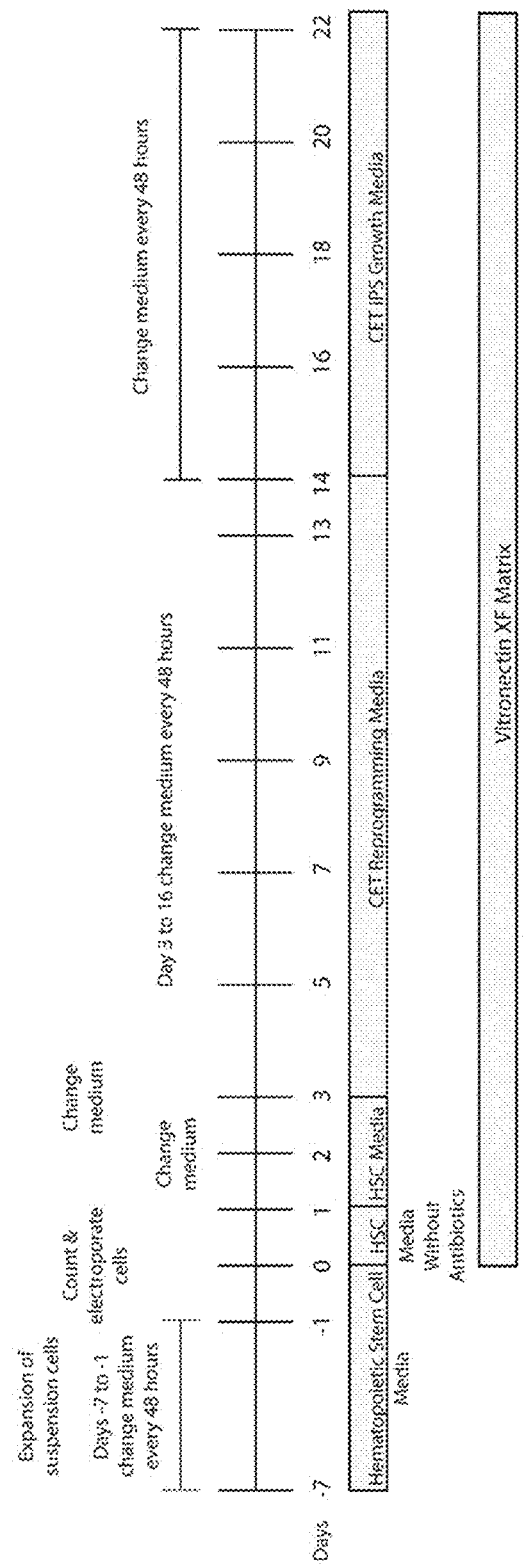
FIG. 17. Time sequence of hematapoetic stem cell media exposure, IPSC reprogramming, and cell expansion of cultured cord blood-derived mononuclear cell (CBDMNC).
Figure 18:
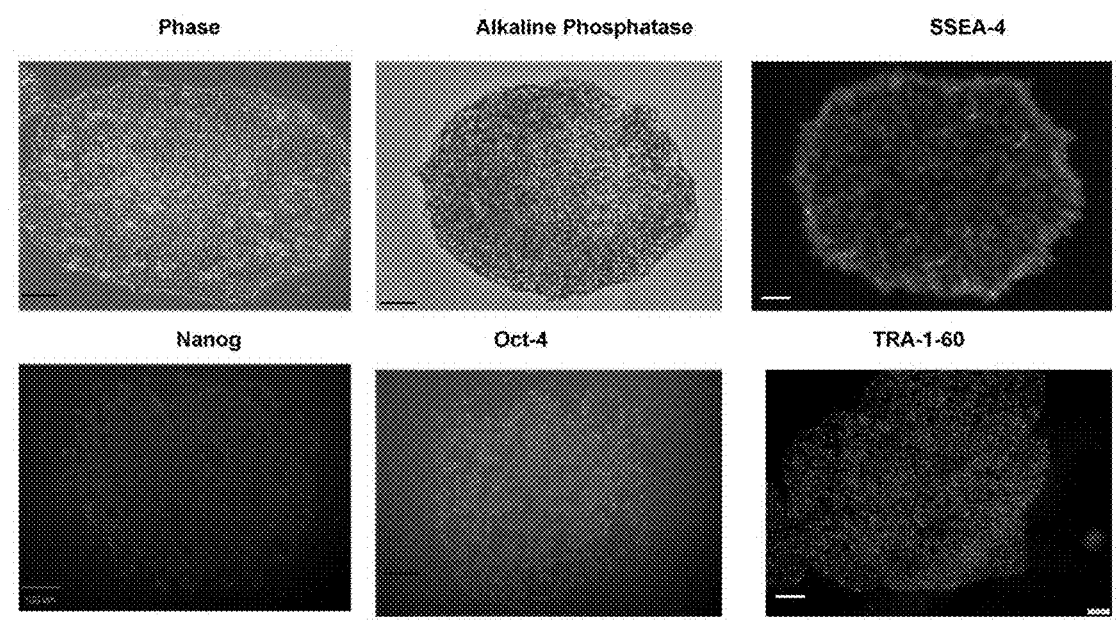
FIG. 18. Montage of cultured cord blood-derived mononuclear cell (CBDMNC) HSC cultured in differentiation media and then reprogrammed into IPSCs by transfecting with episomal vectors free of Myc and Lin28 and culturing in the presence of reprogramming media and IPSC reprogramming-assistance factors, PS48, A83-01, and sodium butyrate. Images were captured 22 days after transfection with episomal vectors. Typical IPSC colony depicted by phase contrast microscopy. Representative IPSC colony stained for alkaline phosphatase. Representative IPSC colony exhibited pluripotency by immunofluorescent live stain for SSEA4, Nanog, Oct4 and TRA160. Each figure is representative of 4 separate experiments. Scale bar represents 100 microns.

PBMCs were then exposed to hematopoetic stem cell media (HSC) differentiation media with antibiotics for 7 days. Next, cells were placed into HSC differentiation media without antibiotics and were electroporated according to Examples 2 and 4 above. After 24 hours, cell media was changed to HSC media with antibiotics, and the HSC media with antibiotics was replaced again after 24 hours (2 days after transfection). Three days after transfection, the media was replaced with Reprogramming media. IPSC Reprogramming media comprised 1×DMEM/F12 with HEPES (ThermoFisher Scientific, Waltham, Mass.), 1×N-2 Supplement (ThermoFisher Scientific, Waltham, Mass.), 1×B-27 Supplement (ThermoFisher Scientific, Waltham, Mass.), 1×MEM Non-Essential Amino Acids (ThermoFisher Scientific, Waltham, Mass.) 1× Glutamax ((ThermoFisher Scientific, Waltham, Mass.)) and 1× Beta-Mercaptoethanol (ThermoFisher Scientific, Waltham, Mass.). The IPSC Reprogramming media was admixed with the following reprogramming-assistance factors: Sodium Butyrate (Reagents Direct, Encinitas, Calif.), A83-0-1 (Reagents Direct, Encinitas, Calif.), and PS48 (Reagents Direct, Encinitas, Calif.), and further admixed with ascorbic acid (Sigma-Aldrich, St. Louis, Mo.) and Human Recombinant FGF-2 (Peprotech, Rocky Hill, N.J.). Cells were fed every 48 hours, replacing the old IPSC Reprogramming media containing the above Reprogramming-assistance factors, FGF-2, and ascorbic acid. Fourteen days after transfection, the media was then replaced with IPSC Reprogramming media without the above reprogramming-assistance factors but with FGF-2, until 22 days after transfection. At 22 days after transfection, the cells were subjected to experiments in Examples 18-22 below and were exposed to immunofluorescence labeling for Nanog, Oct-3/4, TRA160, and SSEA-4 Live Stain (ThermoFisher Scientific, Waltham, Mass., discontinued; Stemgent, Cambridge, Mass. Catalog No. 09-0097) and Alkaline Phosphatase (Catalog No. 00-0055, Stemgent, Cambridge, Mass.) as in Example 5 above. FIG. 17 depicts the timeline of the PBMCs to HSC media, transfection, and reprogramming media with and without reprogramming-assistance factors described above. FIG. 18 depicts colonies immunofluorescent for Nanog, Oct-3/4, TRA160, and positive for SSEA-4 Live Stain and Alkaline Phosphatase stain after being reprogrammed into IPSC with episomal vectors free of Myc and Lin28 and cultured in IPSC reprogramming media in the presence of IPSC reprogramming-assistance factors, PS48, A83-01, and sodium butyrate, and HSC differentiation media.

Example 18: Flow Cytometry

Flow cytometry was conducted using a Guava EasyCyte HT. Cells were dissociated using Trypsin Like Enzyme (Tryp-LE) for 10 minutes at 37° C. Dissociated cells were pipetted to remove aggregations and clumps and passed through a 70-micron filter. Single cell suspensions were counted using a Millipore Scepter counter and cell density was adjusted to $1×10^5$ cells/100 microliters. 5 microliters of appropriate antibody was added to the dissociated cells and mixed using gentle pipetting. This was then incubated in the dark for 30 minutes on ice. At the end of this incubation period, labeled cells were washed with 1× ice cold DPBS and resuspended in 200 microliters DPBS. Cells were then counted using a Guava EasyCyte HT. Viable cells were gated using a log/log Forward Scatter/Side Scatter plot. Each IPSC marker fluorescence was also compared to its IgKappa Isotype control to quantify non-specific and auto-fluorescence events. Each IPSC marker was counted and plotted as a graph with the abscissa containing the log Fluorescence of a given marker and the ordinate containing the counts of either a negative or positive viable gated cell. This graph was then used to create histograms providing percentages of negative and positive cells. Based on the IgKappa Isotype control, $10^2$ was used as the cutoff in log Fluorescence between a negative and a positive cell.

Example 19: Morphology of IPSC Colonies Derived from CBDMNCs

Myc/Lin28-free IPSC colonies derived from CBDMNC exhibited the typical flat shape and refractile border as shown under phase microscopy (FIG. 18). IPSC colonies also stain positive for alkaline phosphatase (FIG. 18). Colonies also expressed pluripotent biomarkers that include SSEA4, Nanog, Oct4 and TRA160 (FIG. 18), which confirm that the reprogramming process resulted in fully reprogrammed cells.

Figure 19:
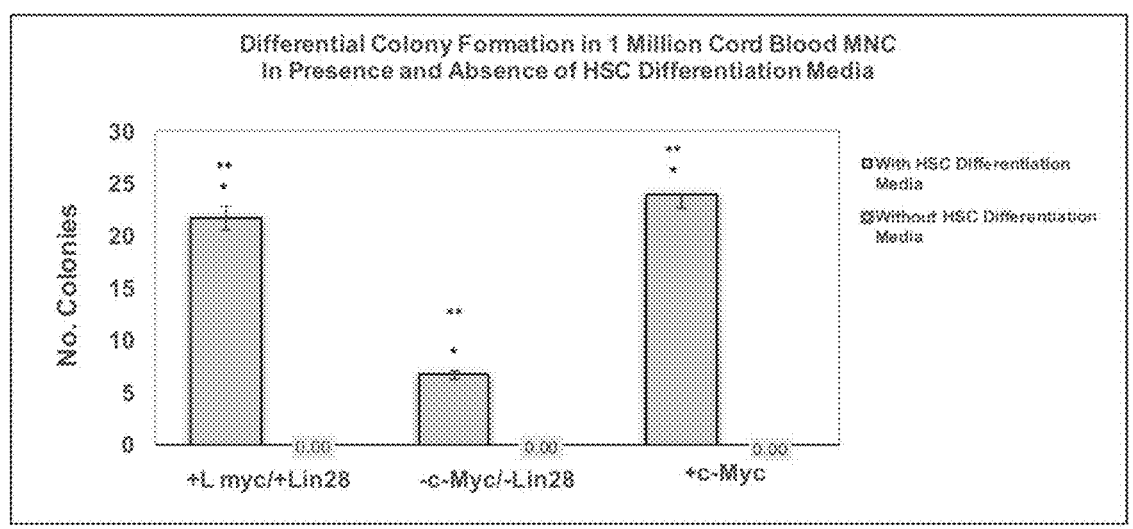
FIG. 19. Numbers of colonies generated from CBDMNCs transfected with 1) 1-Myc plus Lin28, 2) c-Myc, or 3) where 1-Myc, Lin28, and c-Myc were omitted, then cultured in the presence and absence of HSC differentiation media. Each test condition used 1,000,000 input cells. (Mean±SEM number of colonies with a sample size of 4. Data labeled with "*" show a statistical significant difference (p<0.05) between cultured cells treated in the presence and absence of HSC differentiated media. Data labeled with "**" depicts a significant difference in colony formation between Myc and Lin28 and those cells treated without Myc and Lin28.)

Example 20: Effect of Reprogramming-Assistance Factors on IPSC Colony Formation from CBDMNCs HSC differentiation was necessary to reprogram CBDMNC into IPSC. The number of colonies were measured in c-Myc, 1-Myc/Lin28 and Myc/Lin28-free groups pretreated in the presence and absence of HSC differentiation media. There was IPSC colony formation in all three groups pretreated with HSC differentiation media. There were statistically more observed colonies in cells treated with Myc and Lin28 than in Myc/Lin28-free cells (FIG. 19). However, there were no observed colonies in groups that were not pretreated with HSC differentiation media regardless in the presence and absence of Myc/Lin28. Taken together, these data indicate that CBDMNC conversion into IPSC required preceding HSC differentiation.

Figure 20A:
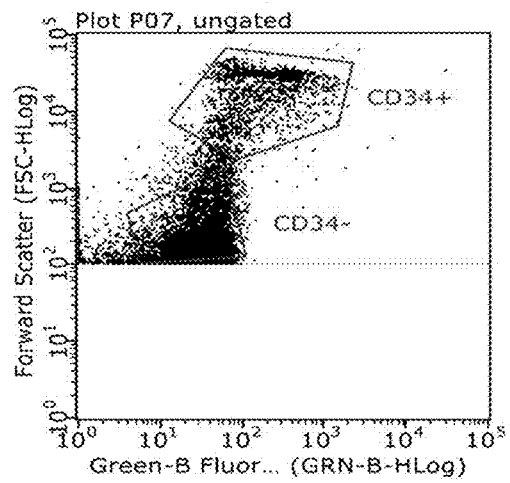
FIGS. 20A-20C. CD34+ cells converted from CBDMNCs in the presence of HSC differentiation media as quantified by flow cytometry. Cultured CBDMNC were exposed to 7 days of HSC differentiation media and the amount of HSC differentiation was quantified by an antibody against human CD34+ cell expression.
Figure 20B:
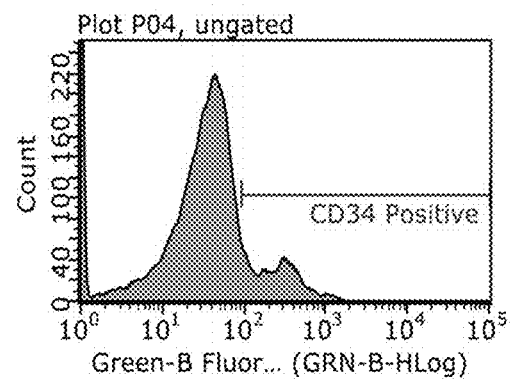
Figure 20C:
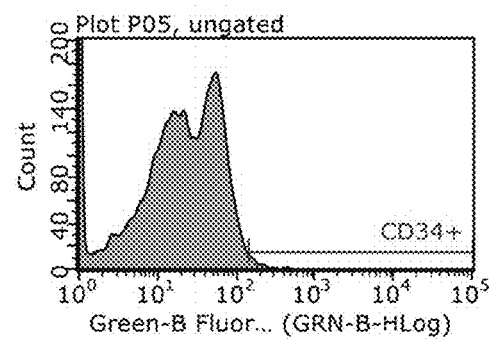

Example 21: Flow Cytometry of CBDMNC after HSC Conversion to Generate CD34+ Cells HSC conversion from CBDMNC was further quantitated by flow cytometry. Cultured CBDMNC were exposed to 7 days of HSC differentiation media and the amount of HSC were quantified by an antibody against human CD34+ cell expression. A dot blot is illustrated in FIG. 20A which identified two separate population CD34+ cells and CD34− cells. FIG. 20B depicts a histogram which demonstrated that 13 percent of CBDMNC cells are converted into CD34+ cells. In contrast, CD34+ cells represented only 1 percent of the unstimulated cultured CBDMNC (FIG. 20C). These results indicate that CD34+ cell expression is required before IPSC reprogramming. Further, these results indicate only a small a fraction of the total cellular population is necessary to achieve IPSC conversion.

Figure 21:
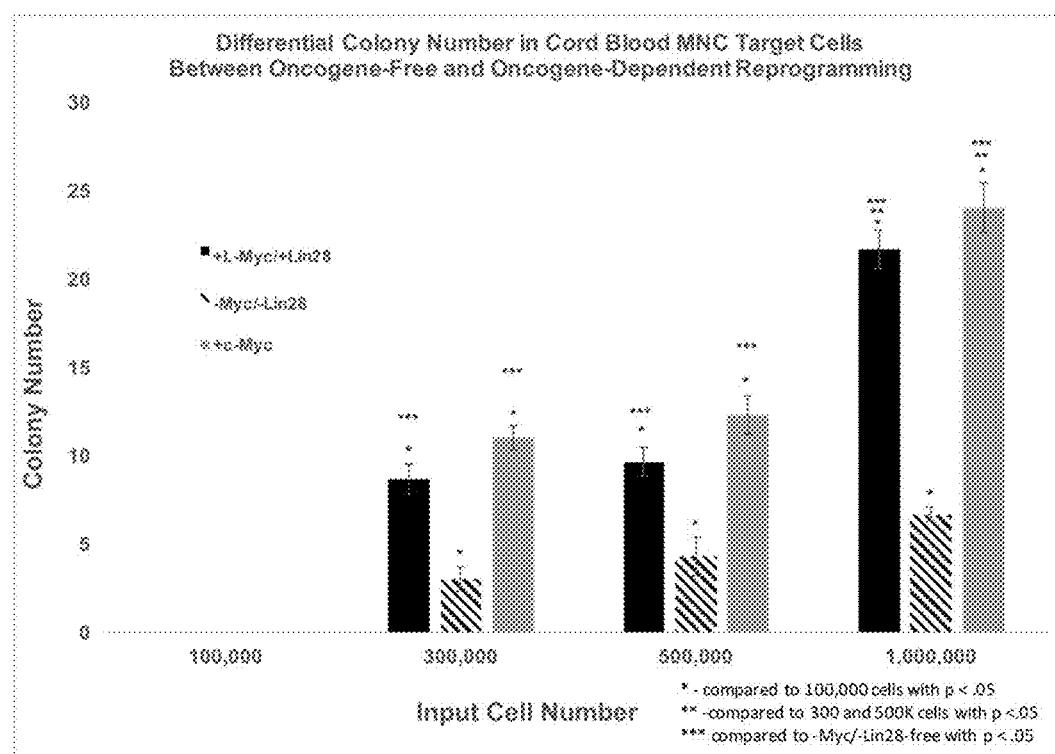
FIG. 21. Number of IPSC Colonies Depend upon the Input Number of CBDMNCs, and transfection of c-Myc, 1-Myc and Lin 28, or the absence of c-Myc, 1-Myc, and Lin28. (Mean±SEM of number of colonies, n=4, ANOVA, and Tukey's HSD, *: p<0.05 compared to 100,000 input cells of the same vector construct. : p<0.05 compared to 300,000 input cells of the same vector construct. *: p<0.05 with transfection of Myc and/or Lin28 compared to the absence of Myc and Lin28 transfection at the same corresponding input cell number.)

Example 22: Effect of the Number of Input CBDMNCs and c-Myc, or L-Myc+Lin28, or Oncogene Free Conditions on Reprogramming An observed dose-dependent increase in colony number as a function of input cell number. The number of IPSC colonies were compared in CBDMNC transformed in the presence and absence of Myc and Lin28 (FIG. 21) at input cell number between 100,000 and 1,000,000. There were no IPSC colonies formed at 100,000 input cells. A minimum of 300,000 input cells was necessary to produce IPSC colonies regardless of whether Myc/Lin28 was used or not. We also observed a statistically higher number of colonies with input cell numbers of 500,000 and 1,000,000 than at input cell numbers of 300,000 cells regardless of the presence or absence of Myc and Lin28. Further, there was a statistically significant difference in the number of colonies between Myc/Lin28 treated cells and cultured cells treated in the absence of these oncogenes (FIG. 21).

Figure 22:
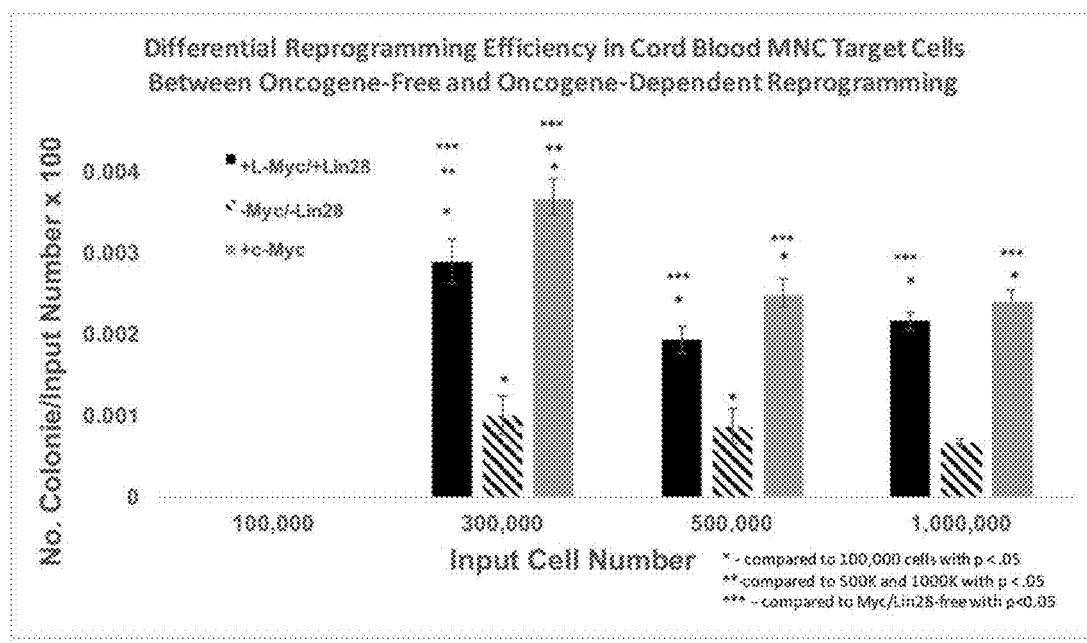
FIG. 22. Reprogramming Efficiency depends upon whether L-Myc, c-Myc, or Lin28 were Transfected in Addition to Sox-2, Klf-4, Oct3/4 into cultured CBDMNC and not Input Cell Numbers. The number of input cells varied from 100,000; 300,000; 500,000; and 1,000,000 CBDMNCs. (Mean±SEM of reprogramming efficiency, ANOVA, Tukey's HSD, n=4, "*": (p<0.05) compared to 100,000 input cells of the same vector construct; "": (p<0.05) compared to 300,000 input cells of the same vector construct; "*": (p<0.05) in cultured cells transfected with exogenous Myc and Lin28 compared to cells not transfected with L-Myc, c-Myc, and Lin28 at each corresponding input cell number.)

Moreover, the reprogramming efficiency was observed at a maximum at 300,000 input cells when expressed as the number of colonies per number of CBDMNC input number× 100 (FIG. 22) regardless of whether reprogrammed in the presence or absence of Myc/Lin28. As anticipated, the reprogramming efficiency was statistically higher in CBDMNC that were reprogrammed with Myc and Lin28 than in the absence of these oncogenes.

Figure 23:
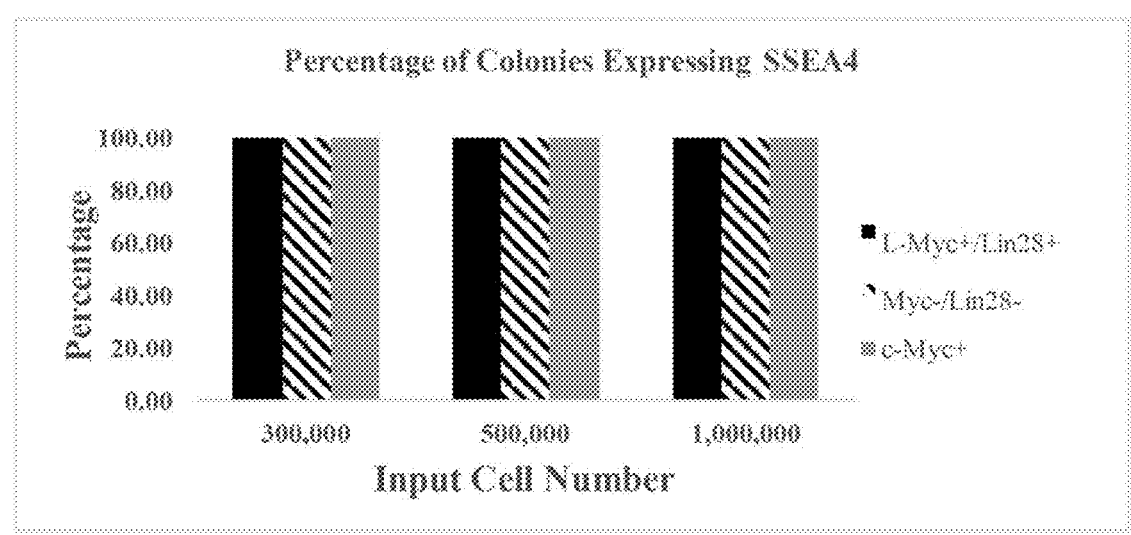
FIG. 23. IPSC Colonies from CBDMNC Conversion with Reprogramming-assistance Factors, PS48, A83-01, and sodium butyrate, and HSC differentiation media are all Fully Reprogrammed Regardless in the Presence and Absence of Myc/Lin28. Figure depicts the percentage of colonies that express SSEA4 among cultured CBDMNC exposed to L-Myc/Lin28, c-Myc and the absence of both oncogene groups. Data are reported as the mean (the standard error=0). All colonies stained positive for SSEA4. Each group represents a sample size of 4 replicates. Full pluripotency was achieved at 300,000, 500,000 and 1,000,000 input cells.

Despite the differential colony counts and reprogramming efficiency in CBDMNC treated in the presence and absence of Myc/Lin28, there was no significant difference in the percentage of colonies that were fully reprogrammed. Based on the expression of SSEA4, 100 percent of all colonies expressed SSEA4 with a standard error=0 (FIG. 23). These effects were observed at input cells of 300,000, 500,000 and 1,000,000. Taken together with the results of FIG. 22, there was no advantage in reprogramming efficiency with cultured CBDMNC at cell input numbers that exceeded 300,000 cells.

Figure 24:
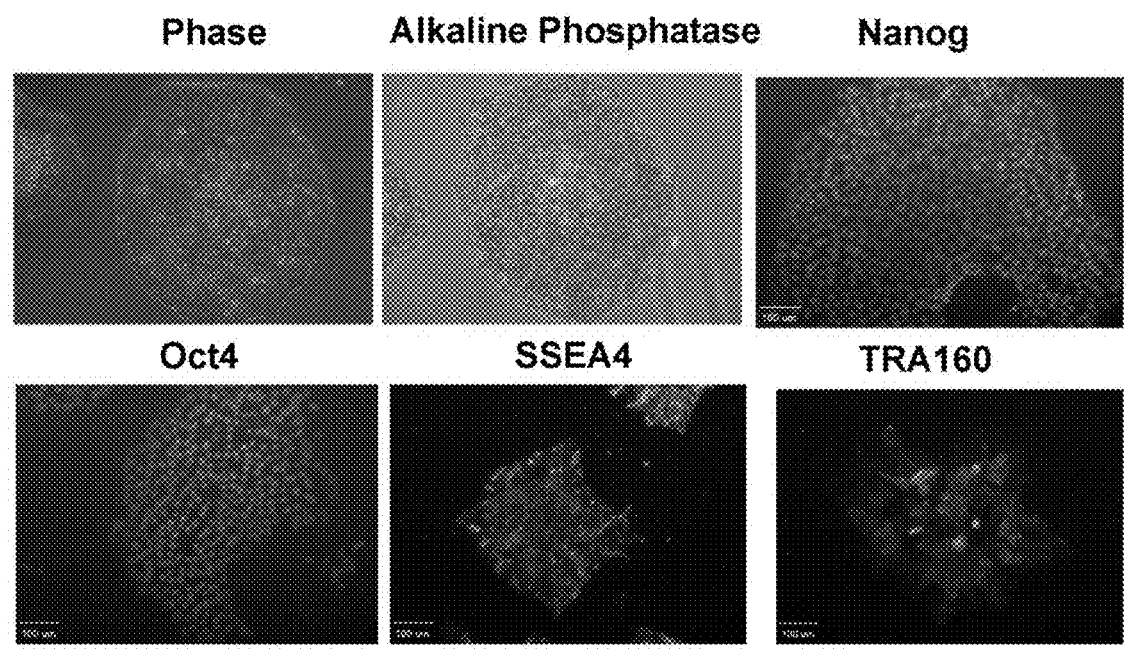
FIG. 24. Montage of cultured IPSCs reprogrammed with peripheral blood MNC from a 57-year-old Caucasian female with alpha 1 antitrypsin deficiency with a PiZZ phenotype. Cells were reprogrammed into IPSC with episomal vectors free of Myc and Lin28 and HSC differentiation media. Images were captured at day 14 of the IPSC reprogramming process. Typical IPSC colony depicted by phase contrast microscopy. Representative IPSC colony stained positive for alkaline phosphatase. Representative IPSC colonies exhibited pluripotency by immunofluorescent live stain for SSEA4, Nanog, Oct4 and TRA160. Each figure is representative of 4 separate experiments. Scale bar represents 100 microns.

Example 23: Reprogramming of Peripheral Blood MNC from 57-Year-Old with Alpha1 Antitrypsin Deficiency with a PiZZ Phenotype Peripheral blood MNC cells from a 57-year-old Caucasian female with alpha 1 antitrypsin deficiency with a PiZZ phenotype were reprogrammed into IPSC with episomal vectors free of Myc and Lin28 and HSC differentiation media using the protocols and materials of Examples 17 above. FIG. 24 depicts colonies captured 14 days after transfection. Typical IPSC colony depicted by phase contrast microscopy. Representative IPSC colony stained positive for alkaline phosphatase. Representative IPSC colonies exhibited pluripotency by immunofluorescent live stain for SSEA4, Nanog, Oct4 and TRA160. Each panel is representative of 4 separate experiments. Scale bar represents 100 microns.

Figure 25:
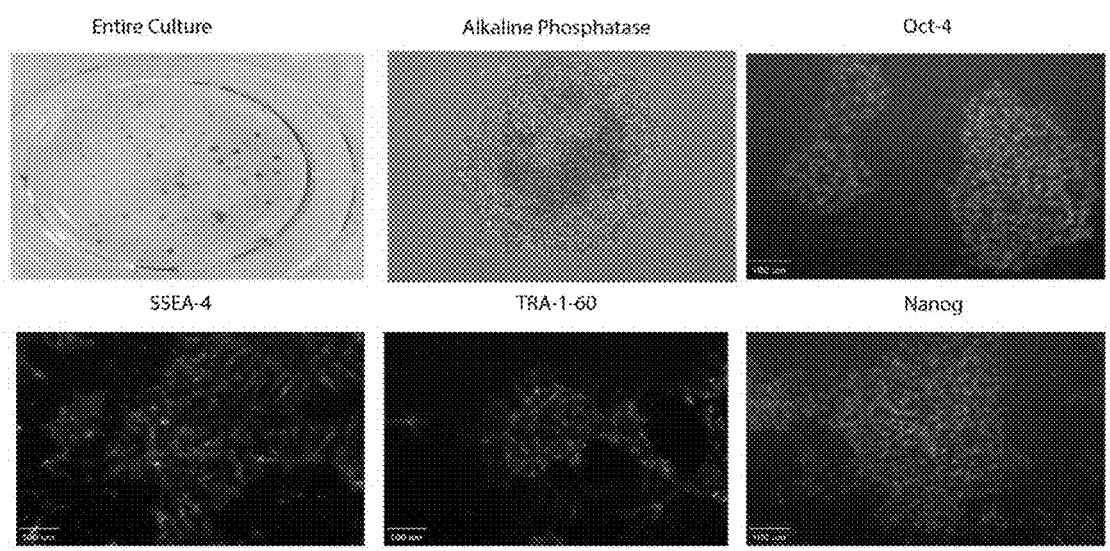
FIG. 25: Montage of cultured IPSCs reprogrammed from peripheral blood MNC among a 7-year-old Caucasian male with Cystic Fibrosis with the delta 508 mutation. Cells were reprogrammed into IPSC with episomal vectors free of Myc and Lin28 and HSC differentiation media. Images were captured at day 14 of the IPSC reprogramming process. Representative image of an entire culture stained with alkaline phosphatase. Representative IPSC colony stained for alkaline phosphatase. Representative IPSC colonies exhibited pluripotency by immunofluorescent live stain for SSEA4, Nanog, Oct4 and TRA160. Each figure is representative of 4 separate experiments. Scale bar represents 100 microns.

Example 24: Reprogramming of Peripheral Blood MNC from a 7-Year-Old with Cystic Fibrosis and a Delta 508 Mutation Peripheral blood MNC cells from a 7-year-old Caucasian male with Cystic Fibrosis with the delta 508 mutation were reprogrammed into IPSC with episomal vectors free of Myc and Lin28 and HSC differentiation media using the protocols and materials of Examples 17 above. FIG. 25 depicts colonies captured 14 days after transfection. Representative image of an entire culture stained with alkaline phosphatase. Representative IPSC colony stained for alkaline phosphatase. Representative IPSC colonies exhibited pluripotency by immunofluorescent live stain for SSEA4, Nanog, Oct4 and TRA160. Each panel is representative of 4 separate experiments. Scale bar represents 100 microns.

What is claimed is:

1. A method for reprogramming a somatic cell into an induced pluripotent stem (iPS) cell in vitro comprising:
   expressing exogenous sex determining region Y-box 2 (Sox-2), Kruppel-like factor 4 (Klf-4), and octamer-binding transcription factor 3/4 (Oct3/4) in the somatic cell from DNA that has not integrated into genomic DNA of the somatic cell; and
   culturing the somatic cell in a reprogramming medium comprising an exogenous activating receptor-like kinase 5 (Alk-5) inhibitor, an exogenous histone deacetylase inhibitor, an exogenous activator of glycolysis, and ascorbic acid to obtain an iPS cell.

2. The method according to claim 1, wherein the method further comprises expressing exogenous Epstein-Bar nuclear antigen-1 (EBNA-1) in the somatic cell from DNA that has not integrated into the genomic DNA of the somatic cell, and wherein the DNA that has not integrated into the genomic DNA of the somatic cell comprises at least one plasmid with an Epstein-Barr virus origin of replication (oriP).

3. The method according to claim 2, which yields an integration-free, virus-free, exogenous oncogene-free iPS cell.

4. The method according to claim 3, wherein the iPS cell is a human iPS cell.

5. The method according to claim 3, wherein the iPS cell is differentiated into an endodermal, mesodermal, or ectodermal cell.

6. The method according to claim 1, wherein one or more of lung myelocytomatosis oncogene (L-Myc), c-myelocytomatosis oncogene (c-Myc), Lin28, simian virus 40 large T antigen, and Nanog are not exogenously expressed.

7. The method according to claim 6, wherein the reprogramming efficiency exceeds 0.0006%.

8. The method according to claim 6, wherein the reprogramming efficiency exceeds 0.001%.

9. The method according to claim 1, further comprising maintaining the cell in a dedifferentiation maintenance medium comprising basic fibroblast growth factor and transforming growth factor beta after being cultured in the reprogramming medium.

10. The method according to claim 1, wherein the culturing does not require feeder cells.

11. The method according to claim 1, which further comprises inhibiting p53 activity in the somatic cell.

12. The method according to claim 11, wherein inhibiting p53 activity in the somatic cell comprises suppressing p53 expression in the somatic cell, inhibiting p53-induced cell cycle arrest, and/or p53-induced apoptosis.

13. The method according to claim 12, wherein suppressing p53 expression comprises expressing antisense p53 RNA in the somatic cell from DNA that has not integrated into the genomic DNA of the somatic cell.

14. The method according to claim 1, wherein
the Alk-5 inhibitor comprises 3-(6-Methyl-2-pyridinyl)-N-phenyl-4-(4-quinolinyl)-1H-pyrazole-1-carbothioamide (A83-01);
the histone deacetylase inhibitor comprises sodium butyrate or valproic acid; and
the activator of glycolysis comprises a phosphoinositide-dependent protein kinase-1 inhibitor selected from 5-(4-Chloro-phenyl)-3-phenyl-pent-2-enoic acid (PS48); α,α,-Dimethyl-4-[2-methyl-8-[2-(3-pyridinyl)ethynyl]-1H-imidazo[4,5-c]quinolin-1-yl]-benzeneacetonitrile (BAG956); N-[3-[[5-Iodo-4-[[3-[(2-thienylcarbonyl)amino]propyl]amino]-2-pyrimidinyl]amino]phenyl]-1-pyrrolidinecarboxamide (BX795); (3S,6R)-1-[6-(3-Amino-1H-indazol-6-yl)-2-(methylamino)-4-pyrimidinyl]-N-cyclohexyl-6-methyl-3-piperidinecarboxamide (GSK 2334470); 2-Amino-N-[4-[5-(2-phenanthrenyl)-3-(trifluoromethyl)-1H-pyrazol-1-yl]phenyl]acetamide (OSU03012); and 4-Dodecyl-N-1,3,4-thiadiazol-2-yl-benzenesulfonamide (PHT427).

15. The method according to claim 1, wherein the somatic cell is an isolated cord blood or peripheral blood mononuclear cell, and wherein the method further comprises pre-culturing the isolated cord blood or peripheral blood mononuclear cell in hematopoietic stem cell expansion media.

16. The method according to claim 1, the somatic cell being free of exogenous oncogenes and retroviruses.

17. The method according to claim 1, wherein colonies of iPS cells are obtained and 100% of the colonies express stage-specific embryonic antigen-4 (SSEA-4).

18. The method according to claim 1, the somatic cell being an adherent cell.

19. The method according to claim 1, wherein
the Alk-5 inhibitor comprises 3-(6-Methyl-2-pyridinyl)-N-phenyl-4-(4-quinolinyl)-1H-pyrazole-1-carbothioamide (A83-01);
the histone deacetylase inhibitor comprises sodium butyrate; and
the activator of glycolysis comprises 5-(4-Chloro-phenyl)-3-phenyl-pent-2-enoic acid (PS48).

\* \* \* \* \*

SEQUENCE LISTING

<160> NUMBER OF SEQ ID NOS: 22

<210> SEQ ID NO 1
<211> LENGTH: 1320
<212> TYPE: DNA
<213> ORGANISM: Homo sapiens

<400> SEQUENCE: 1

| | | | | | |
|---|---|---|---|---|---|
| atgcccctca | acgttagctt | caccaacagg | aactatgacc | tcgactacga | ctcggtgcag | 60 |
| ccgtatttct | actgcgacga | ggaggagaac | ttctaccagc | agcagcagca | gagcgagctg | 120 |
| cagcccccgg | cgcccagcga | ggatatctgg | aagaaattcg | agctgctgcc | caccccgccc | 180 |
| ctgtccccta | gccgccgctc | cgggctctgc | tcgccctcct | acgttgcggt | cacacccttc | 240 |
| tcccttcggg | gagacaacga | cggcggtggc | gggagcttct | ccacggccga | ccagctggag | 300 |
| atggtgaccg | agctgctggg | aggagacatg | gtgaaccaga | gtttcatctg | cgacccggac | 360 |
| gacgagacct | tcatcaaaaa | catcatcatc | caggactgta | tgtggagcgg | cttctcggcc | 420 |
| gccgccaagc | tcgtctcaga | gaagctggcc | tcctaccagg | ctgcgcgcaa | agacagcggc | 480 |
| agcccgaacc | ccgccgcgg | ccacagcgtc | tgctccacct | ccagcttgta | cctgcaggat | 540 |
| ctgagcgccg | ccgcctcaga | gtgcatcgac | ccctcggtgg | tcttcccta | ccctctcaac | 600 |
| gacagcagct | cgcccaagtc | ctgcgcctcg | caagactcca | cgcgccttctc | tccgtcctcg | 660 |
| gattctctgc | tctcctcgac | ggagtcctcc | ccgcagggca | gccccgagcc | cctggtgctc | 720 |
| catgaggaga | caccgcccac | caccagcagc | gactctgagg | aggaacaaga | agatgaggaa | 780 |
| gaaatcgatg | ttgttctgt | ggaaaagagg | caggctcctg | gcaaaaggtc | agagtctgga | 840 |
| tcaccttctg | ctggaggcca | cagcaaacct | cctcacagcc | cactggtcct | caagaggtgc | 900 |
| cacgtctcca | cacatcagca | caactacgca | gcgcctccct | ccactcggaa | ggactatcct | 960 |
| gctgccaaga | gggtcaagtt | ggacagtgtc | agagtcctga | gacagatcag | caacaaccga | 1020 |
| aaatgcacca | gccccaggtc | ctcggacacc | gaggagaatg | tcaagaggcg | aacacacaac | 1080 |
| gtcttggagc | gccagaggag | gaacgagcta | aaacggagct | ttttgccct | gcgtgaccag | 1140 |
| atcccggagt | tggaaaacaa | tgaaaaggcc | cccaaggtag | ttatccttaa | aaaagccaca | 1200 |
| gcatacatcc | tgtccgtcca | agcagaggag | caaaagctca | tttctgaaga | ggacttgttg | 1260 |
| cggaaacgac | gagaacagtt | gaaacacaaa | cttgaacagc | tacggaactc | ttgtgcgtaa | 1320 |

<210> SEQ ID NO 2
<211> LENGTH: 439
<212> TYPE: PRT
<213> ORGANISM: Homo sapiens

<400> SEQUENCE: 2

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
                20                  25                  30

Gln Gln Gln Gln Gln Ser Glu Leu Gln Pro Pro Ala Pro Ser Glu Asp
            35                  40                  45

Ile Trp Lys Lys Phe Glu Leu Leu Pro Thr Pro Pro Leu Ser Pro Ser
        50                  55                  60

Arg Arg Ser Gly Leu Cys Ser Pro Ser Tyr Val Ala Val Thr Pro Phe
65                  70                  75                  80

Ser Leu Arg Gly Asp Asn Asp Gly Gly Gly Ser Phe Ser Thr Ala
                85                  90                  95

Asp Gln Leu Glu Met Val Thr Glu Leu Leu Gly Gly Asp Met Val Asn
            100                 105                 110

Gln Ser Phe Ile Cys Asp Pro Asp Glu Thr Phe Ile Lys Asn Ile
        115                 120                 125

Ile Ile Gln Asp Cys Met Trp Ser Gly Phe Ser Ala Ala Lys Leu
    130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ser Glu Cys Ile Asp Pro Ser
            180                 185                 190

Val Val Phe Pro Tyr Pro Leu Asn Asp Ser Ser Ser Pro Lys Ser Cys
        195                 200                 205

Ala Ser Gln Asp Ser Ser Ala Phe Ser Pro Ser Ser Asp Ser Leu Leu
    210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
            260                 265                 270

Pro Gly Lys Arg Ser Glu Ser Gly Ser Pro Ser Ala Gly Gly His Ser
        275                 280                 285

Lys Pro Pro His Ser Pro Leu Val Leu Lys Arg Cys His Val Ser Thr
    290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
            340                 345                 350

Asn Val Lys Arg Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
            420                 425                 430

Gln Leu Arg Asn Ser Cys Ala
        435

<210> SEQ ID NO 3
<211> LENGTH: 1434
<212> TYPE: DNA
<213> ORGANISM: Homo sapiens

<400> SEQUENCE: 3
atgaacaatt cgcccttcac catggctgtc agtgacgcgc tgctcccatc tttctccacg    60
ttcgcgtctg gcccggcggg aagggagaag acactgcgtc aagcaggtgc cccgaataac   120
cgctggcggg aggagctctc ccacatgaag cgacttcccc cagtgcttcc cggccgcccc    180
tatgacctgg cggcggcgac cgtggccaca gacctggaga gcggcggagc cggtgcggct    240
tgcggcggta gcaacctggc gcccctacct cggagagaga ccgaggagtt caacgatctc    300
ctggacctgg actttattct ctccaattcg ctgacccatc ctccggagtc agtgccgcc     360 accgtgtcct cgtcagcgtc agcctcctct tcgtcgtcgc cgtcgagcag cggccctgcc    420
agcgcgccct ccacctgcag cttcacctat ccgatccggg ccgggaacga cccgggcgtg    480
gcgccgggcg gcacgggcgg aggcctcctc tatggcaggg agtccgctcc ccctccgacg    540
gctcccttca acctggcgga catcaacgac gtgagcccct cgggcggctt cgtggccgag    600
ctcctgcggc cagaattgga cccggtgtac attccgccgc agcagccgca gccgccaggt    660
ggcgggctga tgggcaagtt cgtgctgaag gcgtcgctga gcgcccctgg cagcgagtac    720
ggcagcccgt cggtcatcag cgtcagcaaa ggcagccctg acggcagcca cccggtggtg    780
gtggcgccct acaacggcgg gccgccgcgc acgtgcccca agatcaagca ggaggcggtc    840
tcttcgtgca cccacttggg cgctggaccc cctctcagca atggccaccg gccggctgca    900
cacgacttcc ccctggggcg gcagctcccc agcaggacta ccccgaccct gggtcttgag    960
gaagtgctga gcagcaggga ctgtcaccct gccctgccgc ttcctcccgg cttccatccc   1020 caccegggg ccaattaccc atccttcctg cccgatcaga tgcagccgca agtcccgccg   1080
ctccattacc aagagctcat gccacccggt tcctgcatgc cagaggagcc caagccaaag   1140 agggggaagac gatcgtggcc ccggaaaagg accgccaccc acacttgtga ttacgcgggc   1200
tgcggcaaaa cctacacaaa gagttcccat ctcaaggcac acctgcgaac ccacacaggt   1260
gagaaacctt accactgtga ctgggacggc tgtggatgga aattcgcccg ctcagatgaa   1320
ctgaccaggc actaccgtaa acacacgggg caccgcccgt tccagtgcca aaaatgcgac   1380
cgagcatttt ccaggtcgga ccacctcgcc ttacacatga agagacattt ttaa          1434

<210> SEQ ID NO 4
<211> LENGTH: 477
<212> TYPE: PRT
<213> ORGANISM: Homo sapiens

<400> SEQUENCE: 4

Met Asn Asn Ser Pro Phe Thr Met Ala Val Ser Asp Ala Leu Leu Pro
1               5                   10                  15

Ser Phe Ser Thr Phe Ala Ser Gly Pro Ala Gly Arg Glu Lys Thr Leu
            20                  25                  30

Arg Gln Ala Gly Ala Pro Asn Asn Arg Trp Arg Glu Glu Leu Ser His
        35                  40                  45

Met Lys Arg Leu Pro Pro Val Leu Pro Gly Arg Pro Tyr Asp Leu Ala
    50                  55                  60

Ala Ala Thr Val Ala Thr Asp Leu Glu Ser Gly Gly Ala Gly Ala Ala
65                  70                  75                  80

Cys Gly Gly Ser Asn Leu Ala Pro Leu Pro Arg Arg Glu Thr Glu Glu
                85                  90                  95

Phe Asn Asp Leu Leu Asp Leu Asp Phe Ile Leu Ser Asn Ser Leu Thr
            100                 105                 110

His Pro Pro Glu Ser Val Ala Ala Thr Val Ser Ser Ser Ala Ser Ala
        115                 120                 125

Ser Ser Ser Ser Ser Pro Ser Ser Gly Pro Ala Ser Ala Pro Ser
    130                 135                 140

```
Thr Cys Ser Phe Thr Tyr Pro Ile Arg Ala Gly Asn Asp Pro Gly Val
145                 150                 155                 160

Ala Pro Gly Gly Thr Gly Gly Leu Leu Tyr Gly Arg Glu Ser Ala
            165                 170                 175

Pro Pro Pro Thr Ala Pro Phe Asn Leu Ala Asp Ile Asn Asp Val Ser
            180                 185                 190

Pro Ser Gly Gly Phe Val Ala Glu Leu Leu Arg Pro Glu Leu Asp Pro
        195                 200                 205

Val Tyr Ile Pro Pro Gln Gln Pro Gln Pro Pro Gly Gly Gly Leu Met
210                 215                 220

Gly Lys Phe Val Leu Lys Ala Ser Leu Ser Ala Pro Gly Ser Glu Tyr
225                 230                 235                 240

Gly Ser Pro Ser Val Ile Ser Val Ser Lys Gly Ser Pro Asp Gly Ser
            245                 250                 255

His Pro Val Val Val Ala Pro Tyr Asn Gly Gly Pro Pro Arg Thr Cys
            260                 265                 270

Pro Lys Ile Lys Gln Glu Ala Val Ser Ser Cys Thr His Leu Gly Ala
        275                 280                 285

Gly Pro Pro Leu Ser Asn Gly His Arg Pro Ala Ala His Asp Phe Pro
290                 295                 300

Leu Gly Arg Gln Leu Pro Ser Arg Thr Thr Pro Thr Leu Gly Leu Glu
305                 310                 315                 320

Glu Val Leu Ser Ser Arg Asp Cys His Pro Ala Leu Pro Leu Pro Pro
            325                 330                 335

Gly Phe His Pro His Pro Gly Pro Asn Tyr Pro Ser Phe Leu Pro Asp
            340                 345                 350

Gln Met Gln Pro Gln Val Pro Pro Leu His Tyr Gln Glu Leu Met Pro
        355                 360                 365

Pro Gly Ser Cys Met Pro Glu Glu Pro Lys Pro Lys Arg Gly Arg Arg
370                 375                 380

Ser Trp Pro Arg Lys Arg Thr Ala Thr His Thr Cys Asp Tyr Ala Gly
385                 390                 395                 400

Cys Gly Lys Thr Tyr Thr Lys Ser Ser His Leu Lys Ala His Leu Arg
            405                 410                 415

Thr His Thr Gly Glu Lys Pro Tyr His Cys Asp Trp Asp Gly Cys Gly
            420                 425                 430

Trp Lys Phe Ala Arg Ser Asp Glu Leu Thr Arg His Tyr Arg Lys His
        435                 440                 445

Thr Gly His Arg Pro Phe Gln Cys Gln Lys Cys Asp Arg Ala Phe Ser
    450                 455                 460

Arg Ser Asp His Leu Ala Leu His Met Lys Arg His Phe
465                 470                 475

<210> SEQ ID NO 5
<211> LENGTH: 651
<212> TYPE: DNA
<213> ORGANISM: Homo sapiens

<400> SEQUENCE: 5
atgaacaatt cgcccttcac catgggctcc gtgtccaacc agcagtttgc aggtggctgc     60
gccaaggcgg cagaagaggc gcccgaggag gcgccggagg acgcggcccg ggcggcggac    120
gagcctcagc tgctgcacgg tgcgggcatc tgtaagtggt tcaacgtgcg catgggcttc    180
ggcttcctgt ccatgaccgc ccgcgccggg gtcgcgctcg acccccccagt ggatgtcttt    240
```

```
gtgcaccaga gtaagctgca catggaaggg ttccggagct tgaaggaggg tgaggcagtg      300
gagttcacct ttaagaagtc agccaagggt ctggaatcca tccgtgtcac cggacctggt      360
ggagtattct gtattgggag tgagaggcgg ccaaaaggaa agagcatgca aagcgcaga       420 tcaaaaggag acaggtgcta caactgtgga ggtctagatc atcatgccaa ggaatgcaag      480
ctgccacccc agcccaagaa gtgccacttc tgccagagca tcagccatat ggtagcctca      540
tgtccgctga aggcccagca gggccctagt gcacagggaa agccaaccta ctttcgagag      600
gaagaagaag aaatccacag ccctaccctg ctcccggagg cacagaattg a               651
```

<210> SEQ ID NO 6
<211> LENGTH: 216
<212> TYPE: PRT
<213> ORGANISM: Homo sapiens
<400> SEQUENCE: 6

```
Met Asn Asn Ser Pro Phe Thr Met Gly Ser Val Ser Asn Gln Gln Phe
1               5                   10                  15

Ala Gly Gly Cys Ala Lys Ala Ala Glu Glu Ala Pro Glu Glu Ala Pro
            20                  25                  30

Glu Asp Ala Ala Arg Ala Ala Asp Glu Pro Gln Leu Leu His Gly Ala
        35                  40                  45

Gly Ile Cys Lys Trp Phe Asn Val Arg Met Gly Phe Gly Phe Leu Ser
    50                  55                  60

Met Thr Ala Arg Ala Gly Val Ala Leu Asp Pro Pro Val Asp Val Phe
65                  70                  75                  80

Val His Gln Ser Lys Leu His Met Glu Gly Phe Arg Ser Leu Lys Glu
                85                  90                  95

Gly Glu Ala Val Glu Phe Thr Phe Lys Lys Ser Ala Lys Gly Leu Glu
            100                 105                 110

Ser Ile Arg Val Thr Gly Pro Gly Gly Val Phe Cys Ile Gly Ser Glu
        115                 120                 125

Arg Arg Pro Lys Gly Lys Ser Met Gln Lys Arg Arg Ser Lys Gly Asp
    130                 135                 140

Arg Cys Tyr Asn Cys Gly Gly Leu Asp His His Ala Lys Glu Cys Lys
145                 150                 155                 160

Leu Pro Pro Gln Pro Lys Lys Cys His Phe Cys Gln Ser Ile Ser His
                165                 170                 175

Met Val Ala Ser Cys Pro Leu Lys Ala Gln Gln Gly Pro Ser Ala Gln
            180                 185                 190

Gly Lys Pro Thr Tyr Phe Arg Glu Glu Glu Glu Ile His Ser Pro
        195                 200                 205

Thr Leu Leu Pro Glu Ala Gln Asn
    210                 215
```

<210> SEQ ID NO 7
<211> LENGTH: 1209
<212> TYPE: DNA
<213> ORGANISM: Homo sapiens
<400> SEQUENCE: 7

```
atgttcatgc cttcttcttt ttcctacagc tcctgggcaa cgtgctggtt attgtgctgt       60
ctcatcattt tggcaaagaa ttcgcccttc accatggact acgactcgta ccagcactat      120
ttctacgact atgactgcgg ggaggatttc taccgctcca cggcgcccag cgaggacatc      180
tggaagaaat tcgagctggt gccatcgccc ccacgtcgc cgccctgggg cttgggtccc       240
```

-continued

```
ggcgcagggg acccggcccc cgggattggt cccccggagc cgtggcccgg agggtgcacc      300
ggagacgaag cggaatcccg gggccactcg aaaggctggg gcaggaacta cgcctccatc      360
atacgccgtg actgcatgtg gagcggcttc tcggcccggg aacggctgga gagagctgtg      420
agcgaccggc tcgctcctgg cgcgccccgg gggaacccgc ccaaggcgtc cgccgccccg      480
gactgcactc ccagcctcga agccggcaac ccggcgcccg ccgcccctg tccgctgggc       540
gaacccaaga cccaggcctg ctccgggtcc gagagcccaa gcgactcgga gaatgaagaa      600
attgatgttg tgacagtaga aagaggcag tctctgggta ttcggaagcc ggtcaccatc       660
acggtgcgag cagacccct ggatccctgc atgaagcatt ccacatctc catccatcag        720
caacagcaca actatgctgc ccgttttcct ccagaaagct gctcccaaga gaggcttca      780
gagaggggtc cccaagaaga ggttctggag agagatgctg caggggaaaa ggaagatgag      840
gaggatgaag agattgtgag tcccccacct gtagaaagtg aggctgccca gtcctgccac      900
cccaaacctg tcagttctga tactgaggat gtgaccaaga ggaagaatca caacttcctg      960
gagcgcaaga ggcggaatga cctgcgttcg cgattcttgg cgctgaggga ccaggtgccc     1020
accctggcca gctgctccaa ggccccaaa gtagtgatcc taagcaaggc cttggaatac      1080
ttgcaagccc tggtgggggc tgagaagagg atggctacag agaaaagaca gctccgatgc     1140
cggcagcagc agttgcagaa aagaattgca tacctcactg gctacggaga tctcaaaatt     1200
gtcgctcct                                                             1209
```

<210> SEQ ID NO 8
<211> LENGTH: 403
<212> TYPE: PRT
<213> ORGANISM: Homo sapiens

<400> SEQUENCE: 8

```
Met Phe Met Pro Ser Ser Phe Ser Tyr Ser Ser Trp Ala Thr Cys Trp
1               5                   10                  15
Leu Leu Cys Cys Leu Ile Ile Leu Ala Lys Asn Ser Pro Phe Thr Met
                20                  25                  30
Asp Tyr Asp Ser Tyr Gln His Tyr Phe Tyr Asp Tyr Asp Cys Gly Glu
            35                  40                  45
Asp Phe Tyr Arg Ser Thr Ala Pro Ser Glu Asp Ile Trp Lys Lys Phe
        50                  55                  60
Glu Leu Val Pro Ser Pro Pro Thr Ser Pro Pro Trp Gly Leu Gly Pro
65                  70                  75                  80
Gly Ala Gly Asp Pro Ala Pro Gly Ile Gly Pro Pro Glu Pro Trp Pro
                85                  90                  95
Gly Gly Cys Thr Gly Asp Glu Ala Glu Ser Arg Gly His Ser Lys Gly
            100                 105                 110
Trp Gly Arg Asn Tyr Ala Ser Ile Ile Arg Arg Asp Cys Met Trp Ser
        115                 120                 125
Gly Phe Ser Ala Arg Glu Arg Leu Glu Arg Ala Val Ser Asp Arg Leu
    130                 135                 140
Ala Pro Gly Ala Pro Arg Gly Asn Pro Pro Lys Ala Ser Ala Ala Pro
145                 150                 155                 160
Asp Cys Thr Pro Ser Leu Glu Ala Gly Asn Pro Ala Pro Ala Ala Pro
                165                 170                 175
Cys Pro Leu Gly Glu Pro Lys Thr Gln Ala Cys Ser Gly Ser Glu Ser
            180                 185                 190
```

```
Pro Ser Asp Ser Glu Asn Glu Glu Ile Asp Val Val Thr Val Glu Lys
            195                 200                 205
Arg Gln Ser Leu Gly Ile Arg Lys Pro Val Thr Ile Thr Val Arg Ala
        210                 215                 220
Asp Pro Leu Asp Pro Cys Met Lys His Phe His Ile Ser Ile His Gln
225                 230                 235                 240
Gln Gln His Asn Tyr Ala Ala Arg Phe Pro Pro Glu Ser Cys Ser Gln
                245                 250                 255
Glu Glu Ala Ser Glu Arg Gly Pro Gln Glu Val Leu Glu Arg Asp
            260                 265                 270
Ala Ala Gly Glu Lys Glu Asp Glu Asp Glu Ile Val Ser Pro
        275                 280                 285
Pro Pro Val Glu Ser Glu Ala Ala Gln Ser Cys His Pro Lys Pro Val
    290                 295                 300
Ser Ser Asp Thr Glu Asp Val Thr Lys Arg Lys Asn His Asn Phe Leu
305                 310                 315                 320
Glu Arg Lys Arg Arg Asn Asp Leu Arg Ser Arg Phe Leu Ala Leu Arg
                325                 330                 335
Asp Gln Val Pro Thr Leu Ala Ser Cys Ser Lys Ala Pro Lys Val Val
            340                 345                 350
Ile Leu Ser Lys Ala Leu Glu Tyr Leu Gln Ala Leu Val Gly Ala Glu
        355                 360                 365
Lys Arg Met Ala Thr Glu Lys Arg Gln Leu Arg Cys Arg Gln Gln Gln
    370                 375                 380
Leu Gln Lys Arg Ile Ala Tyr Leu Thr Gly Tyr Gly Asp Leu Lys Ile
385                 390                 395                 400
Val Ala Pro

<210> SEQ ID NO 9
<211> LENGTH: 1176
<212> TYPE: DNA
<213> ORGANISM: Homo sapiens

<400> SEQUENCE: 9
atgttcatgc cttcttcttt tcctacagc tcctgggcaa cgtgctggtt attgtgctgt    60
ctcatcattt tggcaaagaa ttcgcccttc accatggcgg acacctggc ttcggatttc   120
gccttctcgc cccctccagg tggtggaggt gatgggccag ggggccgga gccgggctgg   180
gttgatcctc ggacctggct aagcttccaa ggccctcctg agggccagg aatcgggccg   240
ggggttgggc caggctctga ggtgtgggg attcccccat gccccccgcc gtatgagttc   300
tgtggggga tggcgtactg tgggccccag gttggagtgg ggctagtgcc ccaaggcggc   360
ttggagacct ctcagcctga gggcgaagca ggagtcgggg tggagagcaa ctccgatggg   420
gcctccccgg agccctgcac cgtcacccct ggtgccgtga agctggagaa ggagaagctg   480
gagcaaaacc cggaggagtc ccaggacatc aaagctctgc agaaagaact cgagcaattt   540
gccaagctcc tgaagcagaa aggatcaccc tgggatata cacaggccga tgtggggctc   600
accctggggg ttctatttgg gaaggtattc agccaaacga ccatctgccg ctttgaggct   660
ctgcagctta gcttcaagaa catgtgtaag ctgcggccct gctgcagaa gtgggtggag   720
gaagctgaca caatgaaaaa tcttcaggag atatgcaaag cagaaaccct cgtgcaggcc   780
cgaaagagaa agcgaaccag tatcgagaac gagtgagag caacctggaa gaatttgttc   840
ctgcagtgcc cgaaacccac actgcagcag atcagccaca tcgcccagca gcttgggctc   900
```

-continued

```
gagaaggatg tggtccgagt gtggttctgt aaccggcgcc agaagggcaa gcgatcaagc      960
agcgactatg cacaacgaga ggattttgag gctgctgggt ctcctttctc aggggggacca   1020 gtgtcctttc ctctggcccc agggccccat tttggtaccc caggctatgg gagccctcac   1080
ttcactgcac tgtactcctc ggtccctttc cctgaggggg aagcctttcc ccctgtctct   1140
gtcaccactc tgggctctcc catgcattca aactga                              1176
```

<210> SEQ ID NO 10
<211> LENGTH: 391
<212> TYPE: PRT
<213> ORGANISM: Homo sapiens

<400> SEQUENCE: 10

```
Met Phe Met Pro Ser Ser Phe Ser Tyr Ser Ser Trp Ala Thr Cys Trp
1               5                   10                  15

Leu Leu Cys Cys Leu Ile Ile Leu Ala Lys Asn Ser Pro Phe Thr Met
            20                  25                  30

Ala Gly His Leu Ala Ser Asp Phe Ala Phe Ser Pro Pro Pro Gly Gly
        35                  40                  45

Gly Gly Asp Gly Pro Gly Gly Pro Glu Pro Gly Trp Val Asp Pro Arg
    50                  55                  60

Thr Trp Leu Ser Phe Gln Gly Pro Pro Gly Gly Pro Gly Ile Gly Pro
65                  70                  75                  80

Gly Val Gly Pro Gly Ser Glu Val Trp Gly Ile Pro Pro Cys Pro Pro
                85                  90                  95

Pro Tyr Glu Phe Cys Gly Gly Met Ala Tyr Cys Gly Pro Gln Val Gly
            100                 105                 110

Val Gly Leu Val Pro Gln Gly Gly Leu Glu Thr Ser Gln Pro Glu Gly
        115                 120                 125

Glu Ala Gly Val Gly Val Glu Ser Asn Ser Asp Gly Ala Ser Pro Glu
    130                 135                 140

Pro Cys Thr Val Thr Pro Gly Ala Val Lys Leu Glu Lys Glu Lys Leu
145                 150                 155                 160

Glu Gln Asn Pro Glu Glu Ser Gln Asp Ile Lys Ala Leu Gln Lys Glu
                165                 170                 175

Leu Glu Gln Phe Ala Lys Leu Leu Lys Gln Lys Arg Ile Thr Leu Gly
            180                 185                 190

Tyr Thr Gln Ala Asp Val Gly Leu Thr Leu Gly Val Leu Phe Gly Lys
        195                 200                 205

Val Phe Ser Gln Thr Thr Ile Cys Arg Phe Glu Ala Leu Gln Leu Ser
    210                 215                 220

Phe Lys Asn Met Cys Lys Leu Arg Pro Leu Leu Gln Lys Trp Val Glu
225                 230                 235                 240

Glu Ala Asp Asn Asn Glu Asn Leu Gln Glu Ile Cys Lys Ala Glu Thr
                245                 250                 255

Leu Val Gln Ala Arg Lys Arg Lys Arg Thr Ser Ile Glu Asn Arg Val
            260                 265                 270

Arg Gly Asn Leu Glu Asn Leu Phe Leu Gln Cys Pro Lys Pro Thr Leu
        275                 280                 285

Gln Gln Ile Ser His Ile Ala Gln Gln Leu Gly Leu Glu Lys Asp Val
    290                 295                 300

Val Arg Val Trp Phe Cys Asn Arg Arg Gln Lys Gly Lys Arg Ser Ser
305                 310                 315                 320

Ser Asp Tyr Ala Gln Arg Glu Asp Phe Glu Ala Ala Gly Ser Pro Phe
```

|  | 325 |  |  |  | 330 |  |  |  |  | 335 |  |
| --- | --- | --- | --- | --- | --- | --- | --- | --- | --- | --- | --- |

Ser Gly Gly Pro Val Ser Phe Pro Leu Ala Pro Gly Pro His Phe Gly
                340                         345                      350

Thr Pro Gly Tyr Gly Ser Pro His Phe Thr Ala Leu Tyr Ser Ser Val
            355                         360                     365

Pro Phe Pro Glu Gly Glu Ala Phe Pro Pro Val Ser Val Thr Thr Leu
    370                         375                     380

Gly Ser Pro Met His Ser Asn
385                 390

<210> SEQ ID NO 11
<211> LENGTH: 1790
<212> TYPE: DNA
<213> ORGANISM: Epstein-Barr virus

<400> SEQUENCE: 11

| caggaaaagg | acaagcagcg | aaaattcacg | cccccttggg | aggtggcggc | atatgcaaag | 60 |
| gatagcactc | ccactctact | actgggtatc | atatgctgac | tgtatatgca | tgaggatagc | 120 |
| atatgctacc | cggatacaga | ttaggatagc | atatactacc | cagatataga | ttaggatagc | 180 |
| atatgctacc | cagatataga | ttaggatagc | ctatgctacc | cagatataaa | ttaggatagc | 240 |
| atatactacc | cagatataga | ttaggatagc | atatgctacc | cagatataga | ttaggatagc | 300 |
| ctatgctacc | cagatataga | ttaggatagc | atatgctacc | cagatataga | ttaggatagc | 360 |
| atatgctatc | cagatatttg | ggtagtatat | gctacccaga | tataaattag | gatagcatat | 420 |
| actaccctaa | tctctattag | gatagcatat | gctacccgga | tacagattag | gatagcatat | 480 |
| actacccaga | tatagattag | gatagcatat | gctacccaga | tatagattag | gatagcctat | 540 |
| gctacccaga | tataaattag | gatagcatat | actacccaga | tatagattag | gatagcatat | 600 |
| gctacccaga | tatagattag | gatagcctat | gctacccaga | tatagattag | gatagcatat | 660 |
| gctatccaga | tatttgggta | gtatatgcta | cccatggcaa | cattagccca | ccgtgctctc | 720 |
| agcgacctcg | tgaatatgag | gaccaacaac | cctgtgcttg | gcgctcaggc | gcaagtgtgt | 780 |
| gtaatttgtc | ctccagatcg | cagcaatcgc | gcccctatct | tggcccgccc | acctacttat | 840 |
| gcaggtattc | cccggggtgc | cattagtggt | tttgtgggca | agtggtttga | ccgcagtggt | 900 |
| tagcggggtt | acaatcagcc | aagttattac | acccttattt | tacagtccaa | aaccgcaggg | 960 |
| cggcgtgtgg | gggctgacgc | gtgcccccac | tccacaattt | caaaaaaaag | agtggccact | 1020 |
| tgtctttgtt | tatgggcccc | attggcgtgg | agccccgttt | aattttcggg | ggtgttagag | 1080 |
| acaaccagtg | gagtccgctg | ctgtcggcgt | ccactctctt | tccccttgtt | acaaatagag | 1140 |
| tgtaacaaca | tggttcacct | gtcttggtcc | ctgcctggga | cacatcttaa | taaccccagt | 1200 |
| atcatattgc | actaggatta | tgtgttgccc | atagccataa | attcgtgtga | gatggacatc | 1260 |
| cagtctttac | ggcttgtccc | cacccccatgg | atttctattg | ttaaagatat | tcagaatgtt | 1320 |
| tcattcctac | actagtattt | attgcccaag | gggtttgtga | gggttatatt | ggtgtcatag | 1380 |
| cacaatgcca | ccactgaacc | ccccgtccaa | attttattct | ggggcgtca | cctgaaacct | 1440 |
| tgttttcgag | cacctcacat | acaccttact | gttcacaact | cagcagttat | tctattagct | 1500 |
| aaacgaagga | gaatgaagaa | gcaggcgaag | attcaggaga | gttcactgcc | cgctccttga | 1560 |
| tcttcagcca | ctgcccttgt | gactaaaatg | gttcactacc | ctcgtggaat | cctgaccccca | 1620 |
| tgtaaataaa | accgtgacag | ctcatggggt | gggagatatc | gctgttcctt | aggacccttt | 1680 |
| tactaaccct | aattcgatag | catatgcttc | ccgttgggta | acatatgcta | ttgaattagg | 1740 |

```
gttagtctgg atagtatata ctactacccg ggaagcatat gctacccgtt          1790
```

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

```
gactccagtg gtaatctac                                            19
```

<210> SEQ ID NO 13
<211> LENGTH: 1173
<212> TYPE: DNA
<213> ORGANISM: Mus musculus

<400> SEQUENCE: 13

```
atgactgcca tggaggagtc acagtcggat atcagcctcg agctccctct gagccaggag    60
acattttcag gcttatggaa actacttcct ccagaagata tcctgccatc acctcactgc   120
atggacgatc tgttgctgcc ccaggatgtt gaggagtttt ttgaaggccc aagtgaagcc   180
ctccgagtgt caggagctcc tgcagcacag gaccctgtca ccgagacccc tgggccagtg   240
gcccctgccc cagccactcc atggcccctg tcatcttttg tcccttctca aaaaacttac   300
cagggcaact atggcttcca cctgggcttc ctgcagtctg gacagccaa gtctgttatg   360
tgcacgtact ctcctcccct caataagcta ttctgccagc tggcgaagac gtgccctgtg   420
cagttgtggg tcagcgccac acctccagct gggagccgtg tccgcgccat ggccatctac   480
aagaagtcac agcacatgac ggaggtcgtg agacgctgcc cccaccatga gcgctgctcc   540
gatggtgatg gcctggctcc tccccagcat cttatccggg tggaaggaaa tttgtatccc   600
gagtatctgg aagacaggca gacttttcgc cacagcgtgg tggtacccta tgagccaccc   660
gaggccggct ctgagtatac caccatccac tacaagtaca tgtgtaatag ctcctgcatg   720
gggggcatga accgccgacc tatccttacc atcatcacac tggaagactc cagtgggaac   780
cttctgggac gggacagctt tgaggttcgt gtttgtgcct gccctgggag agaccgccgt   840
acagaagaag aaaatttccg caaaaaggaa gtcctttgcc ctgaactgcc ccagggagc   900
gcaaagagag cgctgcccac ctgcacaagc gcctctcccc gcaaaagaa aaaccactt   960
gatggagagt atttcaccct caagatccgc gggcgtaaac gcttcgagat gttccgggag  1020
ctgaatgagg ccttagagtt aaaggatgcc catgctacag aggagtctgg agacagcagg  1080
gctcactcca gctacctgaa gaccaagaag ggccagtcta cttcccgcca taaaaaaaca  1140
atggtcaaga agtggggcc tgactcagac tga                                 1173
```

<210> SEQ ID NO 14
<211> LENGTH: 390
<212> TYPE: PRT
<213> ORGANISM: Mus musculus

<400> SEQUENCE: 14

```
Met Thr Ala Met Glu Glu Ser Gln Ser Asp Ile Ser Leu Glu Leu Pro
1               5                   10                  15

Leu Ser Gln Glu Thr Phe Ser Gly Leu Trp Lys Leu Leu Pro Pro Glu
            20                  25                  30

Asp Ile Leu Pro Ser Pro His Cys Met Asp Asp Leu Leu Leu Pro Gln
```

```
                    35                  40                  45
Asp Val Glu Glu Phe Phe Glu Gly Pro Ser Glu Ala Leu Arg Val Ser
 50                  55                  60

Gly Ala Pro Ala Ala Gln Asp Pro Val Thr Glu Thr Pro Gly Pro Val
 65                  70                  75                  80

Ala Pro Ala Pro Ala Thr Pro Trp Pro Leu Ser Ser Phe Val Pro Ser
                 85                  90                  95

Gln Lys Thr Tyr Gln Gly Asn Tyr Gly Phe His Leu Gly Phe Leu Gln
             100                 105                 110

Ser Gly Thr Ala Lys Ser Val Met Cys Thr Tyr Ser Pro Pro Leu Asn
         115                 120                 125

Lys Leu Phe Cys Gln Leu Ala Lys Thr Cys Pro Val Gln Leu Trp Val
     130                 135                 140

Ser Ala Thr Pro Pro Ala Gly Ser Arg Val Arg Ala Met Ala Ile Tyr
145                 150                 155                 160

Lys Lys Ser Gln His Met Thr Glu Val Val Arg Arg Cys Pro His His
                165                 170                 175

Glu Arg Cys Ser Asp Gly Asp Gly Leu Ala Pro Pro Gln His Leu Ile
            180                 185                 190

Arg Val Glu Gly Asn Leu Tyr Pro Glu Tyr Leu Glu Asp Arg Gln Thr
        195                 200                 205

Phe Arg His Ser Val Val Val Pro Tyr Glu Pro Pro Glu Ala Gly Ser
    210                 215                 220

Glu Tyr Thr Thr Ile His Tyr Lys Tyr Met Cys Asn Ser Ser Cys Met
225                 230                 235                 240

Gly Gly Met Asn Arg Arg Pro Ile Leu Thr Ile Ile Thr Leu Glu Asp
                245                 250                 255

Ser Ser Gly Asn Leu Leu Gly Arg Asp Ser Phe Glu Val Arg Val Cys
            260                 265                 270

Ala Cys Pro Gly Arg Asp Arg Arg Thr Glu Glu Glu Asn Phe Arg Lys
        275                 280                 285

Lys Glu Val Leu Cys Pro Glu Leu Pro Pro Gly Ser Ala Lys Arg Ala
    290                 295                 300

Leu Pro Thr Cys Thr Ser Ala Ser Pro Pro Gln Lys Lys Lys Pro Leu
305                 310                 315                 320

Asp Gly Glu Tyr Phe Thr Leu Lys Ile Arg Gly Arg Lys Arg Phe Glu
                325                 330                 335

Met Phe Arg Glu Leu Asn Glu Ala Leu Glu Leu Lys Asp Ala His Ala
            340                 345                 350

Thr Glu Glu Ser Gly Asp Ser Arg Ala His Ser Ser Tyr Leu Lys Thr
        355                 360                 365

Lys Lys Gly Gln Ser Thr Ser Arg His Lys Lys Thr Met Val Lys Lys
    370                 375                 380

Val Gly Pro Asp Ser Asp
385                 390

<210> SEQ ID NO 15
<211> LENGTH: 693
<212> TYPE: DNA
<213> ORGANISM: Discosoma sp.

<400> SEQUENCE: 15
agcgagctga tcaaggagaa catgcacatg aagctgtaca tggagggcac cgtgaacaac      60
caccacttca gtgcacatc cgagggcgaa ggcaagccct acgagggcac ccagaccatg     120
```

-continued

```
aagatcaagg tggtcgaggg cggccctctc cccttcgcct tcgacatcct ggctaccagc    180
ttcatgtacg gcagcaaagc cttcatcaac cacacccagg gcatccccga cttctttaag    240
cagtccttcc ctgagggctt cacatgggag agaatcacca catacgaaga cggggcgtg     300 ctgaccgcta cccaggacac cagcttccag aacggctgca tcatctacaa cgtcaagatc    360
aacggggtga acttcccatc caacggccct gtgatgcaga agaaaacacg cggctgggag    420
gccaacaccg agatgctgta ccccgctgac ggcggcctga gaggcacag ccagatggcc     480 ctgaagctcg tgggcggggg ctacctgcac tgctccttca agaccacata cagatccaag    540
aaacccgcta agaacctcaa gatgcccggc ttccacttcg tggaccacag actggaaaga    600
atcaaggagg ccgacaaaga gacctacgtc gagcagcacg agatggctgt ggccaagtac    660
tgcgacctcc ctagcaaact ggggcacaga taa                                 693
```

<210> SEQ ID NO 16
<211> LENGTH: 221
<212> TYPE: PRT
<213> ORGANISM: Discosoma sp.

<400> SEQUENCE: 16

```
Met Lys Leu Tyr Met Glu Gly Thr Val Asn Asn His His Phe Lys Cys
 1               5                  10                  15

Thr Ser Glu Gly Glu Gly Lys Pro Tyr Glu Gly Thr Gln Thr Met Lys
             20                  25                  30

Ile Lys Val Val Glu Gly Gly Pro Leu Pro Phe Ala Phe Asp Ile Leu
         35                  40                  45

Ala Thr Ser Phe Met Tyr Gly Ser Lys Ala Phe Ile Asn His Thr Gln
     50                  55                  60

Gly Ile Pro Asp Phe Phe Lys Gln Ser Phe Pro Glu Gly Phe Thr Trp
 65                  70                  75                  80

Glu Arg Ile Thr Thr Tyr Glu Asp Gly Gly Val Leu Thr Ala Thr Gln
                 85                  90                  95

Asp Thr Ser Phe Gln Asn Gly Cys Ile Ile Tyr Asn Val Lys Ile Asn
            100                 105                 110

Gly Val Asn Phe Pro Ser Asn Gly Pro Val Met Gln Lys Lys Thr Arg
        115                 120                 125

Gly Trp Glu Ala Asn Thr Glu Met Leu Tyr Pro Ala Asp Gly Gly Leu
    130                 135                 140

Arg Gly His Ser Gln Met Ala Leu Lys Leu Val Gly Gly Gly Tyr Leu
145                 150                 155                 160

His Cys Ser Phe Lys Thr Thr Tyr Arg Ser Lys Lys Pro Ala Lys Asn
                165                 170                 175

Leu Lys Met Pro Gly Phe His Phe Val Asp His Arg Leu Glu Arg Ile
            180                 185                 190

Lys Glu Ala Asp Lys Glu Thr Tyr Val Glu Gln His Glu Met Ala Val
        195                 200                 205

Ala Lys Tyr Cys Asp Leu Pro Ser Lys Leu Gly His Arg
    210                 215                 220
```

<210> SEQ ID NO 17
<211> LENGTH: 1068
<212> TYPE: DNA
<213> ORGANISM: Homo sapiens

<400> SEQUENCE: 17

```
atgttcatgc cttcttcttt ttcctacagc tcctgggcaa cgtgctggtt attgtgctgt     60
ctcatcattt tggcaaagaa ttcgcccttc accatgtaca acatgatgga gacggagctg    120
aagccgccgg gcccgcagca aacttcgggg gcggcggcg gcaactccac cgcggcggcg    180
gccggcggca accagaaaaa cagcccggac cgcgtcaagc ggcccatgaa tgccttcatg    240
gtgtggtccc gcgggcagcg cgcaagatg gcccaggaga accccaagat gcacaactcg    300
gagatcagca agcgcctggg cgccgagtgg aaacttttgt cggagacgga aagcggccg    360
ttcatcgacg aggctaagcg gctgcgagcg ctgcacatga aggagcaccc ggattataaa    420
taccggcccc ggcggaaaac caagacgctc atgaagaagg ataagtacac gctgcccggc    480
gggctgctgg cccccggcgg caatagcatg gcgagcgggg tcggggtggg cgccggcctg    540
ggcgcgggcg tgaaccagcg catggacagt acgcgcaca tgaacggctg agcaacggc    600
agctacagca tgatgcagga ccagctgggc tacccgcagc acccgggcct caatgcgcac    660
ggcgcagcgc agatgcagcc catgcaccgc tacgacgtga cgccctgca gtacaactcc    720
atgaccagct cgcagaccta catgaacggc tcgcccacct acagcatgtc ctactcgcag    780
cagggcaccc ctggcatggc tcttggctcc atgggttcgg tggtcaagtc cgaggccagc    840
tccagccccc ctgtggttac ctcttcctcc cactccaggg cgccctgcca ggccggggac    900
ctccgggaca tgatcagcat gtatctcccc ggcgccgagg tgccggaacc cgccgccccc    960
agcagacttc acatgtccca gcactaccag agcggcccgg tgcccggcac ggccattaac   1020
ggcacactgc ccctctcaca catgggggat ctcaaaattg tcgctcct                1068
```

<210> SEQ ID NO 18
<211> LENGTH: 356
<212> TYPE: PRT
<213> ORGANISM: Homo sapiens

<400> SEQUENCE: 18

```
Met Phe Met Pro Ser Ser Phe Ser Tyr Ser Ser Trp Ala Thr Cys Trp
 1               5                  10                  15

Leu Leu Cys Cys Leu Ile Ile Leu Ala Lys Asn Ser Pro Phe Thr Met
            20                  25                  30

Tyr Asn Met Met Glu Thr Glu Leu Lys Pro Pro Gly Pro Gln Gln Thr
        35                  40                  45

Ser Gly Gly Gly Gly Asn Ser Thr Ala Ala Ala Gly Gly Asn
    50                  55                  60

Gln Lys Asn Ser Pro Asp Arg Val Lys Arg Pro Met Asn Ala Phe Met
65                  70                  75                  80

Val Trp Ser Arg Gly Gln Arg Arg Lys Met Ala Gln Glu Asn Pro Lys
                85                  90                  95

Met His Asn Ser Glu Ile Ser Lys Arg Leu Gly Ala Glu Trp Lys Leu
            100                 105                 110

Leu Ser Glu Thr Glu Lys Arg Pro Phe Ile Asp Glu Ala Lys Arg Leu
        115                 120                 125

Arg Ala Leu His Met Lys Glu His Pro Asp Tyr Lys Tyr Arg Pro Arg
    130                 135                 140

Arg Lys Thr Lys Thr Leu Met Lys Lys Asp Lys Tyr Thr Leu Pro Gly
145                 150                 155                 160

Gly Leu Leu Ala Pro Gly Gly Asn Ser Met Ala Ser Gly Val Gly Val
                165                 170                 175

Gly Ala Gly Leu Gly Ala Gly Val Asn Gln Arg Met Asp Ser Tyr Ala
            180                 185                 190
```

```
His Met Asn Gly Trp Ser Asn Gly Ser Tyr Ser Met Met Gln Asp Gln
            195                 200                 205

Leu Gly Tyr Pro Gln His Pro Gly Leu Asn Ala His Gly Ala Ala Gln
        210                 215                 220

Met Gln Pro Met His Arg Tyr Asp Val Ser Ala Leu Gln Tyr Asn Ser
225                 230                 235                 240

Met Thr Ser Ser Gln Thr Tyr Met Asn Gly Ser Pro Thr Tyr Ser Met
                245                 250                 255

Ser Tyr Ser Gln Gln Gly Thr Pro Gly Met Ala Leu Gly Ser Met Gly
            260                 265                 270

Ser Val Val Lys Ser Glu Ala Ser Ser Pro Val Val Thr Ser
            275                 280                 285

Ser Ser His Ser Arg Ala Pro Cys Gln Ala Gly Asp Leu Arg Asp Met
        290                 295                 300

Ile Ser Met Tyr Leu Pro Gly Ala Glu Val Pro Glu Pro Ala Ala Pro
305                 310                 315                 320

Ser Arg Leu His Met Ser Gln His Tyr Gln Ser Gly Pro Val Pro Gly
                325                 330                 335

Thr Ala Ile Asn Gly Thr Leu Pro Leu Ser His Met Gly Asp Leu Lys
            340                 345                 350

Ile Val Ala Pro
        355

<210> SEQ ID NO 19
<211> LENGTH: 317
<212> TYPE: DNA
<213> ORGANISM: Simian virus 40

<400> SEQUENCE: 19
ggtgtggaaa gtccccaggc tccccagcag gcagaagtat gcaaagcatg catctcaatt      60
agtcagcaac caggtgtgga aagtcccag gctccccagc aggcagaagt atgcaaagca     120
tgcatctcaa ttagtcagca accatagtcc cgcccctaac tccgcccatc cgcccctaa     180 ctccgcccag ttccgcccat tctccgcccc atggctgact aatttttttt atttatgcag    240
aggccgaggc cgcctcggcc tctgagctat tccagaagta gtgaggaggc ttttttggag    300
gcctaggctt tgcaaa                                                    317

<210> SEQ ID NO 20
<211> LENGTH: 10186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca gtccgccccc tattgacgtc aatgacggt aaatggcccg    300 cctggcatta tgcccagtac atgaccttac gggactttcc tacttggcag tacatctacg    360
tattagtcat cgctattacc atggtgatgc ggttttggca gtacaccaat gggcgtggat    420
```

-continued

```
agcggtttga ctcacgggga tttccaagtc tccaccccat tgacgtcaat gggagtttgt      480
tttggcacca aaatcaacgg gactttccaa aatgtcgtaa taaccccgcc ccgttgacgc      540
aaatgggcgg taggcgtgta cggtgggagg tctatataag cagagctcgt ttagtgaacc      600
gtcagatctc tagaagctgg gtaccagctg ctagcaagct tgctagcggc cgctcgaggc      660
cggcaaggcc ggatccagac atgataagat acattgatga gtttggacaa accacaacta      720
gaatgcagtg aaaaaaatgc tttatttgtg aaatttgtga tgctattgct ttatttgtaa      780
ccattataag ctgcaataaa caagttaaca acaacaattg cattcatttt atgtttcagg      840
ttcaggggga ggtgtgggag gttttttaaa gcaagtaaaa cctctacaaa tgtggtatgg      900
ctgattatga tccggctgcc tcgcgcgttt cggtgatgac ggtgaaaacc tctgacacat      960
gcagctcccg gagacggtca cagcttgtct gtaagcggat gccggagcag acaagcccg     1020 tcaggcgtca gcgggtgttg gcgggtgtcg ggcgcagcc atgaggtcga ctctagagga     1080 tcgatgccccc gccccggacg aactaaacct gactacgaca tctctgcccc ttcttcgcgg     1140
ggcagtgcat gtaatccctt cagttggttg gtacaacttg ccaactgggc cctgttccac     1200
atgtgacacg ggggggggacc aaacacaaag gggttctctg actgtagttg acatccttat     1260
aaatggatgt gcacatttgc caacactgag tggctttcat cctggagcag actttgcagt     1320
ctgtggactg caacacaaca ttgcctttat gtgtaactct tggctgaagc tcttacacca     1380
atgctggggg acatgtacct cccaggggcc caggaagact acgggaggct acaccaacgt     1440
caatcagagg ggcctgtgta gctaccgata agcggaccct caagagggca ttagcaatag     1500
tgtttataag gccccccttgt taaccctaaa cgggtagcat atgcttcccg ggtagtagta     1560
tatactatcc agactaaccc taattcaata gcatatgtta cccaacggga agcatatgct     1620
atcgaattag ggttagtaaa agggtcctaa ggaacagcga tatctcccac cccatgagct     1680
gtcacggttt tatttacatg gggtcaggat tccacgaggg tagtgaacca ttttagtcac     1740
aagggcagtg gctgaagatc aaggagcggg cagtgaactc tcctgaatct tcgcctgctt     1800
cttcattctc cttcgtttag ctaatagaat aactgctgag ttgtgaacag taaggtgtat     1860
gtgaggtgct cgaaaacaag gtttcaggtg acgcccccag aataaatttt ggacgggggg     1920
ttcagtggtg gcattgtgct atgacaccaa tataaccctc acaaacccct tgggcaataa     1980
atactagtgt aggaatgaaa cattctgaat atctttaaca atagaaatcc atggggtggg     2040
gacaagccgt aaagactgga tgtccatctc acacgaattt atggctatgg gcaacacata     2100
atcctagtgc aatatgatac tggggttatt aagatgtgtc ccaggcaggg accaagacag     2160
gtgaaccatg ttgttacact ctatttgtaa caaggggaaa gagagtggac gccgacagca     2220
gcggactcca ctggttgtct ctaacacccc cgaaaattaa acggggctcc acgccaatgg     2280
ggcccataaa caaagacaag tggccactct ttttttttgaa attgtggagt ggggggcacgc     2340 gtcagccccc acacgccgcc ctgcggtttt ggactgtaaa ataagggtgt aataacttgg     2400
ctgattgtaa ccccgctaac cactgcggtc aaaccacttg cccacaaaac cactaatggc     2460
accccgggga ataccctgcat aagtaggtgg gcgggccaag ataggggcgc gattgctgcg     2520
atctggagga caaattacac acacttgcgc ctgagcgcca agcacagggt tgttggtcct     2580
catattcacg aggtcgctga gagcacggtg ggctaatgtt gccatgggta gcatatacta     2640
cccaaatatc tggatagcat atgctatcct aatctatatc tgggtagcat aggctatcct     2700
aatctatatc tgggtagcat atgctatcct aatctatatc tgggtagtat atgctatcct     2760
aatttatatc tgggtagcat aggctatcct aatctatatc tgggtagcat atgctatcct     2820
```

```
aatctatatc tgggtagtat atgctatcct aatctgtatc cgggtagcat atgctatcct    2880
aatagagatt agggtagtat atgctatcct aatttatatc tgggtagcat atactaccca    2940
aatatctgga tagcatatgc tatcctaatc tatatctggg tagcatatgc tatcctaatc    3000
tatatctggg tagcataggc tatcctaatc tatatctggg tagcatatgc tatcctaatc    3060
tatatctggg tagtatatgc tatcctaatt tatatctggg tagcataggc tatcctaatc    3120
tatatctggg tagcatatgc tatcctaatc tatatctggg tagtatatgc tatcctaatc    3180
tgtatccggg tagcatatgc tatcctcatg catatacagt cagcatatga tacccagtag    3240
tagagtggga gtgctatcct ttgcatatgc cgccacctcc caaggggcg tgaattttcg     3300 ctgcttgtcc ttttcctgct ggttgctccc attcttaggt gaatttaagg aggccaggct    3360
aaagccgtcg catgtctgat tgctcaccag gtaaatgtcg ctaatgtttt ccaacgcgag    3420
aaggtgttga gcgcggagct gagtgacgtg acaacatggg tatgcccaat tgccccatgt    3480
tgggaggacg aaaatggtga caagacagat ggccagaaat acaccaacag cacgcatgat    3540
gtctactggg gatttattct ttagtgcggg ggaatacacg gcttttaata cgattgaggg    3600
cgtctcctaa caagttacat cactcctgcc cttcctcacc ctcatctcca tcacctcctt    3660
catctccgtc atctccgtca tcaccctccg cggcagcccc ttccaccata ggtggaaacc    3720
agggaggcaa atctactcca tcgtcaaagc tgcacacagt caccctgata ttgcaggtag    3780
gagcgggctt tgtcataaca aggtccttaa tcgcatcctt caaaacctca gcaaatatat    3840
gagtttgtaa aaagaccatg aaataacaga caatggactc ccttagcggg ccaggttgtg    3900
ggccgggtcc aggggccatt ccaaagggga gacgactcaa tggtgtaaga cgacattgtg    3960
gaatagcaag ggcagttcct cgccttaggt tgtaaaggga ggtcttacta cctccatata    4020
cgaacacacc ggcgacccaa gttccttcgt cggtagtcct ttctacgtga ctcctagcca    4080
ggagagctct taaaccttct gcaatgttct caaatttcgg gttggaacct ccttgaccac    4140
gatgctttcc aaaccaccct cctttttgc gcctgcctcc atcaccctga ccccggggtc     4200
cagtgcttgg gccttctcct gggtcatctg cggggccctg ctctatcgct cccgggggca    4260
cgtcaggctc accatctggg ccaccttctt ggtggtattc aaaataatcg gcttcccta     4320 cagggtggaa aaatggcctt ctacctggag ggggcctgcg cggtggagac ccggatgatg    4380
atgactgact actgggactc ctgggcctct tttctccacg tccacgacct ctcccctgg    4440 ctctttcacg acttcccccc ctggctcttt cacgtcctct accccggcgg cctccactac    4500
ctcctcgacc ccgcctcca ctacctcctc gaccccggcc tccactgcct cctcgacccc    4560
ggcctccacc tcctgctcct gcccctcctg ctcctgcccc tcctcctgct cctgcccctc    4620
ctgcccctcc tgctcctgcc cctcctgccc ctcctgctcc tgcccctcct gcccctcctg    4680
ctcctgcccc tcctgcccct cctcctgctc ctgcccctcc tgcccctcct gctcctg      4740 ccctcctgc cctcctgct cctgcccctc tgcccctcc tgctcctgcc cctcctgccc     4800
ctcctgctcc tgcccctcct gctcctgccc ctcctgctcc tgcccctcct gctcctgccc    4860
ctcctgcccc tcctgcccct cctcctgctc tgcccctcc tgctcctgcc cctcctgccc    4920
ctcctgcccc tcctgctcct gcccctcctc ctgctcctgc cctcctgcc cctcctgccc    4980 ctcctcctgc tcctgcccct ctgcccctc ctgctcctg tgcccctcct gctcctg       5040 ccctcctgc cctcctgcc cctcctcctg ctcctgcccc tcctgcccct cctcctgctc     5100
ctgcccctcc tcctgctcct gcccctcctg cccctcctgc cctcctcct gctcctgccc    5160
```

```
ctcctcctgc tcctgcccct cctgcccctc ctgcccctcc tgcccctcct cctgctcctg    5220
cccctcctcc tgctcctgcc cctcctgctc ctgcccctcc cgctcctgct cctgctcctg    5280
ttccaccgtg ggtccctttg cagccaatgc aacttggacg ttttttggggt ctccggacac   5340
catctctatg tcttggccct gatcctgagc cgcccgggggc tctggtctt ccgcctcctc    5400
gtcctcgtcc tcttccccgt cctcgtccat ggttatcacc ccctcttctt tgaggtccac    5460
tgccgccgga gccttctggt ccagatgtgt ctcccttctc tcctaggcca tttccaggtc    5520
ctgtacctgg cccctcgtca gacatgattc acactaaaag agatcaatag acatctttat    5580
tagacgacgc tcagtgaata cagggagtgc agactcctgc cccctccaac agccccccca    5640
ccctcatccc cttcatggtc gctgtcagac agatccaggt ctgaaaattc cccatcctcc    5700
gaaccatcct cgtcctcatc accaattact cgcagcccgg aaaactcccg ctgaacatcc    5760
tcaagatttg cgtcctgagc ctcaagccag gcctcaaatt cctcgtcccc cttttttgctg   5820
gacggtaggg atggggattc tcggaccccc tcctcttcct cttcaaggtc accagacaga    5880
gatgctactg gggcaacgga agaaaagctg ggtgcggcct gtgaggatca gcttatcgat    5940
gataagctgt caaacatgag aattcttgaa gacgaaaggg cctcgtgata cgcctatttt    6000
tataggttaa tgtcatgata ataatggttt cttagacgtc aggtggcact tttcggggaa    6060
atgtgcgcgg aaccccctatt tgtttatttt tctaaataca ttcaaatatg tatccgctca   6120
tgagacaata accctgataa atgcttcaat aatattgaaa aaggaagagt atgagtattc    6180
aacatttccg tgtcgccctt attccttttt ttgcggcatt ttgccttcct gttttttgctc   6240
acccagaaac gctggtgaaa gtaaaagatg ctgaagatca gttgggtgca cgagtgggtt    6300
acatcgaact ggatctcaac agcggtaaga tccttgagag ttttcgcccc gaagaacgtt    6360
ttccaatgat gagcactttt aaagttctgc tatgtggcgc ggtattatcc cgtgttgacg    6420
ccgggcaaga gcaactcggt cgccgcatac actattctca gaatgacttg gttgagtact    6480
caccagtcac agaaaagcat cttacggatg gcatgacagt aagagaatta tgcagtgctg    6540
ccataaccat gagtgataac actgcggcca acttacttct gacaacgatc ggaggaccga    6600
aggagctaac cgcttttttg cacaacatgg ggatcatgt aactcgcctt gatcgttggg     6660
aaccggagct gaatgaagcc ataccaaacg acgagcgtga ccacacgatg cctgcagcaa    6720
tggcaacaac gttgcgcaaa ctattaactg gcgaactact tactctagct tcccggcaac    6780
aattaataga ctggatggag gcggataaag ttgcaggacc acttctgcgc tcggcccttc    6840
cggctggctg gtttattgct gataaatctg gagccggtga gcgtgggtct cgcggtatca    6900
ttgcagcact ggggccagat ggtaagccct cccgtatcgt agttatctac acgacgggga    6960
gtcaggcaac tatggatgaa cgaaatagac agatcgctga tagtgcc tcactgatta      7020
agcattggta actgtcagac caagtttact catatatact ttagattgat ttaaaacttc    7080
atttttaatt taaaaggatc taggtgaaga tccttttttga taatctcatg accaaaatcc    7140
cttaacgtga gttttcgttc cactgagcgt cagacccgt agaaaagatc aaaggatctt     7200
cttgagatcc ttttttttctg cgcgtaatct gctgcttgca acaaaaaaa ccaccgctac    7260
cagcggtggt ttgtttgccg gatcaagagc taccaactct ttttccgaag gtaactggct    7320
tcagcagagc gcagatacca atactgtcc ttctagtgta gccgtagtta ggccaccact     7380
tcaagaactc tgtagcaccg cctacatacc tcgctctgct aatcctgtta ccagtggctg    7440
ctgccagtgg cgataagtcg tgtcttaccg ggttggactc aagacgatag ttaccggata    7500
aggcgcagcg gtcgggctga acgggggggtt cgtgcacaca gcccagcttg gagcgaacga   7560
```

```
cctacaccga actgagatac ctacagcgtg agctatgaga aagcgccacg cttcccgaag    7620
ggagaaaggc ggacaggtat ccggtaagcg gcagggtcgg aacaggagag cgcacgaggg    7680
agcttccagg gggaaacgcc tggtatcttt atagtcctgt cgggtttcgc cacctctgac    7740
ttgagcgtcg attttgtga tgctcgtcag ggggcggag cctatggaaa acgccagca      7800 acgcggcctt tttacggttc ctggcctttt gctggccttg aagctgtccc tgatggtcgt    7860
catctacctg cctggacagc atggcctgca acgcgggcat cccgatgccg ccggaagcga    7920
gaagaatcat aatggggaag gccatccagc ctcgcgtcgc gaacgccagc aagacgtagc    7980
ccagcgcgtc ggccccgaga tgcgccgcgt gcggctgctg gagatggcgg acgcgatgga    8040
tatgttctgc caagggttgg tttgcgcatt cacagttctc cgcaagaatt gattggctcc    8100
aattcttgga gtggtgaatc cgttagcgag gtgccgccct gcttcatccc cgtgcccgt     8160 tgctcgcgtt tgctggcggt gtccccggaa gaaatatatt tgcatgtctt tagttctatg    8220
atgacacaaa ccccgcccag cgtcttgtca ttggcgaatt cgaacacgca gatgcagtcg    8280
gggcggcgcg gtccgaggtc cacttcgcat attaaggtga cgcgtgtggc ctcgaacacc    8340
gagcgaccct gcagcgaccc gcttaacagc gtcaacagcg tgccgcagat cccgggggc     8400 aatgagatat gaaaaagcct gaactcaccg cgacgtctgt cgagaagttt ctgatcgaaa    8460
agttcgacag cgtctccgac ctgatgcagc tctcggaggg cgaagaatct cgtgctttca    8520
gcttcgatgt aggagggcgt ggatatgtcc tgcgggtaaa tagctgcgcc gatggtttct    8580
acaaagatcg ttatgtttat cggcactttg catcggccgc gctccgatt ccggaagtgc     8640 ttgacattgg ggaattcagc gagagcctga cctattgcat ctcccgccgt gcacagggtg    8700
tcacgttgca agacctgcct gaaaccgaac tgcccgctgt tctgcagccg gtcgcggagg    8760
ccatggatgc gatcgctgcg gccgatctta gccagacgag cgggttcggc ccattcggac    8820
cgcaaggaat cggtcaatac actacatggc gtgatttcat atgcgcgatt gctgatcccc    8880
atgtgtatca ctggcaaact gtgatggacg acaccgtcag tgcgtccgtc gcgcaggctc    8940
tcgatgagct gatgctttgg gccgaggact gccccgaagt ccggcacctc gtgcacgcgg    9000
atttcggctc caacaatgtc ctgacggaca atggccgcat aacagcggtc attgactgga    9060
gcgaggcgat gttcggggat tcccaatacg aggtcgccaa catcttcttc tggaggccgt    9120
ggttggcttg tatggagcag cagacgcgct acttcgagcg gaggcatccg gagcttgcag    9180
gatcgccgcg gctccgggcg tatatgctcc gcattggtct tgaccaactc tatcagagct    9240
tggttgacgg caatttcgat gatgcagctt gggcgcaggg tcgatgcgac gcaatcgtcc    9300
gatccggagc cgggactgtc gggcgtacac aaatcgcccg cagaagcgcg gccgtctgga    9360
ccgatggctg tgtagaagta ctcgccgata gtggaaaccg acgccccagc actcgtccgg    9420
atcgggagat gggggaggct aactgaaaca cggaaggaga caataccgga aggaacccgc    9480
gctatgacgg caataaaaag acagaataaa acgcacgggg gttgggtcgt tgttcataa     9540 acgcggggtt cggtcccagg gctggcactc tgtcgatacc ccaccgagac cccattgggg    9600
ccaatacgcc cgcgtttctt ccttttcccc accccacccc caagttcgg gtgaaggccc     9660 agggctcgca gccaacgtcg gggcggcagg ccctgccata gccactggcc ccgtgggtta    9720
gggacggggt cccccatggg gaatggttta tggttcgtgg gggttattat tttgggcgtt    9780
gcgtggggtc aggtccacga ctggactgag cagacagacc catggttttt ggatggcctg    9840
ggcatggacc gcatgtactg gcgcgacacg aacaccgggc gtctgtggct gccaaacacc    9900
```

```
cccgacccec    aaaaaccacc    gcgcggattt    ctggcgtgcc    aagctagtcg    accaattctc       9960
atgtttgaca    gcttatcatc    gcagatccgg    gcaacgttgt    tgccattgct    gcaggcgcag      10020
aactggtagg    tatggaagat    ctatacattg    aatcaatatt    ggcaattagc    catattagtc      10080
attggttata    tagcataaat    caatattggc    tattggccat    tgcatacgtt    gtatctatat      10140
cataatatgt    acatttatat    tggctcatgt    ccaatatgac    cgccat                        10186
```

```
<210> SEQ ID NO 21
<211> LENGTH: 1926
<212> TYPE: DNA
<213> ORGANISM: Epstein-barr virus

<400> SEQUENCE: 21
atgtctgacg    aggggccagg    tacaggacct    ggaaatggcc    taggagagaa    gggagacaca        60
tctggaccag    aaggctccgg    cggcagtgga    cctcaaagaa    gaggggtga    taaccatgga       120
cgaggacggg    gaagaggacg    aggacgagga    ggcggaagac    caggagcccc    gggcggctca       180
ggatcagggc    caagacatag    agatggtgtc    cggagacccc    aaaaacgtcc    aagttgcatt       240
ggctgcaaag    ggacccacgg    tggaacagga    gcaggagcag    gagcgggagg    ggcaggagca       300
ggaggggcag    gagcaggagg    aggggcagga    gcaggaggag    gggcaggagg    ggcaggaggg       360
gcaggagggg    caggagcagg    aggagggca    ggagcaggag    gaggcagg    aggggcagga       420
ggggcaggag    caggaggagg    ggcaggagca    ggaggagggg    caggaggggc    aggagcagga       480
ggaggggcag    gaggggcagg    aggggcagga    gcaggaggag    gggcaggagc    aggaggaggg       540
gcaggagggg    caggagcagg    aggaggggca    ggaggggcag    gaggggcagg    agcaggagga       600
ggggcaggag    caggaggggc    aggaggggca    ggagcaggag    gggcaggagc    aggaggagca       660
ggaggagggg    caggaggggc    aggaggggca    ggagcaggag    gggcaggagc    aggaggggca       720
ggagcaggag    gggcaggagc    aggaggggca    ggaggggcag    gagcaggagg    ggcaggaggg       780
gcaggagcag    gaggggcagg    aggggcagga    gcaggaggag    gggcaggagg    ggcaggagca       840
ggaggagggg    caggagggc    aggagcagga    ggggcaggag    gggcaggagc    aggagggca       900
ggaggggcag    gagcaggagg    ggcaggaggg    gcaggagcag    gaggagggc    aggagcagga       960
ggggcaggag    caggaggtgg    aggccgggt    cgaggaggca    gtggaggccg    ggtcgagga      1020
ggtagtggag    gccgggtcg    aggaggtagt    ggaggccgcc    ggggtagagg    acgtgaaaga      1080
gccagggggg    gaagtcgtga    aagagccagg    gggagaggtc    gtggacgtgg    agaaaagagg      1140
cccaggagtc    ccagtagtca    gtcatcatca    tccgggtctc    caccgcgcag    gcccctcca      1200
ggtagaaggc    cattttttca    ccctgtaggg    gaagccgatt    attttgaata    ccaccaagaa      1260
ggtggcccag    atggtgagcc    tgacgtgccc    ccggggagcga    tagagcaggg    ccccgcagat      1320
gacccaggag    aaggcccaag    cactggaccc    cggggtcagg    gtgatggagg    caggcgcaaa      1380
aaaggagggt    ggtttggaaa    gcatcgtggt    caaggaggtt    ccaacccgaa    atttgagaac      1440
attgcagaag    gtttaagagc    tctcctggct    aggagtcacg    tagaaaggac    taccgacgaa      1500
ggaacttggg    tcgccggtgt    gttcgtatat    ggaggtagta    agacctccct    ttacaaccta      1560
aggcgaggaa    ctgcccttgc    tattccacaa    tgtcgtctta    caccattgag    tcgtctcccc      1620
tttggaatgg    cccctggacc    cggcccacaa    cctggcccgc    taagggagtc    cattgtctgt      1680
tatttcatgg    tctttttaca    aactcatata    tttgctgagg    ttttgaagga    tgcgattaag      1740
gaccttgtta    tgacaaagcc    cgctcctacc    tgcaatatca    gggtgactgt    gtgcagcttt      1800
gacgatggag    tagatttgcc    tccctggttt    ccacctatgg    tggaagggc    tgccgcggag      1860
```

```
ggtgatgacg gagatgacgg agatgaagga ggtgatggag atgagggtga ggaagggcag    1920
gagtga                                                                1926
```

<210> SEQ ID NO 22
<211> LENGTH: 641
<212> TYPE: PRT
<213> ORGANISM: Epstein-barr virus

<400> SEQUENCE: 22

```
Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Ala Gly Ala Gly Gly
            100                 105                 110

Gly Gly Ala Gly Gly Ala Gly Gly Ala Gly Ala Gly Gly Ala Gly Gly
        115                 120                 125

Gly Ala Gly Ala Gly Gly Ala Gly Gly Ala Gly Gly Ala Gly Gly Ala
    130                 135                 140

Gly Gly Gly Ala Gly Ala Gly Gly Ala Gly Ala Gly Gly Ala Gly Gly
145                 150                 155                 160

Gly Gly Ala Gly Gly Ala Gly Ala Gly Ala Gly Gly Gly Ala Gly Gly
                165                 170                 175

Ala Gly Gly Gly Ala Gly Gly Ala Gly Ala Gly Gly Gly Ala Gly Gly
            180                 185                 190

Ala Gly Gly Ala Gly Ala Gly Gly Gly Ala Gly Ala Gly Gly Ala Gly
        195                 200                 205

Gly Ala Gly Gly Ala Gly Ala Gly Gly Ala Gly Ala Gly Gly Gly Ala
    210                 215                 220

Gly Gly Ala Gly Gly Ala Gly Ala Gly Gly Ala Gly Ala Gly Gly Ala
225                 230                 235                 240

Gly Ala Gly Gly Ala Gly Ala Gly Gly Ala Gly Ala Gly Gly Ala Gly
                245                 250                 255

Gly Ala Gly Gly Ala Gly Ala Gly Gly Ala Gly Ala Gly Gly Ala Gly
            260                 265                 270

Gly Gly Ala Gly Gly Ala Gly Ala Gly Gly Ala Gly Gly Ala Gly Gly
        275                 280                 285

Ala Gly Gly Ala Gly Gly Ala Gly Ala Gly Gly Ala Gly Gly Ala Gly
    290                 295                 300

Ala Gly Gly Ala Gly Gly Ala Gly Ala Gly Gly Ala Gly Ala Gly Gly
305                 310                 315                 320

Gly Ala Gly Ala Gly Gly Gly Gly Arg Gly Arg Gly Gly Ser Gly Gly
                325                 330                 335

Arg Gly Arg Gly Gly Ser Gly Gly Arg Gly Arg Gly Gly Ser Gly Gly
            340                 345                 350
```

```
Arg Arg Gly Arg Gly Arg Glu Arg Ala Arg Gly Ser Arg Glu Arg
            355                 360             365

Ala Arg Gly Arg Gly Arg Gly Arg Gly Glu Lys Arg Pro Arg Ser Pro
    370                 375             380

Ser Ser Gln Ser Ser Ser Gly Ser Pro Pro Arg Arg Pro Pro Pro
385             390             395             400

Gly Arg Arg Pro Phe Phe His Pro Val Gly Glu Ala Asp Tyr Phe Glu
                405             410             415

Tyr His Gln Glu Gly Gly Pro Asp Gly Glu Pro Asp Val Pro Pro Gly
            420             425             430

Ala Ile Glu Gln Gly Pro Ala Asp Asp Pro Gly Glu Gly Pro Ser Thr
            435             440             445

Gly Pro Arg Gly Gln Gly Asp Gly Gly Arg Arg Lys Lys Gly Gly Trp
    450                 455             460

Phe Gly Lys His Arg Gly Gln Gly Gly Ser Asn Pro Lys Phe Glu Asn
465             470             475             480

Ile Ala Glu Gly Leu Arg Ala Leu Leu Ala Arg Ser His Val Glu Arg
                485             490             495

Thr Thr Asp Glu Gly Thr Trp Val Ala Gly Val Phe Val Tyr Gly Gly
            500             505             510

Ser Lys Thr Ser Leu Tyr Asn Leu Arg Arg Gly Thr Ala Leu Ala Ile
            515             520             525

Pro Gln Cys Arg Leu Thr Pro Leu Ser Arg Leu Pro Phe Gly Met Ala
    530             535             540

Pro Gly Pro Gly Pro Gln Pro Gly Pro Leu Arg Glu Ser Ile Val Cys
545             550             555             560

Tyr Phe Met Val Phe Leu Gln Thr His Ile Phe Ala Glu Val Leu Lys
                565             570             575

Asp Ala Ile Lys Asp Leu Val Met Thr Lys Pro Ala Pro Thr Cys Asn
            580             585             590

Ile Arg Val Thr Val Cys Ser Phe Asp Asp Gly Val Asp Leu Pro Pro
            595             600             605

Trp Phe Pro Pro Met Val Glu Gly Ala Ala Glu Gly Asp Asp Gly
    610             615             620

Asp Asp Gly Asp Glu Gly Gly Asp Gly Asp Glu Gly Glu Gly Gln
625             630             635             640

Glu
```